(12) United States Patent
Hoveyda et al.

(10) Patent No.: US 8,598,400 B2
(45) Date of Patent: Dec. 3, 2013

(54) EFFICIENT METHODS FOR Z- OR CIS-SELECTIVE CROSS-METATHESIS

(75) Inventors: Amir H. Hoveyda, Lincoln, MA (US);
Simon J. Meek, Newtonville, MA (US);
Robert V. O'Brien, Brighton, MA (US);
Josep Llaveria Cros, Tarragona (ES);
Richard R. Schrock, Winchester, MA (US)

(73) Assignees: Massachusetts Institute of Technology, Cambridge, MA (US); Trustees of Boston College, Chestnut Hill, MA (US)

( * ) Notice: Subject to any disclaimer, the term of this patent is extended or adjusted under 35 U.S.C. 154(b) by 320 days.

(21) Appl. No.: 13/023,400

(22) Filed: Feb. 8, 2011

(65) Prior Publication Data

US 2011/0245477 A1    Oct. 6, 2011

Related U.S. Application Data

(60) Provisional application No. 61/302,412, filed on Feb. 8, 2010.

(51) Int. Cl.
*C07C 6/04* (2006.01)
*C07C 6/02* (2006.01)

(52) U.S. Cl.
USPC ........... 585/646; 564/509; 548/473; 548/477; 548/479

(58) Field of Classification Search
None
See application file for complete search history.

(56) References Cited

U.S. PATENT DOCUMENTS

| | | | |
|---|---|---|---|
| 5,055,628 A | 10/1991 | Lin et al. | |
| 5,889,128 A | 3/1999 | Schrock et al. | |
| 6,121,473 A | 9/2000 | Schrock et al. | |
| 6,271,325 B1 | 8/2001 | McConville et al. | |
| 6,306,988 B1 | 10/2001 | Grubbs et al. | |
| 6,316,555 B1 | 11/2001 | Schrock et al. | |
| 6,346,652 B1 | 2/2002 | Schrock et al. | |
| 6,414,097 B1 | 7/2002 | Grubbs et al. | |
| 6,610,806 B2 | 8/2003 | Schrock et al. | |
| 6,855,839 B2 | 2/2005 | McConville et al. | |
| 7,135,544 B2 | 11/2006 | Schrock et al. | |
| 2008/0119678 A1 | 5/2008 | Hock et al. | |

FOREIGN PATENT DOCUMENTS

WO    WO 2009/094201    7/2009

OTHER PUBLICATIONS

[No Author Listed] New catalysts promise faster, cleaner, and more efficient research platform. Science Daily. 2 pages. (Nov. 16, 2008).
Aeilts et al., A readily available and user-friendly chrial catalyst for efficient enantioselective olefin metathesis, Angew Chem Int Ed. 40(8):1452-6 (2001).
Agbossou et al., Synthesis and Reactivity of Chiral Rhenium Alcohol Complexes of the Formula [(η5-C5H5)Re(NO)(PPh3)(ROH)] ⊕ BF4⊖. Chem Berichte.123(6):1293-9 (1990).
Al Obaidi, N. et al., Steric and Electronic Effects on the Chemistry of Molybdenum Octahedrally Co-ordinated by Six Nitrogen Atoms. The Molecular Structure of [Mo {HB(3,5-Me2C3N2H)3)(NO)(Pyrollide)2],J. Chem. Soc., Chem. Commun. 690-692 (1984).
Anderson et al., Kinetic selectivity of olefin metathesis catalysts bearing cyclic (alkyl)(amino)carbenes. Organometallics. 27(4):563-6 (2008).
Ascenso et al., Synthesis and characterization of [W(NC4Me4)2Cl2] and [W(NC4Me4)2(CH3)2], the first azametallocene tungsten complexes with pyrrolyl ligands. Electronic structure and bonding of tungsten bispyrrolyl complexes. Inorg Chem Acta. 356: 249-58 (2003).
Bailey et al., Evaluation of molybdenum and tungsten metathesis catalysts for homogeneous tandem alkane metathesis. Organometallics. 28(1):355-60 (2009).
Barluenga et al., Zirconium-Mediated Coupling Reactions of Amines and Enol or Allyl Ethers: Synthesis of Allyl- and Homoallylamines. Chemistry—A European Journal, vol. 10 Iss1, pp. 109-116 2004.
Bazan et al., Living ring-opening metathesis polymerization of 2,3-difunctionalized 7-oxanorbornenes and 7-oxanorbornadienes by Mo(CHCMe2R)(N-2,6-C6H3-iso-Pr2)(O-tert-Bu)2 and Mo(CHCMe2R)(N-2,6-C6H3-iso-Pr2)(OCMe2CF3)2. J Am Chem Soc. 113(18):6899-907 (1991).
Bei et al., Highly efficient olefin-metathesis catalysts. Pharm Technol. 2008:s18.
Blackwell et al., New approaches to olefin cross-metathesis. J Am Chem Soc. 122:58-71 (2000).
Blackwell, J. et al., Enediynes via sequential acetylide reductive coupling and alkyne metathesis: Easy access to well-defined molybdenum initiators for alkyne metathesis. Organometallics 22, 3351-3353 (2003).
Blanc, F. et al., Dramatic Improvements of Well-Defined Silica Supported Mo-Based Olefin Metathesis Catalysts by Tuning the N-Containing Ligands. J. Am. Chem. Soc.129(27), 8434-8435 (2007).
Blanc, F. et al., Highly Active, Stable, and Selective Well-Defined Silica Supported Mo Imido Olefin Metathesis Catalysts. J. Am. Chem. Soc.129(17), 1044-1045 (2007).
Blanc, F. et al., Surface versus molecular siloxy ligands in well-defined olefin metathesis catalysis: [{(RO)3SiO}Mo(=NAr)(=CHtBu)(CH2tBu)], Angew. Chem. Int. Ed. 45, 1216-1220 (2006).
Bornand et al., Mechanism-based design of a ROMP catalyst for sequence-selective copolyerization. Angew Chem Int Ed Engl. 44(48):7909-11 (2005).
Brunner et al., Catalytic hydrosilylation or hydrogenation at one coordination site of Cp'Fe(Co)(X)] fragments. Angewandte Chemie Intl Ed Engl. 29(10):1131-2 (1990).

(Continued)

*Primary Examiner* — Brian J Davis
(74) *Attorney, Agent, or Firm* — Choate, Hall & Stewart, LLP; Andrea L.C. Robidoux; Xiadong Li

(57) ABSTRACT

The present invention generally relates to methods for performing metathesis reactions, including cross-metathesis reactions. Methods described herein exhibit enhanced activity and stereoselectivity, relative to known methods, and are useful in the synthesis of a large assortment of biologically and therapeutically significant agents.

18 Claims, 6 Drawing Sheets

(56) References Cited

OTHER PUBLICATIONS

Brunner et al., Optisch aktive Übergangsmetall-Komplexe, LI: P-Liganden als optisch aktive Hilfsstoffe in den Komplexen $C_5H_5M(CO)(NO)L$, M = Cr, Mo, W. Chem Ber. 11:673-91.—Abstract only (1978).
Brunner, Optical activity at an asymmetrical manganese atom. Angew Chem. Int Ed Engl. 8:382-3 (1969).
Brunner, Optically active organometallic compounds of transition elements with chiral metal atoms. Angew Chemie Intl Ed. 38(9):1194-1208 (1999).
Brunner, Stability of the metal configuration in chiral-at-metal half-sandwich compounds. Eur J Inorg Chem. 905-12 (2001).
Burdett et al., Renewable monomer feedstocks via olefin metathesis: fundamental mechanistic studies of methyl oleate ethenolysis with the first-generation grubbs catalyst. Organometallics. 23(9):2027-47 (2004).
Cantrell et al., Ring-Opening Metathesis of a Cyclic Imine Organometallics, vol. 19, pp. 3562-3568 (2000).
Chatterjee et al., Olefin Cross-Metathesis. Handbook Metathesis. 2003; 2:246-95.
Connon et al., Recent developments in olefin cross-metathesis. Angew Chem Int Ed Engl. 42(17):1900-23(2003).
Corma et al., Chemical routes for the transformation of biomass into chemicals. Chem Rev. 107(6):2411-502. (2007).
Dias, A. et al., Synthesis, characterisation, crystal structure, reactivity and bonding in titanium complexes containing 2,3,4,5-tetramethylpyrrolyl. J. Chem. Soc., Dalton Trans.1055-1061 (1997).
Dinger et al., High turnover numbers with ruthenium-based metathesis catalysts. Adv Synth Catal. 344(6-7):671-7 (2002).
Dolman et al., Efficient catalytic enantioselective synthesis of unsaturated amines: preparation of small- and medium-ring cyclic amines through mo-catalyzed asymmetric ring-closing metathesis in the absence of solvent. J. Am. Chem. Soc. 124(24):6991-7 (2002).
Dolman, New chiral molybdenum metathesis catalysts; application of the enantioselective preparation of cyclic amines, Ph.D. Thesis. MIT. 234 pages. (Jun. 2004).
Duarte, M. et al., Chlorobis(dimethylamido)($\eta^5$-2,5-dimethylpyrrolyl)titanium(IV), [Ti(NMe$_2$)$_2$(DMP)Cl]. Acta Cryst. C.61, 104-106 (2005).
Feldman, J. et al., Recent advances in the schnistry of "d0" alkylidine metallacyclobutane complexes. Prog. Inorg. Chem.39, 1-74 (1991).
Flook et al., Z-selective olefin metathesis processes catalyzed by a molybdenum hexaisopropylterphenoxide monopyrrolide complex. J. Am Chem Soc.131(23):7962-3 (2009).
Fontecave et al., Chiral-at-metal complexes as asymmetric catalysts, In Chiral Diazaligands for Asymmetric Synthesis. Top Organometallic Chem.15(2005):271-88 (2005).
Forman et al., A stable ruthenium catalyst for productive olefin metathesis. Organometallics. 23(21);4824-7 (2004).
Füurstner et al., Cationic ruthenium allenylidene complexes as catalysts for ring closing olefin metathesis. Chemistry. 6(10):1847-57 (2000).
Fürstner, A. et al., Alkyne metathesis: Development of a novel molybdenum-based catalyst system and its application to the total synthesis of Epothilone A and C. Chem. Eur. J. 7(24), 5299-5317 (2001).
Fürstner, A. et al., Mo[N(t-Bu)(Ar)]$_3$ complexes as catalyst precursors: in situ activation and application to metathesis reactions of alkynes and diynes. J. Am. Chem. Soc. 121, 9453-9454 (1999).
Ganter, Chiral organometallic half-sandwich complexes with defined metal configuration. Chem Soc Rev. 32(3):130-8 (2003).
Giessert et al., Intermolecular enol ether-alkyne metathesis, Org Lett. 5(10):1793-6 (2003).
Gillingham et al., Chiral N-heterocyclic carbenes in natural product synthesis: application of Ru-catalyzed asymmetric ring-opening/cross-metathesis and Cu-catalyzed allylic alkylation to total synthesis of baconipyrone C. Angew Chem Int Ed Engl. 46(21):3860-4 (2007).

Giudici et al., Directed catalytic asymmetric olefin metathesis. Selectivity control by enoate and ynoate groups in Ru-catalyzed asymmetric ring-opening/cross-metathesis. J Am Chem Soc.129(13):3824-5 (2007).
Hadlington, Catalyst flexes for extra control. Chemistry World. Nov. 17, 2008. Last accessed online. Dec. 1, 2008.
Herrmann et al., Methyltrioxorhenium als Katalysator für die Olefin-Metathese. Angew Chem 103:1704-1706 (1991).
Herrmann et al., Methyltrioxorhenium as Catalyst for Olefin Metathesis. Angew Chem Int. Ed. Engl. 103:1636-1638 (1991).
Hesek et al., The first asymmetric synthesis of chiral ruthenium tris(bipyridine) from racemic ruthenium bis(bipyridine) complexes. Tetrahedron Lett. 41(15):2617-20 (2000).
Hock, A. et al., Dipyrrolyl Precursors to Bisalkoxide Molybdenum Olefin Metathesis Catalysts. J. Am. Chem. Soc.128(50), 16373-16375 (2006).
Ibrahem et al., Highly Z- and enantioselective ring-opening/cross-metathesis reactions catalyzed by stereogenic-at-Mo adamantylimido complexes. J Am Chem Soc.131(11):3844-5 (2009).
International Preliminary Report on Patentability for PCT/US2010/002644, issued Apr. 3, 2012.
International Preliminary Report on Patentability for PCT/US2011/024100, issued Aug. 14, 2012.
International Preliminary Report on Patentability from International Patent Application Serial No. PCT/US2007/024318, filed Nov. 21, 2007, mailed May 26, 2009.
International Preliminary Report on Patentability in connection with Application Serial No. PCT/US2009/000465 issued Jul. 27, 2010.
International Search Report and Written Opinion in connection with Application Serial No. PCT/US2009/000465 mailed Jul. 13, 2009.
International Search Report and Written Opinion in PCT/US2007/024318, mailed on May 7, 2008.
International Search Report for PCT/US2010/002644, mailed Mar. 7, 2011.
International Search Report and Written Opinion in PCT/US2011/024100, mailed on Apr. 23, 2011.
Jiang et al., Fundamental studies of tungsten alkylidene imido monoalkoxidepyrrolide complexes. J Am Chem Soc.131(22):7770-80 (2009).
Jiang et al., Highly Z-selective metathesis homocoupling of terminal olefins, J Am Chem Soc. 131(46):16630-1 (2009).
Kershner, D. et al., $\eta$5-Heterocyclic Metal Carbonyls. Coord. Chem. Rev. 79, 279-92 (1987).
Kiely et al., Enantioselective synthesis of medium-ring heterocycles, tertiary ethers, and tertiary alcohols by Mo-catalyzed ring-closing metathesis. J Am Chem Soc. 124(12):2868-9 (2002).
Knof et al., Predetermined chirality at metal centers. Angew Chemie Intl Ed. 38(3):302-22 (1999).
Kreickmann, T., et al., Imido Alkylidene Bispyrrolyl Complexes of Tungsten. Organometallics. 26, 5702-5711 (2007).
Lacour et al., Recent developments in chiral anion mediated asymmetric chemistry. Chem Soc Rev. 32(6):373-82 (2003).
Lee et al., Enantioselective synthesis of cyclic enol ethers and all-carbon quaternary stereogenic centers through catalytic asymmetric ring-closing metathesis. J Am Chem Soc. 128(15):5153-7 (2006).
Lee et al., Endo-selective enyne ring-closing metathesis promoted by stereogenic-at-Mo monoalkoxide and monoaryloxide complexes. Efficient synthesis of cyclic dienes not accessible through reactions with Ru carbenes. J Am Chem Soc.131(30):10652-61 (2009).
Liu et al., Regioselective ring-opening/cross-metathesis reactions of norbornene derivatives with electron-rich olefins. Org Lett. 7(I):131-3 (2005).
Lokare et al., Synthesis, properties, and structure of tethered molybdenum alkylidenes. Organometallics. 27(19):5130-8 (2008).
Malcolmson et al., Highly efficient molybdenum-based catalysts for enantioselective alkene metathesis. Nature. 456(7224):933-7 (2008).
Marinescu et al., Ethenolysis reactions catalyzed by imido alkylidene monoaryloxide monopyrrolide (MAP) complexes of molybdenum. J Am Chem Soc. Aug. 12, 2009;131(31):10840-1 (2009).
Marinescu et al., Inversion of configuration at the metal in diastereomeric imido alkylidene monoaryloxide monopyrrolide complexes of molybdenum. J Am Chem Soc.131 (1):58-9 (2009).

(56) References Cited

OTHER PUBLICATIONS

Maruoka et al., Efficient synthesis of sterically hindered chiral binaphthol derivatives. Bull Chem Soc Jpn. 61(8):2975-6 (1988).
McDougal et al., Asymmetric Morita-Baylis-Hillman reactions catalyzed by chiral Bronsted acids. J Am Chem Soc. 125(40):12094-5 (2003).
McDougal et al., The development of the asymmetric morita-baylis-hillman reaction catalyzed by chiral bronsted acids, Adv Synth Cat 346;1231-40 (2004).
Meek et al., The significance of degenerate processes to enantioselective olefin metathesis reactions promoted by stereogenic-at-Mo complexes. J Am Chem Soc.131(45):16407-9 (2009).
Monchaud et al., Ion-pair-mediated asymmetric synthesis of a configurationally stable mononuclear tris(diimine)-iron(II) complex. Angew Chem Int Ed Engl. 41(13):2317-9 (2002).
Nicolaou et al. Metathesis reactions in total synthesis. Angew Chem Int Ed Engl. 44(29):4490-527 (2005).
Pezet et al., Highly diastereoselective preparation of ruthenium bis(diimine) sulfoxide complexes: new concept in the preparation of optically active octahedral ruthenium complexes. Organometallics. 19(20):4008-15 (2000).
Poater et al., Understanding d(0)-olefin metathesis catalysts: which metal, which ligands? J Am Chem Soc.129(26):8207-16 (2007).
Rhers, B. et al., A well-defined, silica-supported tungsten imido alkylidene olefin metathesis catalyst. Organometallics. 25, 3554-3557 (2006).
Sattely et al., Design and stereoselective preparation of a new class of chiral olefin metathesis catalysts and application to enantioselective synthesis of quebrachamine:0 catalyst development inspired by natural product synthesis. J Am Chem Soc.131(3):943-53 (2009).
Sattely et al., Enantioselective synthesis of cyclic amides and amines through mo-catalyzed asymmetric ring-closing metathesis. J Am Chem Soc.127(23):8526-33 (2005).
Sattely, Cyclic amines and amides through molybdenum-catalyzed asymmetric olefin metathesis: A total synthesis of quebrachamine. Boston College Dissertations and Theses. Paper AAI3256831. http://escholarship.bc.edu/dissertations/AAI3256831. 340 pages. (Jan. 1, 2007).
Schrock et al., Further studies of imido alkylidene complexes of tungsten, well-characterized olefm metathesis catalysts with controllable activity. Organometallics, vol. 9, No. 8, pp. 2262-2275 (1990).
Schrock et al., Thousands of catalysts for olefin metathesis: variability, longevity and asymmetry at the metal. Abstract. Presented at Technical University of Berlin (Oct. 24, 2008).
Schrock, R. et al., Molybdenum alkylidyne complexes that contain 3,3'-di-t-butyl-5,5', 6,6'-tetramethy1-1, 11-biphenyl-2,21-diolate ([Biphen]$^{2-}$) ligand. J. Organomet, Chem. 684, 56-67 (2003).
Schrock, R. et al., Molybdenum and tungsten imido alkylidene complexes as efficient olefin-metathesis catalysts. Angew. Chem. Int. Ed. 42, 4592-4633 (2003).
Schrock, R. et al., Preparation of molybdenum and tungsten neopentylidyne complexes of the type M(CCMe$_3$)(O$_2$CR)$_3$, their reactions with acetylenes, and the X-ray structure of the $\eta^3$-cyclopropenyl complex W[C$_3$(CMe$_3$)Et$_2$]O$_2$CCH$_3$)$_3$. Organometallics. 5, 25-33 (1986).
Schrock, R. et al., Synthesis of Molybdenum Imido Alkylidene Complexes and Some Reactions Involving Acyclic Olefins. J. Am. Chem. Soc. 112, 3875-3886 (1990).
Schrock, R., High oxidation state multiple metal-carbon bonds. Chem. Rev.102, 145-179 (2002).
Schrock, Recent advances in high oxidation state Mo and W imido alkylidene chemistry. Chem Rev. 109(8):3211-26 (2009).
Schrodi et al., Ruthenium olefin metathesis catalysts for the ethenolysis of renewable feedstocks. Clean: Soil, Air, Water. 36:669-673 (2008).
Singh, R. et al., Molybdenum Imido Alkylidene Metathesis Catalysts That Contain Electron-Withdrawing Biphenolates or Binaphtholates. Organometallics. 26(10), 2528-2539 (2007).
Singh, R. et al., Synthesis of Monoalkoxide Monopyrrolyl Complexes Mo(NR)(CHR')(OR")(pyrrolyl): Enyne Metathesis with High Oxidation State Catalysts. J. Am. Chem. Soc.129(42), 12654-12655 (2007).

Sinha, A. et al., Diphenylamido precursors to bisalkoxide molybdenum olefin metathesis catalysts. Organometallics. 25, 4621-4626 (2006).
Sinha, A. et al., Reactions of M(N-2,6-i-Pr$_2$C$_6$H$_3$)(CHR)(CH$_2$R')$_2$ (M = Mo, W) Complexes with Alcohols to Give Olefin Metathesis Catalysts of the Type M(N-2,6-i-Pr$_2$C$_6$H$_3$)(CHR)(CH$_2$R')(OR"). Organometallics. 25, 1412-23 (2006).
Solans-Monfort et al., d$^0$ Re-based olefin metathesis catalysts, Re(=CR)(=CHR)(X)(Y): The key role of X and Y ligands for efficient active sites. J Am Chem Soc.127(40):14015-25 (2005).
Takano et al., Enantioselective route to both (+)- and (−)-enantiomers of quebrachamine using a single chiral synthon. J Chem Soc Chem Commun. 1153-5 (1981).
Takemura et al., Stereochemical aspects of asymmetric Diels-Alder reaction catalyzed by chiral alkoxyaluminum dichlorides. Tetrahedron Lett 1987;28(46):5687-90 (1987).
Tallarico et al., Selectivity in ring-opening metatheses. Tetrahedron. 53(48):16511-20 (1997).
Tayama et al., Activation of ether functionality of allyl vinyl ethers by chiral bis(organoaluminum) Lewis acids: application to asymmetric Claisen rearrangement Tetrahedron. 58(41):8307-12 (2002).
Tonzetich, Z. et al., Reaction of Phosphoranes with Mo(N-2,6-i-Pr$_2$C$_6$H$_3$)(CHCMe$_3$)[OCMe(CF$_3$)$_2$]$_2$: Synthesis and Reactivity of an Anionic Imido Alkylidyne Complex. Organometallics. 25, 4301-4306 (2006).
Tsai, Y. et al, Facile synthesis of trialkoxymolybdenum(VI) alkylidyne complexes for alkyne metathesis. Organometallics. 19, 5260-5262 (2000).
Van Veldhuizen et al., A readily available chiral Ag-based N-heterocyclic carbene complex for use in efficient and highly enantioselective Ru-catalyzed olefin metathesis and Cu-catalyzed allylic alkylation reactions. J Am Chem Soc.127(18):6877-82 (2005).
Van Veldhuizen et al., A recyclable chiral Ru catalyst for enantioselective olefin metathesis. Efficient catalytic asymmetric ring-opening/cross metathesis in air. J Am Chem Soc. May 8, 2002;124(18):4954-5. Erratum in: J Am Chem Soc.125(41):12666 (2003).
Walls et al., Alkaloids from stemmadenia species-I : The alkaloids of S. Donnell-Smithii and S. Galeottiana. Tetrahedron. 2(3-4):173-82 (1958).
Weatherhead et al., Mo-catalyzed asymmetric olefin metathesis in target-oriented synthesis: enantioselective synthesis of (+)-africanol. Proc Natl Acad Sci U S A.101(16):5805-9 (2004).
Werner et al., Bur Kennfnie dee asymmetrimhen Kobaltatoms. I. Ber Dtsch Chem Ges. 44:1887-98. German (1911).
Written Opinion for PCT/US2010/002644, mailed Mar. 7, 2011.
Yashiro et al., Efficient stereochemical regulation of octahedral cobalt(III) complexes by a chiral bidentate ligand. Part 2. Remarkable effect of the chelate-ring size in the stereoselective formation of sym-cis-(ethylenediamine-N,N'-diacetato)(pentane-2,4-diamine)cobalt(III). J Chem Soc. Dalton Trans.10:1511-6 (1994).
Yashiro et al., Efficient stereochemical regulation of octahedral cobalt(III) complexes by a chiral bidentate ligand. Part I. Effect of N-alkyl substitutions. J Chem Sco, Dalton Trans. 7:10773-7 (1994).
Yi et al., The ruthenium acetylide catalyzed cross-coupling reaction of terminal and internal alkynes: isolation of a catalytically active p-agostic intermediate species. Organometallics. 17(15):3158-60 (1998).
Zhang, W. et al., A reductive recycle strategy for the facile synthesis of molybdenum(VI) alkylidyne catalysts for alkyne metathesis. Chem. Commun. 832-833 (2003).
Zhou et al., Synthesis and reactivity of chiral rhenium indenyl complexes of the formula [($\eta$5-C9H7)Re(NO)(PPh3)(X)]n+. Organometallics.12(10);3918-23 (1993).
Zhu et al., Chiral Mo-Binol complexes: activity, synthesis, and structure. efficient enantioselective six-membered ring synthesis through catalytic metathesis. J Am Chem Soc. 121:8251-9 (1999).
Communication in European Patent Application No. 11740541.5, dated Jul. 26, 2013.
Fujiwhara et al., Ruthenium-catalyzed regioselective codimerization of enol acrylates with 2-substituted-1,3-butadienes, Org. Lett. 1(10): 1635-1637 (1999).

Scheme 1. Stereogenic-at-Mo Chiral Complexes and Structural Attributes that can Lead to High Z-Selectivity in a Cross-Metathesis Reaction

US 8,598,400 B2

EFFICIENT METHODS FOR Z- OR CIS-SELECTIVE CROSS-METATHESIS

CROSS-REFERENCE TO RELATED APPLICATIONS

The present invention claims priority to U.S. provisional application Ser. No. 61/302,412, filed Feb. 8, 2010, the entirety of which is hereby incorporated herein by reference.

STATEMENT REGARDING FEDERALLY SPONSORED RESEARCH OR DEVELOPMENT

THIS INVENTION WAS MADE WITH THE SUPPORT UNDER THE FOLLOWING GOVERNMENT CONTRACT: GM59426, AWARDED BY THE NATIONAL INSTITUTES OF HEALTH. THE GOVERNMENT HAS CERTAIN RIGHTS IN THE INVENTION.

FIELD OF THE INVENTION

The present invention generally relates to methods for cross-metathesis of substrates, including enol ethers, allylic amides, and allylic amines.

BACKGROUND

The need for reliable methods that furnish alkenes efficiently and stereoselectively continues to represent a difficult and most compelling challenge in the field of chemical synthesis. Protocols that are catalytic or deliver thermodynamically less favored Z alkenes are particularly scarce. Olefin synthesis through Wittig-type protocols is one of the more commonly used procedures for accessing cis disubstituted olefins; such transformations, however, require stoichiometric amounts of arylphosphonium salts, leading to notoriously low degrees of atom economy and, at times, complicated and costly purification procedures. Catalytic hydrogenation of alkynes is another established route that leads to Z olefins. Synthesis of the requisite substrates is, however, not always straightforward, reactions require catalysts that are based on expensive precious metals (e.g., Pd-, Pt-, or Rh-based) and a lead-based component (e.g., $Pb(OAc)_2$), over-reduction is often a concern (separation of the desired alkene and the adventitious alkane is typically not straightforward).

Catalytic olefin metathesis has transformed chemical synthesis and offers exceptionally efficient pathways for synthesis of alkenes. Among various types of olefin metathesis, cross-metathesis of two different terminal alkenes, a reaction that generates only the easily removable ethylene as the side-product, constitutes a remarkably attractive and efficient strategy for synthesis of disubstituted alkenes. Cross-metathesis, however, is a mechanistically complicated variant of this class of transformations. In ring-closing metathesis, reacting alkenes are tethered and the intramolecular reaction is favored; in ring-opening metathesis, release of strain typically serves as the driving force that results in one of several pathways to be preferred. In contrast, cross-metathesis demands that two different alkenes react without the entropic benefit of an intramolecular reaction or strain release, and under conditions that can also cause homo-coupling of the cross partners. What often renders the goal of a Z-selective cross-metathesis process a daunting challenge is that in the case of the large majority of related reactions reported thus far, the large majority of which are promoted by Ru-based carbenes, the energetically favored E olefin products are formed either predominantly or exclusively. It should be noted that early studies demonstrated that styrene and a variety of terminal alkenes undergo cross-metathesis in the presence of 1-5 mol % of an achiral Mo bis-alkoxide. Transformations were found to be highly E-selective (81% to >98% E). Only when acrylonitrile is used instead (vs. styrene) Z alkene products are formed predominantly (75-88% Z).

A great number of biologically active molecules and polymeric materials contain olefins; many reactions in organic chemistry require alkenes as starting materials. Disubstituted alkenes can exist as E or Z isomers, each possessing a unique geometry and distinct energetic attribute. Molecules with E or Z alkenes might exhibit different reactivity, selectivity and/or binding profiles with biological receptors. Methods that are catalytic and allow for stereoselective formation of olefins are therefore of considerable value. Such protocols are, however, relatively uncommon. Particularly scarce are efficient catalytic procedures for stereoselective synthesis of the higher energy Z alkenes.

Accordingly, there remains an unmet need for methods and catalysts for Z-selective cross metathesis reactions.

SUMMARY

The present invention relates to methods for performing various reactions, including metathesis reactions. Some embodiments provide the ability to produce compounds comprising a double bond having a Z:E ratio greater than about 1:1 in favor of the Z-isomer. Using previous methods, it would be expected that double bonds having an E-configuration would represent the major product formed in a methathesis reaction, since double bonds having an E configuration are thermodynamically favored product. Thus, it was surprisingly found that methods described herein allow for the formation of double bonds having a Z-configuration as the major product.

In some embodiments, the method comprises reacting a first species comprising an olefin and a second species comprising an enol ether via an intermolecular cross-metathesis reaction to produce a product comprising a double bond, the double bond comprising an atom of the first species and an atom of the second species, wherein the double bond is produced in a Z:E ratio greater than about 1:1 in favor of the Z-isomer.

In some embodiments, the method comprises reacting a first species comprising an olefin and a second species comprising an allylic amine via an intermolecular cross-metathesis reaction to produce a product comprising a double bond, the double bond comprising an atom of the first species and an atom of the second species, wherein the double bond is produced in a Z:E ratio greater than about 1:1 in favor of the Z-isomer.

In other embodiments, a provided method comprises a first species comprising an olefin and a second species comprising an allylic amide via an intermolecular cross-metathesis reaction to produce a product comprising a double bond, the double bond comprising an atom of the first species and an atom of the second species, wherein the double bond is produced in a Z:E ratio greater than about 1:1 in favor of the Z-isomer.

Figure 1:
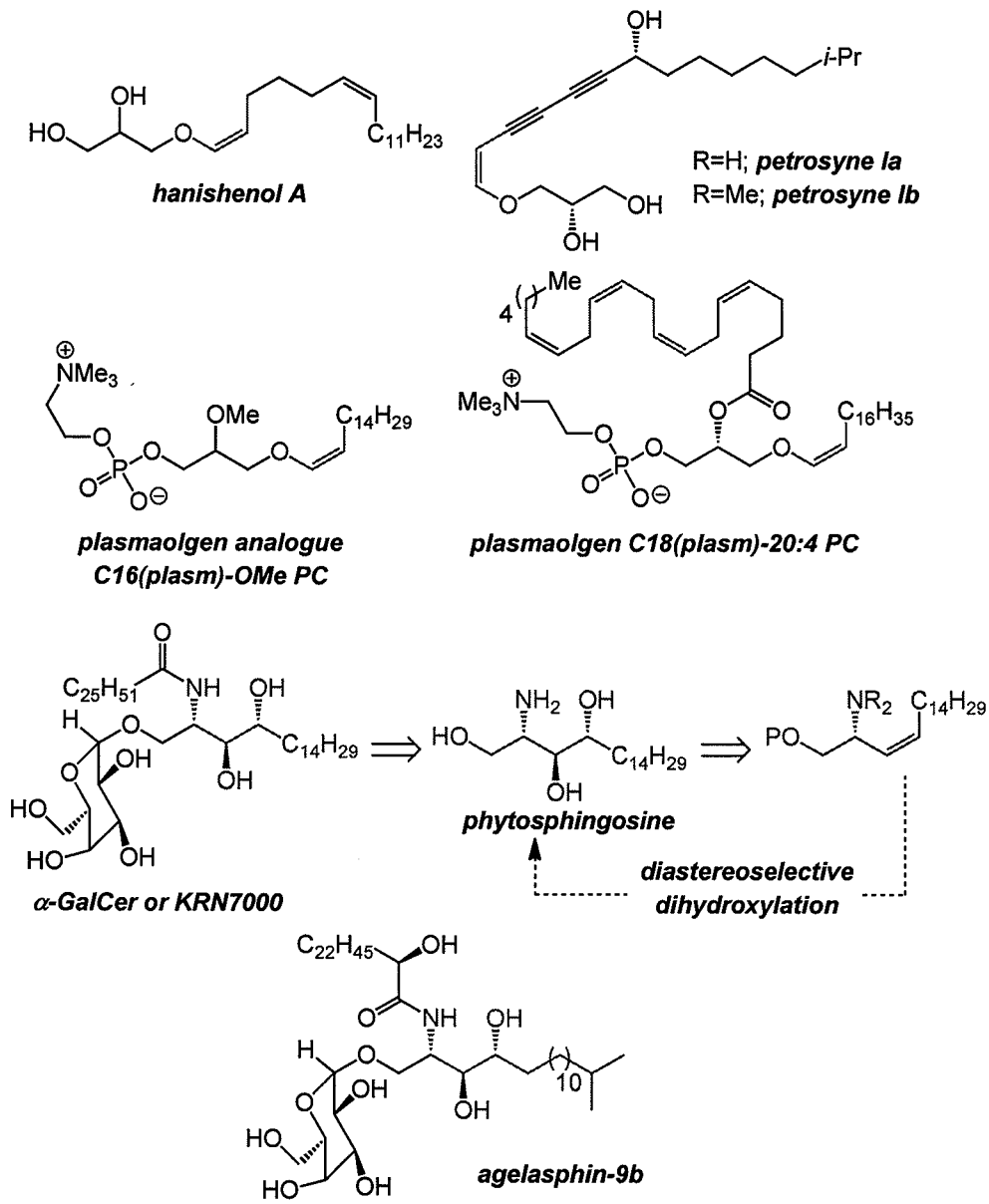
FIG. 1 shows examples of natural products which include an olefin having a Z configuration.

Other aspects, embodiments and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION OF CERTAIN EMBODIMENTS

1. General Description of Certain Embodiments of the Invention

Catalytic cross-metathesis offers an attractive option for stereoselective olefin synthesis. However, the only reported cases of Z-selective cross-metathesis (65-90% Z) involve substrates that bear an sp-hybridized substituent (i.e., acrylonitrile or an enyne). Catalytic cross-metathesis is a mechanistically complex process that can generate six different olefins: the E and Z cross products and two isomeric forms of each of the two possible 1,2-disubstituted alkenes derived from olefin homocoupling. An efficient Z-selective cross-metathesis presents a significant challenge in reaction development. Such a transformation is not only required to favor reaction between the two substrates selectively (vs homocoupling), it must exhibit a preference for the thermodynamically less favored stereoisomer. Furthermore, the inherent reversibility of olefin metathesis (products can re-enter the catalytic cycle) and the higher reactivity of Z alkenes, compared to their more energetically favored E isomers, render achieving an efficient Z-selective process especially difficult. Conditions must therefore be established where the catalyst promotes cross metathesis between two terminal olefins but does not react with the product Z olefin to regenerate the starting materials and effect equilibration favoring the lower energy E isomer.

Designing an efficient Z-selective cross-metathesis is significantly more challenging for a number of reasons. In a homocoupling, only one alkene is involved and no more than two stereoisomeric olefins can be formed; in contrast, there are two different substrates and up to six products can be generated in a cross-metathesis. In the case of a catalytic ROCM, a strained cyclic alkene and a terminal olefin, reluctant to undergo homocoupling (e.g., a styrene), are selected as substrates so that the course of the catalytic process can be controlled in favor of the ROCM product. Transformations are therefore carefully crafted such that the alkylidene derived from the terminal alkene favors association with the cyclic olefin (vs. another molecule of the same type) in the ring-opening stage, generating a new Mo complex that prefers to react with a sterically less demanding terminal alkene (catalytic olefin metathesis stage). The possibility of a transformation between the alkylidene generated through ring-opening and another strained—but more hindered—cyclic alkene is thus discouraged (i.e., minimal homocoupling or oligomerization). Such deliberate orchestration is not feasible with catalytic cross-metathesis, where both alkenes are mono-substituted and manipulation of ring strain is not an option.

Z-disubstituted enol ethers and allylic amines play a significant role in the synthesis of a number of important biologically active molecules; representative examples are shown in FIG. 1. Hanishenol A and petrosynes Ia and Ib are glycerol-based Z enol ether-containing metabolites, isolated from Red Sea and Okinawan marine sponges. Plasmalogens, glycerophospholipids found in high concentration in human brain as well as in lung, kidney, spleen and skeletal muscles, contain a polar head group and a Z enol ether moiety. Plasmalogens play a critical role in determining the physical properties of neural membranes. Although the function of plasmalogens in mammalian tissue is complex, it has been established that these entities are anti-oxidants and serve as a reservoir for arachidonate and docosahexaenoate; the Z stereochemistry of the enol ether unit has been shown pivotal to such attributes. Interest in plasmalogens has increased over the past few years, stimulated by findings that link a deficiency in their biosynthesis to human degenerative diseases (e.g., Alzheimer's disease) and genetic disorders (such as the Zellweger syndrome). Plasmalogen analogues of antitumor ether lipids (AEL's) such as Et-18-OMe (edelfosine) have been synthesized (e.g., C16(plasm)-OMe PC, FIG. 1) and shown to exhibit similar cytotoxic properties to the corresponding AEL analogues.

Z-Allylic amines are highly desirable, since they can be stereoselectively functionalized towards preparation of other biologically significant molecules. As the example in FIG. 1 illustrates, synthesis of the acyclic segment of α-galcer (or KRN 7000, a highly potent immunostimulant with antitumorigenic properties) or agelasphine-9b might involve a diastereoselective dihydroxylation of an allylic amine; access to the appropriate stereoisomer and in high selectivity requires access to the Z-disubstituted alkene. In a similar manner, an efficient route that allows access to phytosphingosine, a key component of β-glycosphingolipids, would require diastereoselective dihydroxylation of an appropriate Z allylic amine (reaction of the E isomer has been shown to be significantly less selective; 3-5:1 dr for the E-isomer and 20:1 dr for the Z-isomer). β-Glycosphingolipids are commonly occurring components of eukaryotic cells that play a critical role in cellular trafficking and signaling events and which reside within membrane areas believed to be preferential sites for host pathogen/toxin interactions, and generation of infected forms of proteins tied to various diseases of the nervous system (e.g., Alzheimer and prion diseases).

The utility of the method of cross-metathesis of cross-metathesis (CM) reactions of enol ethers and allylic amides is highlighted with stereoselective synthesis of C18 (plasm)-16:0 (PC), an anti-oxidant found in electronically active brain and heart tissues, which has been implicated in Alzheimer's disease. Another application relates to synthesis of the potent immunostimulant and anti-tumor agent KRN7000. Stereoselective synthesis of KRN7000 underlines the utility of cross-metathesis (CM) reactions of enol ethers and allylic amides. Indeed, Z-selective CM provides access to a route that is significantly more concise than the 14-step sequence (vs steps) reported thus far as the shortest synthesis of KRN7000.

The present invention generally relates to Z-selective cross-metathesis reactions. In some embodiments, the reaction is performed in the presence of a catalyst, which is readily prepared from commercially or easily available starting materials and/or used in situ. Methods described in detail herein exhibit enhanced activity and stereoselectivity, relative to known methods, and are useful in the synthesis of a large assortment of biologically and therapeutically significant agents.

2. Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon, bicyclic hydrocarbon, or tricyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-30 aliphatic carbon atoms. In some embodiments, aliphatic groups contain 1-20 aliphatic carbon atoms. In other embodiments, aliphatic groups contain 1-10 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. In some embodiments, "cycloaliphatic" (or "carbocycle" or "cycloalkyl") refers to a monocyclic $C_3$-$C_6$ hydrocarbon, or a $C_8$-$C_{10}$ bicyclic hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 1-30 carbon atoms in its backbone (e.g., $C_1$-$C_{30}$ for straight chain, $C_2$-$C_{30}$ for branched chain), and alternatively, about 1-20. In some embodiments, a cycloalkyl ring has from about 3-10 carbon atoms in their ring structure where such rings are monocyclic or bicyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

As used herein, the term "alkenyl" refers to an alkyl group, as defined herein, having one or more double bonds.

As used herein, the term "alkynyl" refers to an alkyl group, as defined herein, having one or more triple bonds.

The term "heteroalkyl" is given its ordinary meaning in the art and refers to alkyl groups as described herein in which one or more carbon atoms is replaced with a heteroatom (e.g., oxygen, nitrogen, sulfur, and the like). Examples of heteroalkyl groups include, but are not limited to, alkoxy, poly (ethylene glycol)-, alkyl-substituted amino, tetrahydrofuranyl, piperidinyl, morpholinyl, etc.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms (i.e., monocyclic or bicyclic), in some embodiments 5, 6, 9, or 10 ring atoms. In some embodiments, such rings have 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3 (4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

Examples of aryl and heteroaryl groups include, but are not limited to, phenyl, pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. It should be understood that, when aryl and heteroaryl groups are used as ligands coordinating a metal center, the aryl and heteroaryl groups may have sufficient ionic character to coordinate the metal center. For example, when a heteroaryl group such as pyrrole is used as a nitrogen-containing ligand, as described herein, it should be understood that the pyrrole group has sufficient ionic character (e.g., is sufficiently deprotonated to define a pyrrolyl) to coordinate the metal center. In some cases, the aryl or heteroaryl group may comprise at least on functional group that has sufficient ionic character to coordinate the metal center, such as a biphenolate group, for example.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl-ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

The term "allyl" is given its ordinary meaning in the art and refers to a group comprising a methylene group attached to a vinyl group, i.e., $H_2C=CH-CR_2-$.

The term "allylic amine" is given its ordinary meaning in the art and refers to a molecule comprising a carbon-carbon double bond adjacent an amine group. In some embodiments, the allylic amine is of formula, $H_2C=CH-C(R')_2N(R'')_2$, as described herein.

The term "enol ether" is given its ordinary meaning in the art and refers to an ether molecule comprising a carbon-carbon double bond adjacent the oxygen atom of the ether group. In some embodiments, an enol ether comprises a compound of formula $H_2C=C(R^b)OR$, as described herein.

The term "olefin," as used herein, refers to any species having at least one ethylenic double bond. By way of non-limiting example, exemplary such olefins include optionally substituted normal and/or branched chain aliphatic or heteroaliphatic olefins, optionally substituted cycloaliphatic and heterocycloaliphatic olefins, optionally substituted aryl and heteroaryl substituted olefins, and the like.

The term "cyclic olefin," as used herein, refers to any cyclic species comprising at least one ethylenic double bond in a ring. The atoms of the ring may be optionally substituted. The ring may comprise any number of carbon atoms and/or heteroatoms. In some cases, the cyclic olefin may comprise more than one ring. A ring may comprise at least 3, at least 4, at least 5, at least 6, at least 7, at least 8, or more, atoms. Non-limiting examples of cyclic olefins include norbornene, dicyclopentadiene, a bicyclo compound, an oxabicyclo compound, and the like, all optionally substituted. "Bicyclo compounds" are a class of compounds consisting of two rings only, having two or more atoms in common. "Oxabicyclo compounds" are a class of compounds consisting of two rings only, having two or more atoms in common, wherein at least one ring comprises an oxygen atom.

Such rings are also referred to as "partially unsaturated" which means a carbocyclic or heterocyclic ring having one or more units of unsaturation but are not aromatic.

The terms "carboxyl group," "carbonyl group," and "acyl group" are recognized in the art and can include such moieties comprising —C(O)—. Such moieties comprising —C(O)— include those of formula —C(O)R° which includes aldehydes (when R° is hydrogen) and ketones (when when R° is optionally substituted aliphatic, aryl, or heteroaryl), or formula —C(O)OR° which includes carboxylic acids (when R° is hydrogen) and carboxylic esters (when R° is optionally substituted aliphatic, aryl, or heteroaryl).The term "carboxylate" refers to an anionic carboxyl group. In general, where the oxygen atom of the "—OR°" portion of the formula —C(O)OR° is replaced by sulfur, the formula represents a "thiolcarbonyl" group. Where the "—SR°" portion of —C(O)SR° is S-alkyl, the formula represents a "thiolester." Where the "—SR°" portion of —C(O)SR° is SH, the formula represents a "thiolcarboxylic acid."

The term "alkoxy" refers to the group, —OR°.

The term "aryloxy" refers to the group, —O-aryl, wherein the aryl moiety is optionally substituted.

The term "acyloxy" refers to the group, —OC(O)R°.

The term "arylalkyl," as used herein, refers to an alkyl group substituted with an aryl group that is optionally substituted.

The terms "amine" and "amino" are art-recognized and refer to both unsubstituted and substituted amines, e.g., a moiety that can be represented by —NH$_2$ or the general formula: N(R')(R") wherein R' and R" each independently represent a group and/or a suitable substituent on a nitrogen atom as described herein.

An "alkoxide" ligand herein refers to a ligand prepared from an alcohol, in that removing the hydroxyl proton from an alcohol results in a negatively charged alkoxide.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

The term "halogen" means F, Cl, Br, or I.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched)alkylene)O—N(R°)$_2$; or —(C$_{1-4}$ straight or branched)alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR$^\bullet$$_2$)$_{2-3}$O—, wherein each independent occurrence of R$^\bullet$ is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

In some embodiments, the term "substituted" is contemplated to include all permissible substituents of organic compounds, "permissible" being in the context of the chemical rules of valence known to those of ordinary skill in the art. In some cases, "substituted" may generally refer to replacement of a hydrogen atom with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl" group must still comprise the phenyl moiety and cannot be modified by substitution, in this definition, to become, e.g., a cyclohexyl group. In a broad aspect, permissible substituents include acyclic and cyclic, branched and unbranched, carbocyclic and heterocyclic, aromatic and nonaromatic substituents of organic compounds. Illustrative substituents include, for example, those described herein. Permissible substituents can be one or more and the same or different for appropriate organic compounds. For example, a substituted alkyl group may be $CF_3$. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Examples of substituents include, but are not limited to, alkyl, aryl, arylalkyl, cyclic alkyl, heterocycloalkyl, hydroxy, alkoxy, aryloxy, perhaloalkoxy, arylalkoxy, heteroaryl, heteroaryloxy, heteroarylalkyl, heteroarylalkoxy, azido, amino, halogen, alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, arylalkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl, and the like.

As used herein, the term "reacting" refers to the formation of a bond between two or more components to produce a compound. In some cases, the compound is isolated. In some cases, the compound is not isolated and is formed in situ. For example, a first component and a second component may react to form one reaction product comprising the first component and the second component joined by a covalent bond (e.g., a bond formed between a ligand and a metal, or a bond formed between two substrates in a metathesis reaction). That is, the term "reacting" does not refer to the interaction of solvents, catalysts, bases, ligands, or other materials which may serve to promote the occurrence of the reaction with the component(s).

As used herein, the term "organic group" refers to any group comprising at least one carbon-carbon bond and/or carbon-hydrogen bond. For example, organic groups include alkyl groups, aryl groups, acyl groups, and the like. In some cases, the organic group may comprise one or more heteroatoms, such as heteroalkyl or heteroaryl groups. The organic group may also include organometallic groups. Examples of groups that are not organic groups include —NO or —$N_2$. The organic groups may be optionally substituted, as described below.

The term "organometallic" is given its ordinary meaning in the art and refers to compositions comprising at least one metal atom bound to one or more than one organic ligand. In some cases, an organometallic compound may comprise a metal atom bound to at least one carbon atom.

The term "chiral" is given its ordinary meaning in the art and refers to a molecule that is not superimposable with its mirror image, wherein the resulting nonsuperimposable mirror images are known as "enantiomers" and are labeled as either an (R) enantiomer or an (S) enantiomer. Typically, chiral molecules lack a plane of symmetry.

The term "achiral" is given its ordinary meaning in the art and refers to a molecule that is superimposable with its mirror image. Typically, achiral molecules possess a plane of symmetry.

As used herein, a "nitrogen-containing ligand" may be any species comprising a nitrogen atom. In some cases, the nitrogen atom may bind to the metal atom. In some cases, the nitrogen-containing ligand may bind the metal center via a different atom. In some cases, the nitrogen atom may be a ring atom of a heteroaryl or heteroalkyl group. In some cases, the nitrogen atom may be a substituted amine group. It should be understood that, in catalyst precursors described herein, the nitrogen-containing ligand may have sufficiently ionic character to coordinate a metal center, such as a Mo or W metal center. Examples of nitrogen-containing ligands include, but are not limited to, pyrrolyl, pyrazolyl, pyridinyl, pyrazinyl, pyrimidinyl, imidazolyl, triazolyl, tetrazolyl, oxazolyl, isoxazolyl, thiazolyl, isothiazolyl, indolyl, indazolyl, carbazolyl, morpholinyl, piperidinyl, oxazinyl, substituted derivatives thereof, and the like. For example, the nitrogen-containing ligand may be pyrrolide or 2,5-dimethylpyrrolide. The nitrogen-containing ligand may be selected to interact with an oxygen-containing ligand such that the oxygen-containing ligand can readily replace the nitrogen-containing ligand in a precatalyst to generate a catalyst. In cases where the catalyst composition may be generated in situ in order to carry out a chemical reaction, the first, nitrogen-containing ligand may be selected such that, upon replacement by an oxygen-containing ligand, the nitrogen-containing ligands or protonated versions thereof do not interfere with the chemical reaction. In one embodiment, one of $R^4$ and $R^5$ is pyrrolyl. In some embodiments, the nitrogen-containing ligand may be chiral and the precatalyst may be provided as a racemic mixture or a purified stereoisomer.

As used herein, the term "oxygen-containing ligand" may be used to refer to ligands comprising at least one oxygen atom. In some cases, the oxygen atom binds to the metal atom. In other cases, the oxygen-containing ligand may bind the metal center via a different atom. The term "oxygen-containing ligand" may also describe ligand precursors comprising at least one hydroxyl group (e.g., a hydroxyl-containing ligand), wherein deprotonation of the hydroxyl group results in a negatively charged oxygen atom, which may coordinate to a metal atom. The oxygen-containing ligand may be a heteroaryl or heteroalkyl group comprising at least one oxygen ring atom. In some cases, the oxygen atom may be positioned on a substituent of an alkyl, heteroalkyl, aryl, or heteroaryl group. For example, the oxygen-containing ligand may be a hydroxy-substituted aryl group, wherein the hydroxyl group is deprotonated upon coordination to the metal center.

The phrase "protecting group" as used herein refers to temporary substituents which protect a potentially reactive functional group from undesired chemical transformations. Examples of such protecting groups include esters of carboxylic acids, sayl ethers of alcohols, and acetals and ketals of aldehydes and ketones, respectively. A "Si protecting group" is a protecting group comprising a Si atom, such as Si-trialkyl (e.g., trimethylsilyl, tributylsilyl, t-butyldimethylsilyl), Si-triaryl, Si-alkyl-diphenyl (e.g., t-butyldiphenylsilyl), or Si-aryl-dialkyl (e.g., Si-phenyldialkyl). Generally, a Si protecting group is attached to an oxygen atom. The field of protecting group chemistry has been reviewed (Greene, T. W.; Wuts, P. G. M. Protective Groups in Organic Synthesis, 2nd ed.; Wiley: N.Y., 1991). Such protecting groups (and associated protected moieties) are described in detail below.

Protected hydroxyl groups are well known in the art and include those described in detail in *Protecting Groups in Organic Synthesis*, T. W. Greene and P. G. M. Wuts, $3^{rd}$ edition, John Wiley & Sons, 1999, the entirety of which is incorporated herein by reference. Examples of suitably protected hydroxyl groups further include, but are not limited to, esters, carbonates, sulfonates allyl ethers, ethers, silyl ethers, alkyl ethers, arylalkyl ethers, and alkoxyalkyl ethers. Examples of suitable esters include formates, acetates, proprionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxy-crotonate, benzoate, p-benylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy) methyl, benzyloxymethyl, beta-(tri methylsilyl)ethoxymethyl, and tetrahydropyran-2-yl ether. Examples of suitable arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5]azadisilolidine and the like, and azide.

Protected aldehydes are well known in the art and include those described in detail in Greene (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

3. Description of Certain Embodiments of the Invention

In some embodiments, the present invention provides methods involving metathesis reactions and the formation of various products. As used herein, the term "metathesis reaction" is given its ordinary meaning in the art and refers to a chemical reaction in which two reacting species exchange partners in the presence of a transition-metal catalyst. In some cases, a byproduct of a metathesis reaction may be ethylene. A metathesis reaction may involve reaction between species comprising, for example, olefins and/or alkynes. Examples of different kinds of metathesis reactions include cross metathesis, ring-closing metathesis, ring-opening metathesis, acyclic diene metathesis, alkyne metathesis, enyne metathesis, and the like. The metathesis reaction may occur between two substrates which are not joined by a bond (e.g., intermolecular metathesis reaction) or between two portions of a single substrate (e.g., intramolecular metathesis reaction). In some embodiments, the method involves an intermolecular cross-metatheis reaction. In some cases, methods of the present invention allow for the formation of a metathesis product with high enantioselectivity and/or high ratio of Z:E isomers, as described herein.

In some cases, the method involves reacting a first species and a second species to form a product comprising a double bond, wherein the double bond comprises an atom of the first species and an atom of the second species. In some embodiments, the double bond may comprise a carbon atom from the first species and a carbon atom from the second species. The double bond produced may have a Z (e.g., cis) or E (e.g., trans) configuration. Those of ordinary skill in the art would understand the meaning of the terms "cis" or "Z" and "trans" or "E," as used within the context of the invention.

Some embodiments may provide the ability to selectively synthesize, via a metathesis reaction, products having a Z or E configuration about a double bond. In some cases, the method may provide the ability to synthesize compounds comprising a Z-disubstituted olefin. The methods described herein may include the use of reagents (e.g., substrates) which, under reaction conditions known in the art, may have been less reactive or essentially unreactive, i.e., may not have been able to form the reaction product. For example, previous metathesis methods may only be useful when applied to olefin substrates having a sterically small substituent, such as an alkyne or a cyano group, adjacent the olefin. However, methods described herein are useful when applied to a wide range of olefin substrates, including those having sterically large groups adjacent the olefin. In some embodiments, methods for synthesizing Z-disubstituted enol ethers are provided. In some embodiments, methods for synthesizing Z-disubstituted allylic amines are provided. In some embodiments, methods for synthesizing Z-disubstituted allylic amides are provided.

Figure 6:
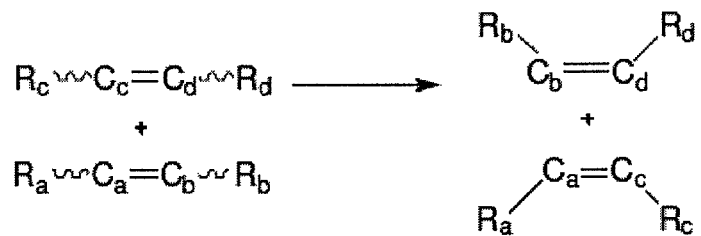
FIG. 6 shows an example of an intermolecular cross-metathesis reaction.

In some cases, a metathesis reaction may involve an intermolecular cross-metathesis reaction between a first species and a second species, each comprising an olefin, in the presence of a catalyst of the invention. As used herein, an "intermolecular cross-metathesis reaction" refers to a cross-metathesis reaction between a first species and a second species, wherein the first and second species are not attached to one another via a bond. For example, FIG. 6 illustrates an intermolecular cross-metathesis reaction where a first species comprising an olefin (e.g., $C_c=C_d$) and second species comprising an olefin ($C_a=C_b$) may be reacted to form a double bond. In some embodiments, the first and the second species each comprise a terminal olefin (e.g., a —CH=CH, group). In some embodiments, the method involves performing an intermolecular cross-metathesis reaction between a first species comprising a terminal olefin and a second species comprising an enol ether. In some embodiments, the method involves performing an intermolecular cross-metathesis reaction between a first species comprising a terminal olefin and a second species comprising an allylic amine. In some embodiments, the method involves performing an intermolecular cross-metathesis reaction between a first species comprising a terminal olefin and a second species comprising an allylic amide. In some cases, the iniermolecular cross-metathesis reaction may produce a product comprising a double bond in a Z:E ratio greater than at least about 1:1. Without wishing to be bound by theory, it is believed that such reactions are difficult to perform with high regioselectivity using previous methods, which often result in formation of olefin products having a more thermodynamically favored E configuration.

In some embodiments, the double bond may be produced in a Z:E ratio greater than about 1:1, greater than about 2:1, greater than about 3:1, greater than about 4:1, greater than about 5:1, greater than about 6: 1, greater than about 7:1, greater than about 8:1, greater than about 9:1, greater than about 95:5, greater than about 96:4, greater than about 97:3, greater than about 98:2, or, in some cases, greater than about 99:1, as determined using methods described herein (e.g., HPLC). In some cases, about 100% of the double bond produced in the metathesis reaction may have a Z configuration. The Z or cis selectivity may also be expressed as a percentage of product formed. In some cases, the product may be greater than about 50% Z, greater than about 60% Z, greater than about 70% Z, greater than about 80% Z, greater than about 90% Z, greater than about 95% Z, greater than about 96% Z, greater than about 97% Z, greater than about 98% Z, greater than about 99% Z, or, in some cases, greater than about 99.5% Z.

In some cases, the metathesis reaction may comprise reacting a first species comprises an olefin and a second species comprises an enol ether. The reaction may produce a product comprising a double bond, which may be formed in a Z:E ratio greater than about 4:1, or greater. As used herein, the term "enol ether" is given its ordinary meaning in the art and refers to an ether molecule comprising a carbon-carbon double bond adjacent the oxygen atom of the ether group.

In some embodiments, a provided method comprises reacting an enol ether of formula:

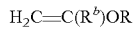

wherein:
R is —C(O)R$^a$, a hydroxyl protecting group, or an optionally substituted group selected from aliphatic, heteroaliphatic, aryl, heteroaryl, or heterocyclyl;
R$^a$ is hydrogen or optionally substituted group selected from aliphatic, heteroaliphatic, aryl, heteroaryl, or heterocyclyl; and
R$^b$ is hydrogen or optionally substituted aliphatic,
with an allylic amine of formula:

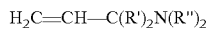

wherein:
each R' is independently hydrogen, —C(O)R$^a$, an amino protecting group, or an optionally substituted group selected from aliphatic, heteroaliphatic, aryl, heteroaryl, or heterocyclyl;
each R$^a$ is independently hydrogen or optionally substituted group selected from aliphatic, heteroaliphatic, aryl, heteroaryl, or heterocyclyl; and each R" is independently —C(O)R$^a$, an amino protecting group, or an optionally substituted group selected from aliphatic, heteroaliphatic, aryl, heteroaryl, or heterocyclyl, to form a cross-metathesis product with a Z:E ratio greater than 1:1.

As defined generally above, R is —C(O)R$^a$, a hydroxyl protecting group, or an optionally substituted group selected from aliphatic, heteroaliphatic, aryl, heteroaryl, or heterocyclyl. In some embodiments, R is an optionally substituted aliphatic group. In certaine embodiments, R is a hydroxyl protecting group.

In some embodiments, R is an alkyl group, such as n-alkyl, a substituted alkyl, an unsubstituted alkyl, a branched alkyl, or the like. In one set of embodiments, R is an n-alkyl group. In some cases the enol ether is butyl vinyl ether.

Figure 7:
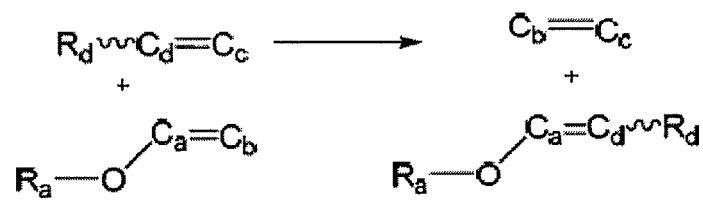
FIG. 7 shows an example of an intermolecular cross-metathesis reaction involving an enol ether.

In some embodiments, R is a substituted alkyl group. In certain embodiments, R is a propyl group substituted with a methoxy group and a silyl-protected hydroxy group (e.g., —O-tert-butyldimethylsilyloxy, "—OTBS"). In one set of embodiments, R is a substituted aryl group, such as 4-methoxyphenyl. Non-limiting examples of enol ethers include vinyl ethyl ether, cyclohexyl vinyl ether, 4-hydroxybutyl vinyl ether, n-butyl vinyl ether, isobutyl vinyl ether, n-propyl vinyl ether, and isopropyl vinyl ether. FIG. 7 shows an example of an intermolecular cross metathesis reaction between a enol ether and an olefin. In some cases, the product is produced with a high Z:E ratio (e.g., greater than about 4:1).

Figure 8:
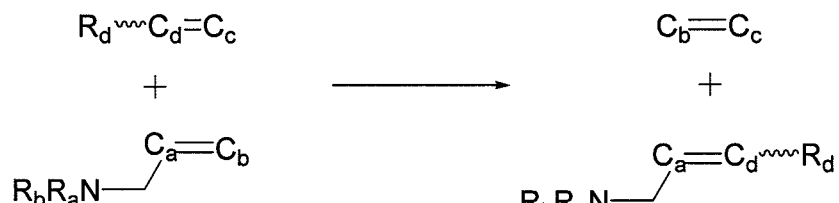
FIG. 8 shows an example of an intermolecular cross-metathesis reaction involving an allylic amine.

In some embodiments, R may be an alkyl group, such as n-alkyl, a substituted alkyl, an unsubstituted alkyl, a branched alkyl, or the like. In some embodiments, R' may be a substituted alkyl group, one R" may be hydrogen and another R" may be an amine protecting group, such as a Boc protecting group. In some cases, R' may be a substituted alkyl group and both R" groups may be joined to form a ring, e.g., may form a phthalimide group. In some embodiments, the substituted alkyl group may be a hydroxyl group protected by a benzyl group or a silyl group (e.g., TBS). FIG. 8 shows an example of an intermolecular cross metathesis reaction between an allylic amine and an olefin. In some cases, the product is produced with a high Z:E ratio (e.g., greater than about 4:1).

In certain embodiments, one or both of R' and R" is an amino protecting group.

In one set of embodiments, the reaction does not further comprise an acrylonitrile moiety. In another set of embodiments, the reaction does not further comprise an enyne moiety.

It will be appreciated that, in certain embodiments, each variable recited for the above method is as defined above and described in embodiments, herein, singly and in combination.

In some embodiments, a provided method comprises reacting an enol ether of formula:

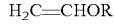

wherein:
R is —C(O)R$^a$, a hydroxyl protecting group, or an optionally substituted group selected from aliphatic, heteroaliphatic, aryl, heteroaryl, or heterocyclyl; and
R$^a$ is hydrogen or optionally substituted group selected from aliphatic, heteroaliphatic, aryl, heteroaryl, or heterocyclyl,
with an allylic amide of formula:

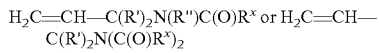

wherein:
each R' is independently hydrogen, —C(O)R$^a$, or an optionally substituted group selected from aliphatic, heteroaliphatic, aryl, heteroaryl, or heterocyclyl;
R" is an amino protecting group or an optionally substituted group selected from aliphatic, heteroaliphatic, aryl, heteroaryl, or heterocyclyl; and
each R$^x$ is independently hydrogen, or an optionally substituted group selected from aliphatic, heteroaliphatic, aryl, heteroaryl, or heterocyclyl,
to form a cross-metathesis product with a Z:E ratio greater than 1:1.

It will be appreciated that, in certain embodiments, each variable recited for the above method is as defined above and described in embodiments, herein, singly and in combination.

In some embodiments, a provided method comprises reacting terminal alkene of formula:

$$H_2C=C(R^y)R^z$$

wherein:
R$^y$ is a hydrogen or an optionally substituted group selected from aliphatic, heteroaliphatic, aryl, heteroaryl, or heterocyclyl; and
R$^z$ is an optionally substituted group selected from aliphatic, heteroaliphatic, aryl, heteroaryl, or heterocyclyl,
with an allylic amine of formula:

$$H_2C=CH-C(R')_2N(R")_2$$

wherein:
each R' is independently hydrogen, —C(O)R$^a$, an amino protecting group, or an optionally substituted group selected from aliphatic, heteroaliphatic, aryl, heteroaryl, or heterocyclyl;
each R$^a$ is independently hydrogen or optionally substituted group selected from aliphatic, heteroaliphatic, aryl, heteroaryl, or heterocyclyl; and
each R" is independently —C(O)R$^a$, an amino protecting group, or an optionally substituted group selected from aliphatic, heteroaliphatic, aryl, heteroaryl, or heterocyclyl,
to form a cross-metathesis product with a Z:E ratio greater than 1:1.

It will be appreciated that, in certain embodiments, each variable recited for the above method is as defined above and described in embodiments, herein, singly and in combination.

In some embodiments, a provided method comprises reacting terminal alkene of formula:

$$H_2C=C(R^y)R^z$$

wherein:
R$^y$ is a hydrogen or an optionally substituted group selected from aliphatic, heteroaliphatic, aryl, heteroaryl, or heterocyclyl; and
R$^x$ is an optionally substituted group selected from aliphatic, heteroaliphatic, aryl, heteroaryl, or heterocyclyl,
with an allylic amide of formula:

$$H_2C=CH-C(R')_2N(R")C(O)R^x \text{ or } H_2C=CH-C(R')_2N(C(O)R^x)_2$$

wherein:
each R' is independently hydrogen, —C(O)R$^a$, or an optionally substituted group selected from aliphatic, heteroaliphatic, aryl, heteroaryl, or heterocyclyl;
R" is an amino protecting group or an optionally substituted group selected from aliphatic, heteroaliphatic, aryl, heteroaryl, or heterocyclyl; and
each R$^x$ is independently hydrogen, or an optionally substituted group selected from aliphatic, heteroaliphatic, aryl, heteroaryl, or heterocyclyl,
to form a cross-metathesis product with a Z:E ratio greater than 1:1.

It will be appreciated that, in certain embodiments, each variable recited for the above method is as defined above and described in embodiments, herein, singly and in combination.

In some embodiments, a provided method comprises reacting terminal alkene of formula:

$$H_2C=C(R^y)R^z$$

wherein:
R$^y$ is a hydrogen or an optionally substituted group selected from aliphatic, heteroaliphatic, aryl, heteroaryl, or heterocyclyl; and
R$^z$ is an optionally substituted group selected from aliphatic, heteroaliphatic, aryl, heteroaryl, or heterocyclyl,
with an enol ether of formula:

$$H_2C=C(R^b)OR$$

wherein:
R is —C(O)R$^a$, a hydroxyl protecting group, or an optionally substituted group selected from aliphatic, heteroaliphatic, aryl, heteroaryl, or heterocyclyl;
R$^a$ is hydrogen or optionally substituted group selected from aliphatic, heteroaliphatic, aryl, heteroaryl, or heterocyclyl; and
R$^b$ is hydrogen or optionally substituted aliphatic,
to form a cross-metathesis product with a Z:E ratio greater than 1:1.

It will be appreciated that, in certain embodiments, each variable recited for the above method is as defined above and described in embodiments, herein, singly and in combination.

In certain embodiments, at least one R" is an amino protecting group. In some embodiments, the allylic amine comprises a phthalimide group (i.e., where R" are both an amino protecting group thereby forming a phthalimide group. In other embodiments, the allylic amine comprises a BOC protected amine (i.e., where R" is a t-butyloxycarbonyl amino protecting group).

In certain embodiments, R' is an optionally substituted aliphatic group. In some embodiments, R' is an alkyl group substituted with an optionally substituted hydroxyl group. In certain embodiments, the alkyl group is substituted with a silyl protected hydroxyl group.

In some embodiments, R' is an optionally substituted alkynyl group. In certain embodiments, R' comprises a protected alkynyl group. In some embodiments, R' comprises a silyl protected alkynyl group.

Methods described herein may also exhibit high conversion rates (i.e., % substrate converted to metathesis product). For example, the metathesis reaction may be performed with a conversion of at least about 50%, at least about 60%, at least about 70%, at least about 80%, at least about 90%, or, in some cases, at least about 98%.

In some cases, the method is performed in the presence of a catalyst, such as a metal complex. In some embodiments, the catalyst may be a metal complex comprising a stereogenic metal atom. Such metal complexes (e.g., catalysts) may be isolated, or may be formed in situ and utilized in a subsequent reaction (e.g. one-pot reaction).

In some embodiments, the metal complex is isolated as a Lewis base adduct. The terms "Lewis base" and "Lewis base adduct" are known in the art and refer to a chemical moiety capable of donating a pair of electrons to another chemical moiety. For example, the metal complex is combined with tetrahydrofuran (THF), wherein at least one THF molecules coordinate the metal center to form a Lewis base adduct. In some cases, the Lewis base adduct may be PMe$_3$. In some embodiments, the coordination of Lewis base molecules to the metal complex may produce a plane of symmetry with respect to the metal center. However, the stereogenic metal center may be reformed by facile removal of the Lewis base molecules. For example, the metal complex may be formed and stored as a Lewis base adduct, and may be "activated" in a subsequent reaction step to restore the original stereogenic metal center.

As used herein, the term "stereogenic metal atom" is given its ordinary meaning, and refers to a metal atom coordinated by at least two ligands (e.g., at least four ligands), wherein the ligands are arranged about the metal atom such that the overall structure (e.g., metal complex) lacks a plane of symmetry with respect to the metal atom. In some cases, the stereogenic metal atom may be coordinated by at least three ligands, at least four ligands, at least five ligands, at least six ligands, or more. In a particular embodiment, the stereogenic metal atom may be coordinated by four ligands. Metal complexes comprising a stereogenic metal center may provide sufficient space specificity at a reaction site of the metal complex, such that a molecular substrate having a plane of symmetry may be reacted at the reaction site to form a product that is free of a plane of symmetry. That is, the stereogenic metal center of the metal complex may impart sufficient shape specificity to induce stereogenicity effectively, producing a chiral, molecular product. Such metal complexes may exhibit improved catalytic activity and stereoselectivity, relative to previous systems, and undesired side reactions (e.g., dimerization or oligomerization of the metal complex) may be reduced.

Some embodiments of the invention provide a composition comprising a metal complex suitable for use in stereoselective cross-metathesis reactions described herein. In some cases, the metal complex comprises a stereogenic metal atom, and two or more ligands that bind the metal atom. In some embodiments, each ligand associated with the metal complex comprises an organic group. The ligands may be monodentate ligands, i.e., the ligands bind the stereogenic metal atom via one site of the ligand (e.g., a carbon atom or a heteroatom of the ligand). In some cases, a monodentate ligand may bind the metal center via a single bond or a multiple bond. In some cases, the metal complex comprises at least one ligand lacking a plane of symmetry. That is, at least one ligand bound to the stereogenic metal atom is a chiral ligand. In some cases, the metal complex comprises an oxygen-containing ligand, including chiral and/or achiral oxygen-containing ligands. In some cases, the metal complex comprises a nitrogen-containing ligand, including chiral and/or achiral nitrogen-containing ligands. For example, the ligand may be a chiral or achiral nitrogen heterocycle, such as a pyrrolide. In some cases, the metal atom may be bound to at least one carbon atom.

Some aspects of the invention can be realized with metal complexes comprising two or more ligands, wherein each ligand is a monodentate ligand, i.e., each ligand binds or coordinates the metal center via one coordination site of the metal only, or via one site of the ligand only. That is, in some embodiment, the metal complex does not comprise one or more bidentate, tridentate, quatradentate, etc., ligands. In certain embodiments, a metal complex comprises primarily monodentate ligands, as described herein, and may exhibit enhanced catalytic activity and stability relative to a similar complex comprising a bidentate or other multidentate ligand. For example, catalysts comprising only monodentate ligands may be prepared in high yields using the methods of the invention. Such ligands are described in detail below. Notwithstanding, in some embodiments, a metal complex comprises a bidentate ligand.

In some embodiments, the method comprises use of a metal complex in a diastereomeric ratio greater than 1:1. In some cases, the composition comprises the metal complex in a diastereomeric ratio greater than about 5:1, greater than about 7:1, greater than about 10:1, greater than about 20:1, or, in some cases, greater.

In some embodiments, a metal complex for use in a provided method is of formula I:

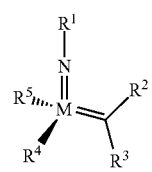

I wherein:
M is Mo or W;
$R^1$ is an optionally substituted group selected from aryl, heteroaryl, aliphatic, or heteroaliphatic;
each of $R^2$ and $R^3$ is independently hydrogen, or an optionally substituted group selected from aliphatic, heteroaliphatic, aryl, or heteroaryl;
$R^4$ is an optionally substituted group selected from —O-alkyl, —O-heteroalkyl, —O-aryl, —O-heteroaryl, —N(R″)-alkyl, —N(R″)-heteroalkyl, —N(R″)-aryl, or —N(R″)-heteroaryl;
each R″ is independently hydrogen, an amino protecting group, or an optionally substituted aliphatic; and
$R^5$ is halogen or an optionally substituted group selected from aryl, heteroaryl, aliphatic, heteroaliphatic, —O-alkyl, —O-heteroalkyl, —O-aryl, or —O-heteroaryl.

In some embodiments, the present invention provides the metal complex of formula I, wherein:
$R^2$ is hydrogen or an optionally substituted group selected from alkyl or aryl;
$R^3$ is alkyl, dialkyl amine, achiral alkoxide, or heteroaryl, optionally substituted;
$R^4$ is an optionally substituted chiral biaryloxy group; and
$R^5$ is halogen, a silylether group, or an optionally substituted group selected from alkyl, heteroalkyl, aryl, or heteroaryl.

In certain embodiments, the present invention provides the metal complex of formula I, wherein $R^4$ is an optionally substituted asymmetric —O-aryl group and $R^5$ is an optionally substituted heteroaryl group. In some embodiments, the present invention provides the metal complex of formula I, wherein $R^4$ is an optionally substituted asymmetrical —O-aryl group and $R^5$ is an optionally substituted —O-heteroaryl group. In some embodiments, $R^5$ is optionally substituted pyrrolyl.

In certain embodiments, $R^4$ is an optionally substituted —O-aliphatic group. In some embodiments, $R^4$ is a substituted —O-alkyl group. In certain embodiments, $R^4$ is an optionally substituted chiral —O-alkyl group.

In certain embodiments, $R^5$ is an optionally substituted —O-aliphatic group. In some embodiments, $R^5$ is a substituted —O-alkyl group.

In some embodiments, the present invention *vides the metal complex of formula I, wherein:
$R^1$ is aryl or alkyl, optionally substituted with one or more of $R^5$;

$R^2$ is hydrogen or an optionally substituted group selected from alkyl or aryl;

$R^3$ is an optionally substituted group selected from alkyl, dialkyl amine, achiral alkoxide, or heteroaryl;

$R^4$ is halogen, a silyl ether group, or an optionally substituted group selected from alkyl, heteroalkyl, aryl, or heteroaryl; and $R^5$ comprises an optionally substituted chiral biaryloxy group.

In some cases, $R^2$ is optionally substituted alkyl.

In some embodiments, the $R^4$ group of formula I is an oxygen-containing ligand lacking a plane of symmetry or nitrogen-containing ligand lacking a plane of symmetry; and $R^5$ is an optionally substituted group selected from alkyl, dialkyl amine, achiral alkoxide, or a group having the structure,

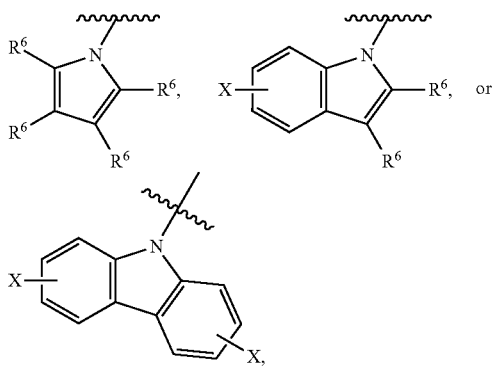

wherein:
each $R^6$ is independently hydrogen, an optionally substituted group selected from alkyl, heteroalkyl, aryl, heteroaryl, or an oxygen-containing ligand lacking a plane of symmetry or a nitrogen-containing ligand lacking a plane of symmetry; and X may be present or absent and is any non-interfering group.

As used herein, the term "non-interfering group," refers to any group (e.g., an organic group or permissible substituent to an organic group) which does not significantly effect or alter the properties (e.g., catalytic activity, solubility, etc.) of the compound. For example, a metal complex including a non-interfering group may exhibit at least 90% of the catalytic activity of an essentially identical metal complex lacking the non-interfering group. Non-limiting examples of non-interfering groups includes methyl, ethyl, protecting groups, and the like. In some embodiments, a non-interfering group is selected from monovalent substituents as defined and described herein.

In certain embodiments, $R^5$ is an optionally substituted group selected from

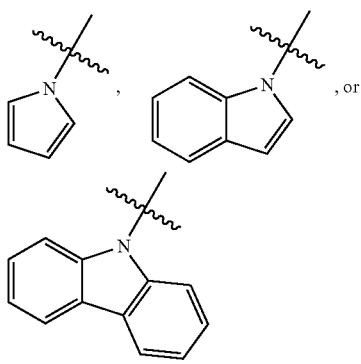

wherein each ⌇ represents the point of attachment to the metal.

In some cases, the metal complex may comprise one or more oxygen-containing ligands lacking a plane of symmetry or nitrogen-containing ligands lacking a plane of symmetry (i.e., asymmetric ligands). In some embodiments, such ligands may coordinate the metal atom via an oxygen atom (e.g., via a hydroxyl group), or other atom of the ligand. The oxygen-containing ligand may coordinate the metal atom via one site of the ligand, i.e., the ligand may be a monodentate ligand.

In one set of embodiments, a ligand may comprise two sites capable of binding the metal center, wherein a first site is bonded to a protecting group, or other group, that may reduce the ability of the first site to coordinate the metal, and the second site coordinates the metal center. For example, the ligand may be a BINOL derivative comprising two hydroxyl groups, wherein one hydroxyl group is bonded to a protecting group (e.g., a silyl protecting group) and another hydroxyl group coordinates the metal center.

In some embodiments, an asymmetric oxygen-containing ligand is of the following structure,

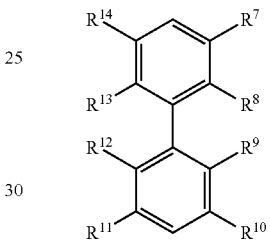

wherein:
$R^7$ is an optionally substituted group selected from aryl, heteroaryl, alkyl, or heteroalkyl;

$R^8$ is hydrogen, —OH, halogen, an optionally substituted group selected from aliphatic, heteroaliphatic, aryl, aryloxy (—O-aryl), heteroaryl, heteroaryloxy (—O-heteroaryl), acyl (—C(O)aliphatic), acyloxy (—OC(O)aliphatic), or —OPG;
or, together $R^7$ and $R^8$ are joined to form an optionally substituted partially unsaturated or aryl ring;

$R^9$ is —OH, —OPG, or an optionally substituted amino group;

$R^{10}$ is hydrogen, halogen, an optionally substituted group selected from aliphatic, heteroaliphatic, aryl, heteroaryl, or acyl;

each of $R^{11}$, $R^{12}$, $R^{13}$, and $R^{14}$ is independently aryl, heteroaryl, aliphatic, heteroaliphatic, or acyl, optionally substituted;
or, together $R^{11}$ and $R^{12}$ are joined to form an optionally substituted partially unsaturated or aryl ring;
or, together $R^{13}$ and $R^{14}$ are joined to form an optionally substituted partially unsaturated or aryl ring; and each PG is independently a hydroxyl protecting group.

The ring may be an aromatic or a non-aromatic ring. In some embodiments, the ring is a heterocycle. In some cases, the hydroxyl protecting group is a silyl protecting group. In some embodiments, the oxygen-containing ligand comprises a substituted alkyl group, such as $CF_3$.

In some embodiments, $R^8$ and $R^9$ are attached to the biaryl parent structure via a heteroatom, such as an oxygen atom. For example, $R^8$ and $R^9$ can be —OH, —O-aliphatic, aryloxy (—O-aryl), acyloxy (—C(O)aliphatic), or —OPG, where PG is a hydroxyl protecting group. In some cases, $R^8$ is —OPG and $R^9$ is —OH or an optionally substituted amino group.

Examples of asymmetric oxygen-containing ligands or asymmetric nitrogen-containing ligands include ligands shown in the Exemplification section, infra, as well as the following structures,
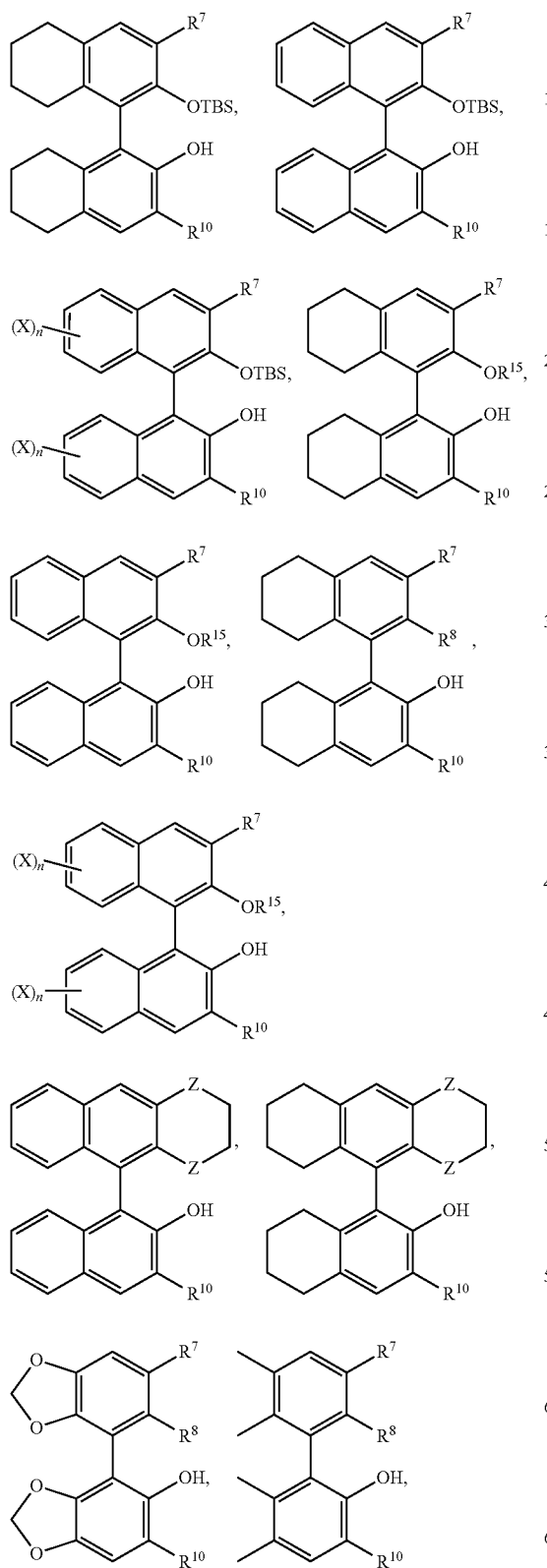
-continued
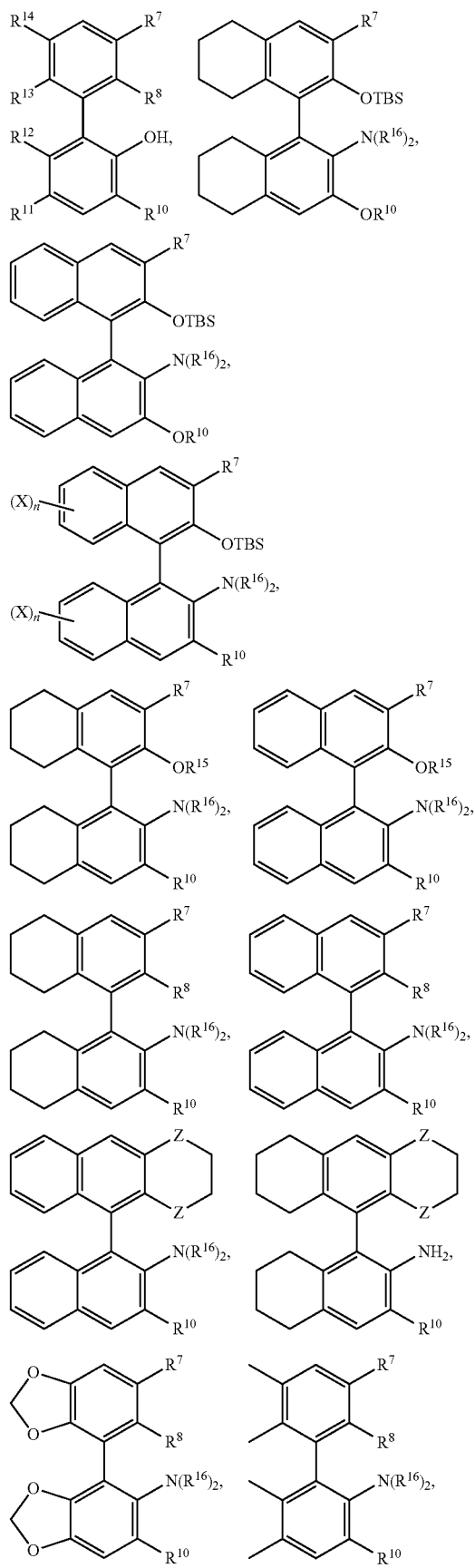

-continued

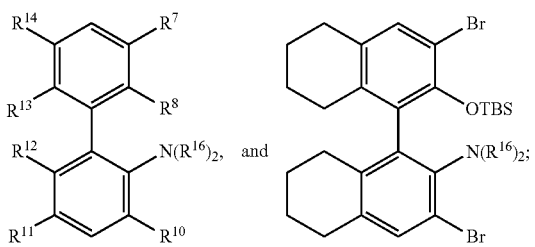 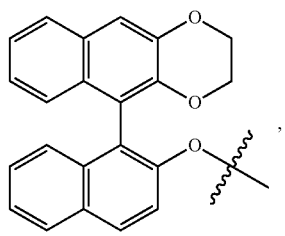

wherein:

each of $R^7$ and $R^8$ is independently hydrogen, halogen, an optionally substituted group selected from alkyl, alkoxy, aryl, $CF_3$, Si-tri-alkyl, Si-tri-aryl, Si-alkyl-diphenyl, Si-phenyl-dialkyl, or acyl (e.g., ester);

each $R^{10}$ is independently hydrogen, halogen, or an optionally substituted group selected from alkyl, heteroalkyl, aryl, heteroaryl, or acyl;

each of $R^{11}$, $R^{12}$, $R^{13}$, and $R^{14}$ is independently an optionally substituted group selected from aryl, heteroaryl, alkyl, heteroalkyl, or acyl;

or, together $R^{11}$ and $R^{12}$ are joined to form a ring, optionally substituted;

or, together $R^{13}$ and $R^{14}$ are joined to form a ring, optionally substituted;

$R^{15}$ is an optionally substituted group selected from alkyl, aryl, Si-trialkyl, Si-triaryl, Si-alkyldiphenyl, Si-phenyldialkyl, or acyl;

$R^{16}$ is hydrogen or an amine protecting group;

X is a non-interfering group;

each Z is independently $(CH_2)_m$, N, O, optionally substituted;

each n is independently 0-5; and each m is independently 1-4.

In some cases, each of $R^7$ and $R^{10}$ is the same or different and is halogen, methyl, t-butyl, $CF_3$, or aryl, optionally substituted.

In some embodiments, $R^4$ is an optionally substituted group selected from:

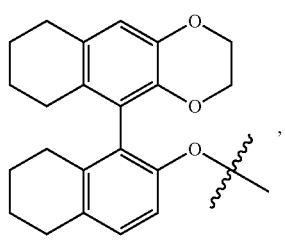

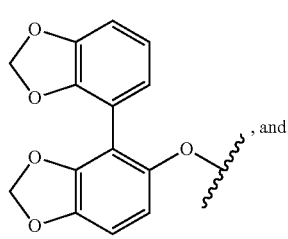

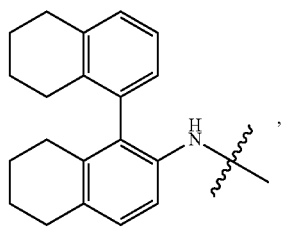 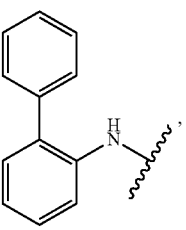

wherein each ⌇ represents the point of attachment to the metal.

In some embodiments, $R^4$ is an optionally substituted group selected from:

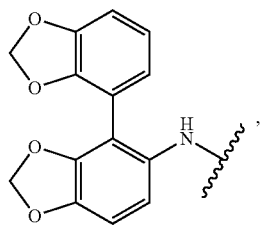

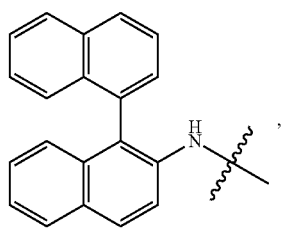

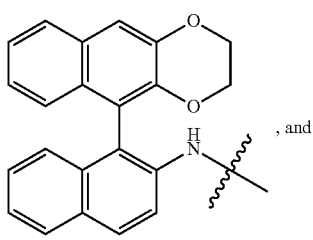

, and

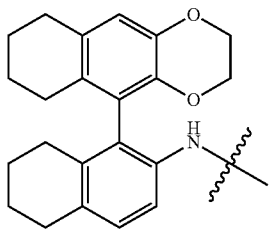

wherein each ⌇ represents the point of attachment to the metal.

In some embodiments, R⁴ is a silyl-protected BINOL derivative.

In some embodiments, $R^1$ is

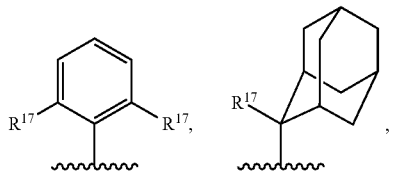

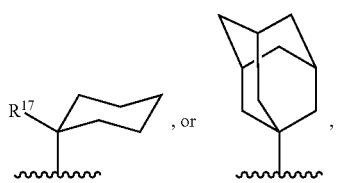

wherein each $R^{17}$ is independently hydrogen, halogen, —OPG, or an optionally substituted group selected from alkyl, heteroalkyl (e.g., alkoxy), aryl, or acyl, where PG is a hydroxyl protecting group. In some embodiments, each $R^{17}$ is a monovalent substituent as defined herein, supra.

In some embodiments, $R^1$ is

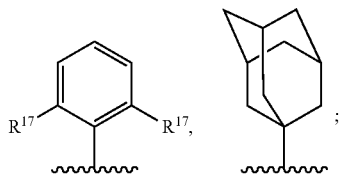

$R^2$ is $CMe_2Ph$ or $CMe_3$; and $R^4$ is an enantiomer of the following structure,

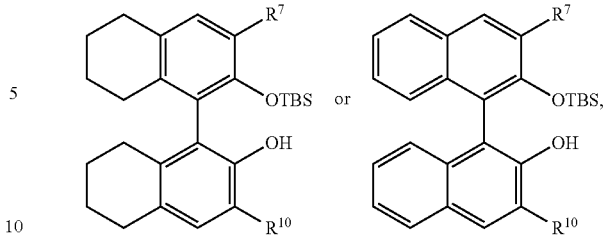

wherein each $R^{17}$ is the same or different and is halogen, methyl, t-butyl, $CF_3$, or aryl, optionally substituted. In some cases, $R^2$ is $CMe_2Ph$ or $CMe_3$, and $R^3$ is hydrogen.

In some embodiments, the metal complex comprises one of the following structures,

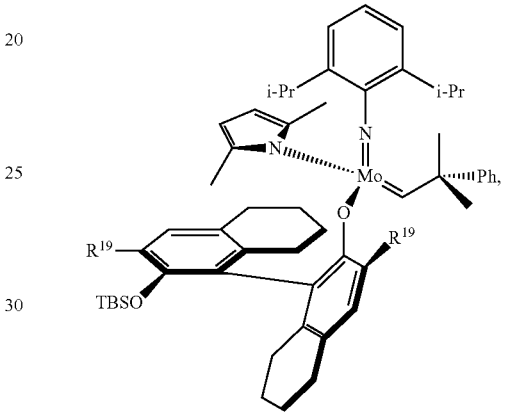

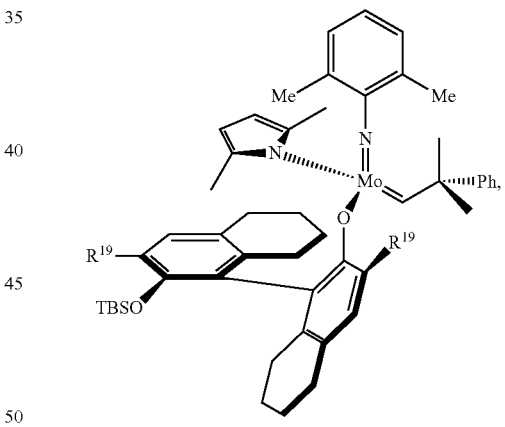

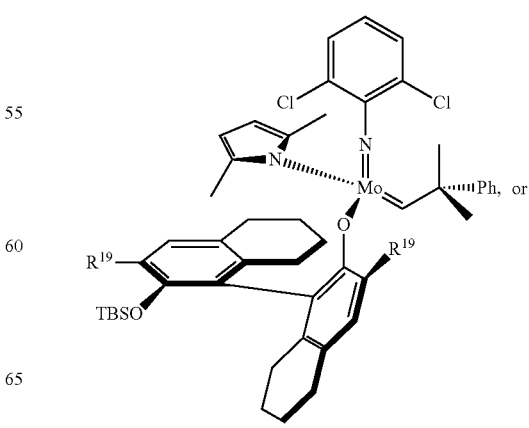

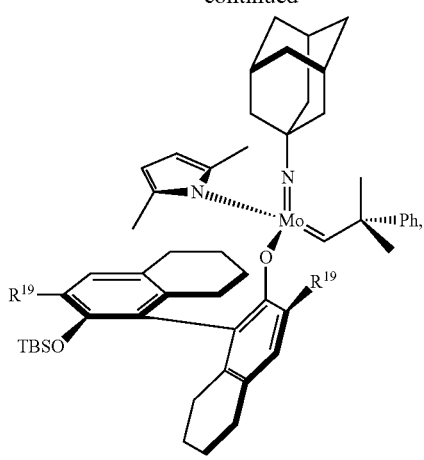
wherein each $R^{19}$ is independently F, Cl, Br, or I.
In certain embodiments, the metal complex comprises any one of the following structures:
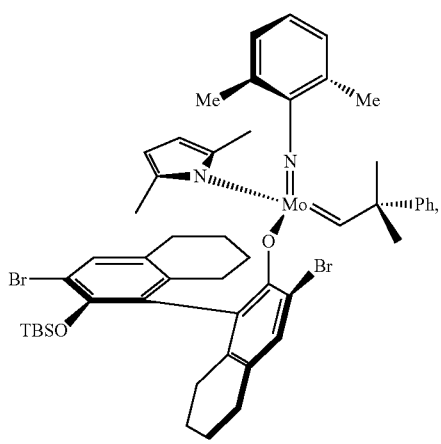
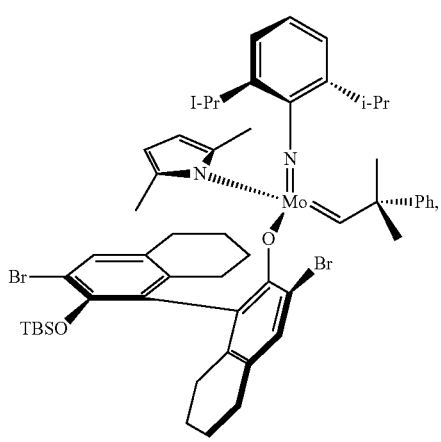
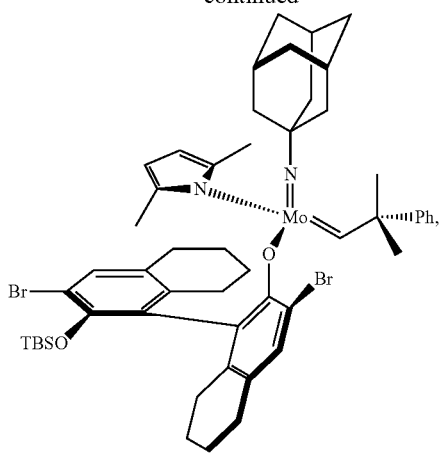
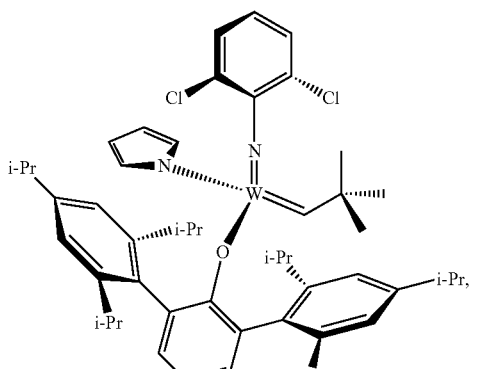
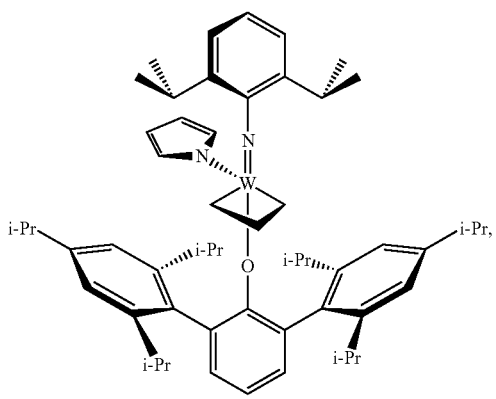
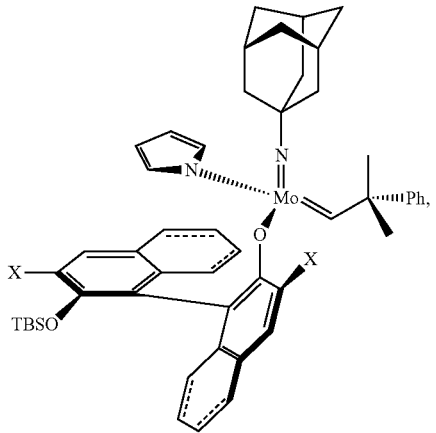
where each X is bromo or iodo,

31
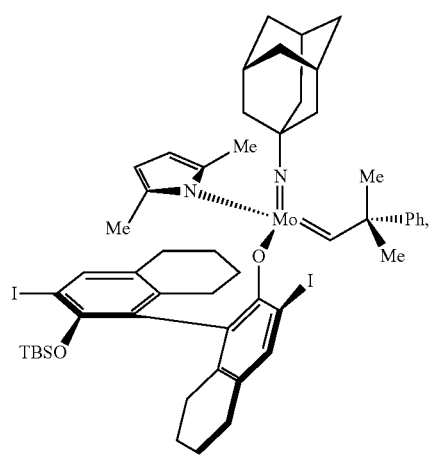
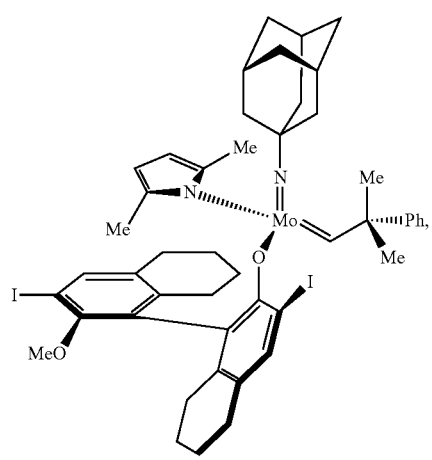
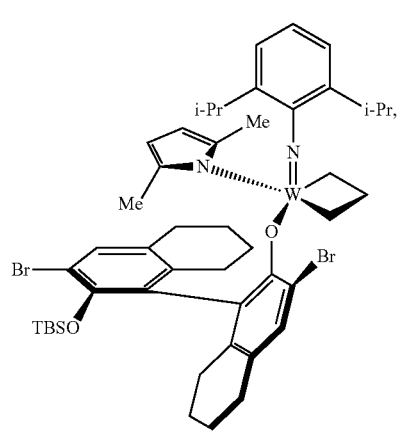
32
-continued
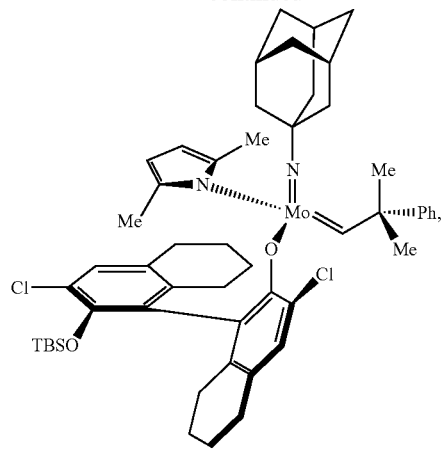
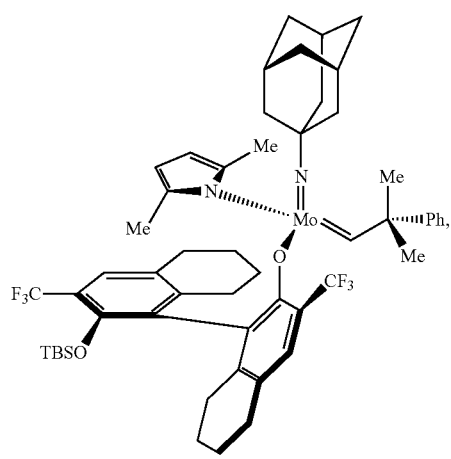
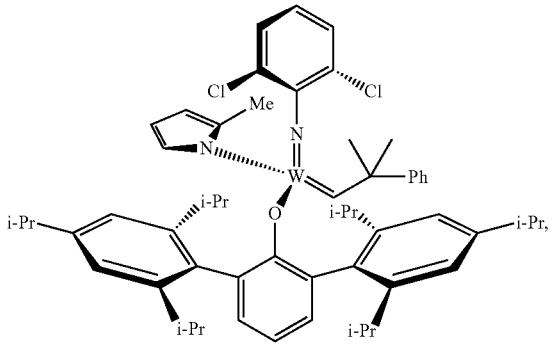

33
-continued
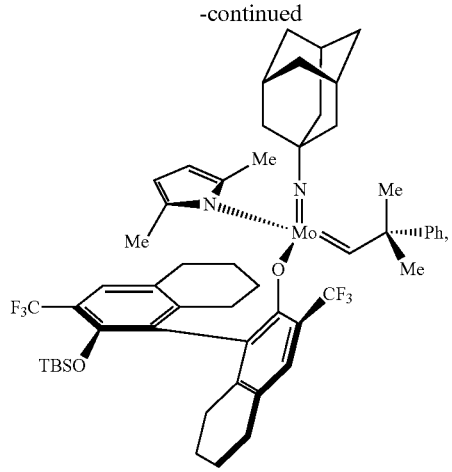
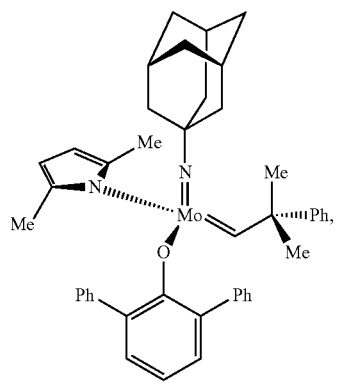
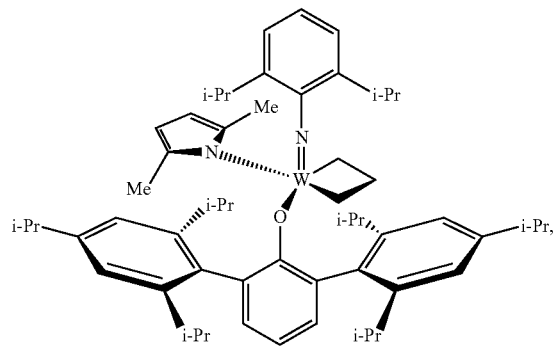
34
-continued
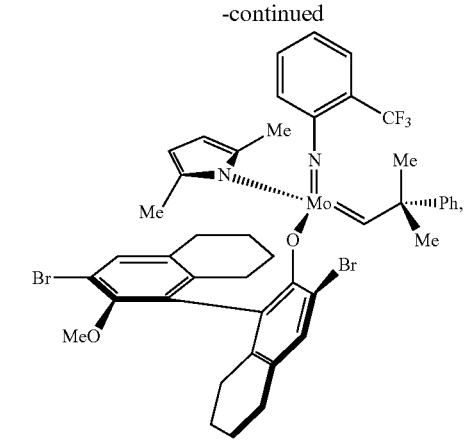
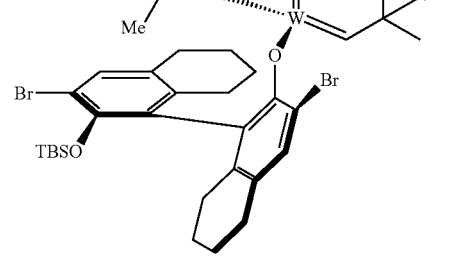
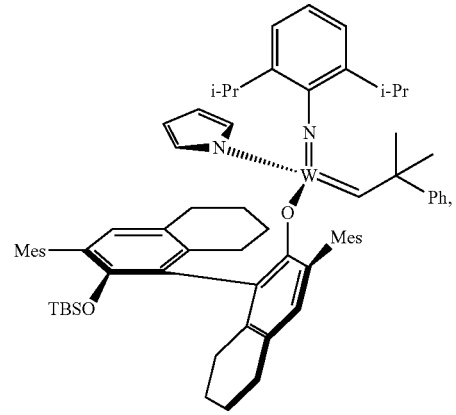
where Mes is 2,4,6-trimethylphenyl,

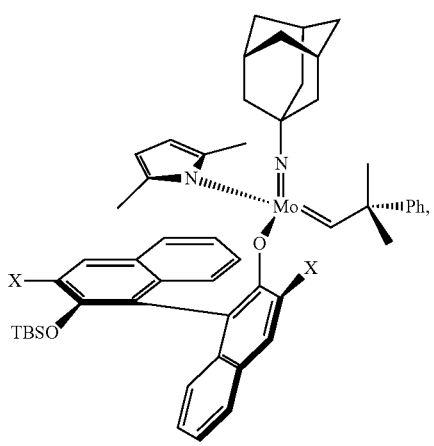

wherein each X is bromo, iodo, or —CF$_3$,

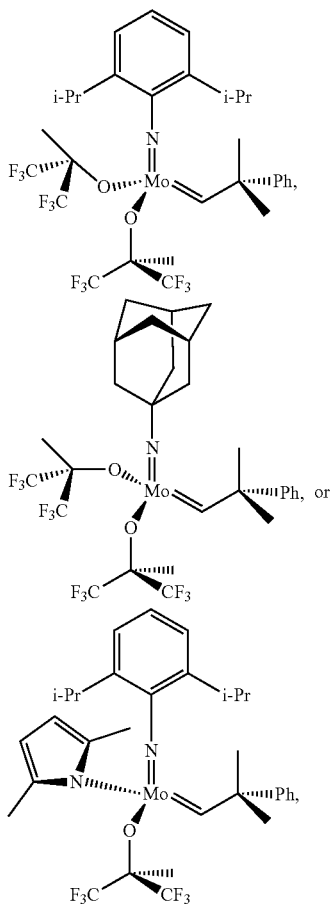

In some cases, R$^1$ may be linked to form a ring with R$^2$ or R$^3$. For example, the metal complex may comprise R$^1$ linked to form a ring with R$^2$ or R$^3$ prior to use as a catalyst, and, upon initiation of the catalyst in a metathesis reaction, the linkage between R$^1$ and R$^2$ or R$^3$ may be broken, therefore rendering each of the ligands monodentate. The ring may comprise any number of carbon atoms and/or heteroatoms. In some cases, the cyclic olefin may comprise more than one ring. The ring may comprise at least 4, at least 5, at least 6, at least 7, at least 8, at least 9, at least 10, or more, atoms.

It will be appreciated that, in certain embodiments, the present invention provides a method, as described herein, utilizing a catalyst of formula I, wherein each variable is as defined above and described in embodiments, herein, singly and in combination. In some embodiments, each variable is selected from moieties depicted in the Examples, infra.

In some embodiments, the present invention provides a catalyst of formula I, wherein each variable is as defined above and described in embodiments, herein, singly and in combination. In some embodiments, each variable is selected from moieties depicted in the Examples, infra.

In some embodiments, a provided method comprises reacting an enol ether of formula:

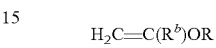

wherein:
R is —C(O)R$^a$, a hydroxyl protecting group, or an optionally substituted group selected from aliphatic, heteroaliphatic, aryl, heteroaryl, or heterocyclyl;
R$^a$ is hydrogen or optionally substituted group selected from aliphatic, heteroaliphatic, aryl, heteroaryl, or heterocyclyl; and
R$^b$ is hydrogen or optionally substituted aliphatic,
with an allylic amine of formula:

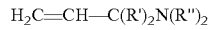

wherein:
each R' is independently hydrogen, —C(O)R$^a$, an amino protecting group, or an optionally substituted group selected from aliphatic, heteroaliphatic, aryl, heteroaryl, or heterocyclyl;
each R$^a$ is independently hydrogen or optionally substituted group selected from aliphatic, heteroaliphatic, aryl, heteroaryl, or heterocyclyl; and
each R" is independently —C(O)R$^a$, an amino protecting group, or an optionally substituted group selected from aliphatic, heteroaliphatic, aryl, heteroaryl, or heterocyclyl,
in the presence of a catalyst of formula I:

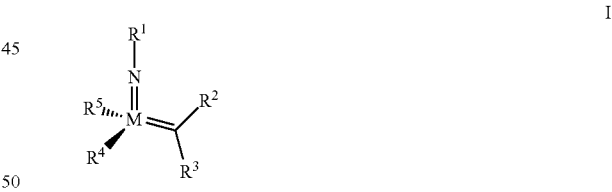

wherein:
M is Mo or W;
R$^1$ is an optionally substituted group selected from aryl, heteroaryl, aliphatic, or heteroaliphatic;
each of R$^2$ and R$^3$ is independently hydrogen, or an optionally substituted group selected from aliphatic, heteroaliphatic, aryl, or heteroaryl;
R$^4$ is an optionally substituted group selected from —O-alkyl, —O-heteroalkyl, —O-aryl, —O-heteroaryl, —N(R")-alkyl, —N(R")-heteroalkyl, —N(R")-aryl, or —N(R")-heteroaryl;
each R" is independently hydrogen, an amino protecting group, or an optionally substituted aliphatic; and
R$^5$ is halogen or an optionally substituted group selected from aryl, heteroaryl, aliphatic, heteroaliphatic, —O-alkyl, —O-heteroalkyl, —O-aryl, or —O-heteroaryl.

It will be appreciated that, in certain embodiments, each variable recited for the above method is as defined above and described in embodiments, herein, singly and in combination.

In some embodiments, a provided method comprises reacting an enol ether of formula:

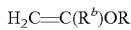

wherein:
R is —C(O)R$^a$, a hydroxyl protecting group, or an optionally substituted group selected from aliphatic, heteroaliphatic, aryl, heteroaryl, or heterocyclyl;
R$^a$ is hydrogen or optionally substituted group selected from aliphatic, heteroaliphatic, aryl, heteroaryl, or heterocyclyl; and
R$^b$ is hydrogen or optionally substituted aliphatic,
with an allylic amide of formula:

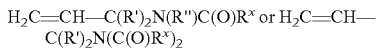

wherein:
each R' is independently hydrogen, —C(O)R$^a$, or an optionally substituted group selected from aliphatic, heteroaliphatic, aryl, heteroaryl, or heterocyclyl;
R" is an amino protecting group or an optionally substituted group selected from aliphatic, heteroaliphatic, aryl, heteroaryl, or heterocyclyl; and
each R$^x$ is independently hydrogen, or an optionally substituted group selected from aliphatic, heteroaliphatic, aryl, heteroaryl, or heterocyclyl,
in the presence of a catalyst of formula I:

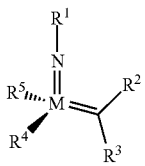

wherein:
M is Mo or W;
R$^1$ is an optionally substituted group selected from aryl, heteroaryl, aliphatic, or heteroaliphatic;
each of R$^2$ and R$^3$ is independently hydrogen, or an optionally substituted group selected from aliphatic, heteroaliphatic, aryl, or heteroaryl;
R$^4$ is an optionally substituted group selected from —O-alkyl, —O-heteroalkyl, —O-aryl, —O-heteroaryl, —N(R")-alkyl, —N(R")-heteroalkyl, —N(R")-aryl, or —N(R")-heteroaryl;
each R" is independently hydrogen, an amino protecting group, or an optionally substituted aliphatic; and
R$^5$ is halogen or an optionally substituted group selected from aryl, heteroaryl, aliphatic, heteroaliphatic, —O-alkyl, —O-heteroalkyl, —O-aryl, or —O-heteroary.
to form a cross-metathesis product with a Z:E ratio greater than 1:1.

It will be appreciated that, in certain embodiments, each variable recited for the above method is as defined above and described in embodiments, herein, singly and in combination.

In some embodiments, a provided method comprises reacting terminal alkene of formula:

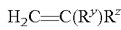

wherein:
R$^y$ is a hydrogen or an optionally substituted group selected from aliphatic, heteroaliphatic, aryl, heteroaryl, or heterocyclyl; and
R$^z$ is an optionally substituted group selected from aliphatic, heteroaliphatic, aryl, heteroaryl, or heterocyclyl,
with an allylic amine of formula:

wherein:
each R' is independently hydrogen, —C(O)R$^a$, an amino protecting group, or an optionally substituted group selected from aliphatic, heteroaliphatic, aryl, heteroaryl, or heterocyclyl;
each R$^a$ is independently hydrogen or optionally substituted group selected from aliphatic, heteroaliphatic, aryl, heteroaryl, or heterocyclyl; and
each R" is independently —C(O)R$^a$, an amino protecting group, or an optionally substituted group selected from aliphatic, heteroaliphatic, aryl, heteroaryl, or heterocyclyl,
in the presence of a catalyst of formula I:

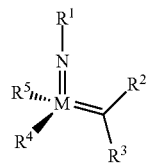

wherein:
M is Mo or W;
R$^1$ is an optionally substituted group selected from aryl, heteroaryl, aliphatic, or heteroaliphatic;
each of R$^2$ and R$^3$ is independently hydrogen, or an optionally substituted group selected from aliphatic, heteroaliphatic, aryl, or heteroaryl;
R$^4$ is an optionally substituted group selected from —O-alkyl, —O-heteroalkyl, —O-aryl, —O-heteroaryl, —N(R")-alkyl, —N(R")-heteroalkyl, —N(R")-aryl, or —N(R")-heteroaryl;
each R" is independently hydrogen, an amino protecting group, or an optionally substituted aliphatic; and
R$^5$ is halogen or an optionally substituted group selected from aryl, heteroaryl, aliphatic, heteroaliphatic, —O-alkyl, —O-heteroalkyl, —O-aryl, or —O-heteroary.
to form a cross-metathesis product with a Z:E ratio greater than 1:1.

It will be appreciated that, in certain embodiments, each variable recited for the above method is as defined above and described in embodiments, herein, singly and in combination.

In some embodiments, a provided method comprises reacting terminal alkene of formula:

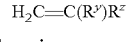

wherein:
R$^y$ is a hydrogen or an optionally substituted group selected from aliphatic, heteroaliphatic, aryl, heteroaryl, or heterocyclyl; and
R$^z$ is an optionally substituted group selected from aliphatic, heteroaliphatic, aryl, heteroaryl, or heterocyclyl,
with an allylic amide of formula:

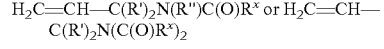

wherein:
each R' is independently hydrogen, —C(O)R$^a$, or an optionally substituted group selected from aliphatic, heteroaliphatic, aryl, heteroaryl, or heterocyclyl;
R$^a$ is hydrogen or optionally substituted group selected from aliphatic, heteroaliphatic, aryl, heteroaryl, or heterocyclyl, R" is an amino protecting group or an optionally substituted group selected from aliphatic, heteroaliphatic, aryl, heteroaryl, or heterocyclyl; and each $R^x$ is independently hydrogen, or an optionally substituted group selected from aliphatic, heteroaliphatic, aryl, heteroaryl, or heterocyclyl, in the presence of a catalyst of formula I:

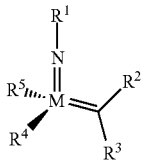

I wherein:

M is Mo or W;

$R^1$ is an optionally substituted group selected from aryl, heteroaryl, aliphatic, or heteroaliphatic;

each of $R^2$ and $R^3$ is independently hydrogen, or an optionally substituted group selected from aliphatic, heteroaliphatic, aryl, or heteroaryl;

$R^4$ is an optionally substituted group selected from —O-alkyl, —O-heteroalkyl, —O-aryl, —O-heteroaryl, —N(R")-alkyl, —N(R")-heteroalkyl, —N(R")-aryl, or —N(R")-heteroaryl;

each R" is independently hydrogen, an amino protecting group, or an optionally substituted aliphatic; and $R^5$ is halogen or an optionally substituted group selected from aryl, heteroaryl, aliphatic, heteroaliphatic, —O-alkyl, —O-heteroalkyl, —O-aryl, or —O-heteroaryl.

to form a cross-metathesis product with a Z:E ratio greater than 1:1.

It will be appreciated that, in certain embodiments, each variable recited for the above method is as defined above and described in embodiments, herein, singly and in combination.

In some embodiments, a provided method comprises reacting terminal alkene of formula:

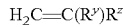

$$H_2C=C(R^y)R^z$$

wherein:

$R^y$ is a hydrogen or an optionally substituted group selected from aliphatic, heteroaliphatic, aryl, heteroaryl, or heterocyclyl; and $R^z$ is an optionally substituted group selected from aliphatic, heteroaliphatic, aryl, heteroaryl, or heterocyclyl, with an enol ether of formula:

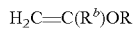

$$H_2C=C(R^b)OR$$

wherein:

R is —C(O)$R^a$, a hydroxyl protecting group, or an optionally substituted group selected from aliphatic, heteroaliphatic, aryl, heteroaryl, or heterocyclyl;

$R^a$ is hydrogen or optionally substituted group selected from aliphatic, heteroaliphatic, aryl, heteroaryl, or heterocyclyl; and $R^b$ is hydrogen or optionally substituted aliphatic, in the presence of a catalyst of formula I:

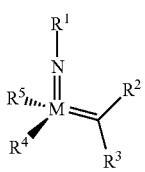

I wherein:

M is Mo or W;

$R^1$ is an optionally substituted group selected from aryl, heteroaryl, aliphatic, or heteroaliphatic;

each of $R^2$ and $R^3$ is independently hydrogen, or an optionally substituted group selected from aliphatic, heteroaliphatic, aryl, or heteroaryl;

$R^4$ is an optionally substituted group selected from —O-alkyl, —O-heteroalkyl, —O-aryl, —O-heteroaryl, —N(R")-alkyl, —N(R")-heteroalkyl, —N(R")-aryl, or —N(R")-heteroaryl;

each R" is independently hydrogen, an amino protecting group, or an optionally substituted aliphatic; and $R^5$ is halogen or an optionally substituted group selected from aryl, heteroaryl, aliphatic, heteroaliphatic, —O-alkyl, —O-heteroalkyl, —O-aryl, or —O-heteroaryl.

to form a cross-metathesis product with a Z:E ratio greater than 1:1.

It will be appreciated that, in certain embodiments, each variable recited for the above method is as defined above and described in embodiments, herein, singly and in combination.

The catalyst may be provided in the reaction mixture in a sub-stoichiometric amount (e.g., catalytic amount). In certain embodiments, that amount is in the range of about 0.01 to about 50 mol % with respect to the limiting reagent of the chemical reaction, depending upon which reagent is in stoichiometric excess. In some embodiments, the catalyst is present in less than or equal to about 40 mol % relative to the limiting reagent. In some embodiments, the catalyst is present in less than or equal to about 30 mol % relative to the limiting reagent. In some embodiments, the catalyst is present in less than about 20 mol %, less than about 10 mol %, less than about 5 mol %, less than about 2.5 mol %, less than about 1 mol %, less than about 0.5 mol %, or less, relative to the limiting reagent. In some embodiments, the catalyst is present in the range of about 2.5 mol % to about 5 mol %, relative to the limiting reagent. In the case where the molecular formula of the catalyst complex includes more than one metal, the amount of the catalyst complex used in the reaction may be adjusted accordingly.

As suitable, the catalysts employed in the present invention may involve the use of metals which can mediate a particular desired chemical reaction. In general, any transition metal (e.g., having d electrons) may be used to form the catalyst, e.g., a metal selected from one of Groups 3-12 of the periodic table or from the lanthanide series. However, in some embodiments, the metal may be selected from Groups 3-8, or, in some cases, from Groups 4-7. In some embodiments, the metal may be selected from Group 6. According to the conventions used herein, the term "Group 6" refers to the transition metal group comprising chromium, molybdenum, and tungsten. In some cases, the metal is molybdenum or tungsten. Without wishing to be bound by theory, it may be expected that catalysts comprising different metal atoms from the same group and comprising similar ligands will perform similarly because they are known to undergo similar reactions, such as metathesis reactions. However, altering the ligand framework may affect the catalyst performance by, for example, modifying reactivity and preventing undesirable side reactions. In a particular embodiment, the catalyst comprises molybdenum. Additionally, the present invention may also include the formation of heterogeneous catalysts containing forms of these elements (e.g., by immobilizing a Mo complex on an insoluble substrate, for example, silica).

In some embodiment, the metal catalyst comprising a stereogenic metal center comprises a reaction site that is of sufficient shape specificity, defined in part by the monodentate, oxygen-containing ligand, other monodentate ligand, and/or M=N—$R^1$ site, to cause a molecular substrate having a plane of symmetry to react with a M=C center at the reaction site in a specific manner to produce a catalytic olefin metathesis product that is free of a plane of symmetry, i.e., is chiral. The product may be formed in at least about 50% enantiomeric excess. In some cases, the product may be formed in at least about 60%, at least about 70%, at least about 80%, at least about 90%, at least about 95%, at least about 98%, or, in some cases, 99% enantiomeric excess. In some cases, the enantiomeric excess may be calculated based on the stereogenic center formed during the reaction. For example, in some cases, a reactant may comprise at least one stereogenic center and the product may comprise at least two stereogenic centers, i.e., including any stereogenic center(s) present prior to the reaction and any stereogenic center(s) formed during the reaction. While the products comprising more than one stereogenic center may comprise diastereomers, the enantiomeric excess of the product may be calculated based on the enantiomeric excess of a particular stereogenic center formed during the reaction. In some cases, the stereogenic metal center comprises a reaction site that is of sufficient shape specificity to produce, upon reaction, at least one double bond having a high Z:E ratio. In some embodiments, the Z:E ratio may be at least about 1:10, at least about 1:5, or at least about 1:2. In some embodiments, the Z:E ratio may be at least about 1:1, at least about 2:1, at least about 5:1, at least about 10:1, at least about 20:1, at least about 40:1, at least about 50:1, or greater.

A method to screen for monodentate, oxygen-containing ligands having sufficient shape specificity to produce a stereogenic product (e.g., high e.e., or high Z:E ratio) can involve providing a first solution comprising the catalyst and a second solution comprising the reactants. The solution(s) may comprise solvents which are compatible with the desired analysis (e.g., deuterated solvents for NMR techniques, polar/non-polar solvents for HPLC, GLC techniques, etc.). The first solution and the second solution may be combined under the appropriate conditions (e.g., temperature, time, agitation, etc.), and, after an appropriate reaction time has elapsed, the resulting solution may be analyzed using various methods known in the art. In some cases, the solution may be filtered prior to analysis. For analysis of Z:E ratio, yield, and/or enantiomeric excess, the product may be analyzed by NMR (e.g., $^1$H NMR, $^{13}$C NMR, etc.), HPLC, GLC, or the like. In some cases, more than one analysis may be performed. For example, a product may be analyzed by NMR, wherein the presence of different enantiomers may be indicated by NMR peaks characteristic of a particular enantiomer upon addition of a chiral shift reagent. In some embodiments, the product may be analyzed using chromatography (e.g., HPLC or GLC), where different enantiomers or diastereomers may exhibit distinct retention times. Those of ordinary skill in the art will be able to determine the appropriate method, or combination of methods, to utilize based upon the product to be analyzed.

In some embodiments, the shape specificity, imparted by a monodentate, oxygen-containing ligand and/or stereogenic metal center may be sufficient to allow a mixture of two enantiomeric reactants (e.g., olefins) to react with an M=C center of the reaction site at different rates. That is, a catalyst may be designed to have shape specificity sufficient to differentiate between enantiomers of a reactant by sterically interacting with one enantiomer almost exclusively or exclusively to achieve enantiomeric selectivity, that is, a preference for one enantiomer over the other. Enantiomeric selectivity by kinetic resolution involves reducing the steric interactions in the transition state of the reaction of the substrate at the catalyst such that the transition state involving one enantiomer is of lower energy than the transition state of the other enantiomer. In some cases, the term shape specificity refers to the shape of an M=C reaction site in the transition state, as formed by the surrounding ligands, such that upon reaction of the substrate with the metal compound, one enantiomer "fits into" the binding site with less steric interaction than the other enantiomer. The transition state energy is lower for the enantiomer with a better "fit" or shape specificity over the other.

Catalysts and catalyst precursors of the invention may comprise substituted imido groups (e.g., N—R$^1$). Without wishing to be bound by theory, the imido group may stabilize the organometallic compositions described herein by providing steric protection and/or reducing the potential for bimolecular decomposition. In some cases, R$^1$ may be selected to be sterically large or bulky, including phenyl groups, substituted phenyl groups (e.g., 2,6-disubstituted phenyls, 2,4,6-trisubstituted phenyls), polycyclic groups (e.g., adamantyl), or other sterically large groups. In some embodiments, R$^1$ may be 2,6-dialkylphenyl, such as 2,6-diisopropylphenyl. Catalysts and catalyst precursors of the invention may further comprise substituted alkylidene groups. The alkylidene groups may be mono-substituted or di-substituted with, for example, alkyl, heteroalkyl, aryl, or heteroaryl groups, optionally substituted. In some cases, the alkylidene may be mono-substituted with, for example, t-butyl, dimethylphenyl, or the like.

The combination of imido, alkoxide, and/or alkylidene ligands may be selected to suit a particular application. For example, in some cases, sterically large or sterically bulky ligands and/or ligand substituents may impart a higher degree of stability to a catalyst, while, in some cases, lowering the reactivity of the catalyst. In some cases, smaller ligands and/or substituents may generate more reactive catalysts that may have decreased stability. Those of ordinary skill in the art would be able to balance such factors and select the appropriate combination of ligands for catalysts of the invention.

In some cases, the present invention may also provide one-pot procedures involving the formation of a catalyst and subsequent use of the catalyst in a chemical reaction. The term "one-pot" reaction is known in the art and refers to a chemical reaction which can produce a product in one step which may otherwise have required a multiple-step synthesis, and/or a chemical reaction comprising a series of steps that may be performed in a single reaction vessel. One-pot procedures may eliminate the need for isolation (e.g., purification) of catalysts and/or intermediates, while reducing the number of synthetic steps and the production of waste materials (e.g., solvents, impurities). Additionally, the time and cost required to synthesize catalysts and/or other products may be reduced.

In some embodiments, a one-pot synthesis may comprise simultaneous addition of at least some components of the reaction to a single reaction chamber. In one embodiment, the one-pot synthesis may comprise sequential addition of various reagents to a single reaction chamber. For example, upon formation of the catalyst in a reaction vessel, a one-pot procedure may be performed, wherein the catalyst may be generated in situ from a precatalyst and may be subsequently employed in a chemical reaction, in the same reaction vessel. Those of ordinary skill in the art would be able to select the appropriate catalyst in combination with the chemical reaction to be performed. The ability to, in a single reaction vessel, generate a catalyst in situ and utilize the catalyst in a reaction, may facilitate the ability to screen a large number of catalysts for a particular reaction in a relatively short period of time. Also, additional purification steps may be eliminated, which may be useful in cases where the catalyst may be difficult to isolate. In some embodiments, it may be advantageous to form and then isolate the catalyst, prior to using the catalyst in a chemical reaction.

In some cases, the methods described herein may be performed in the absence of solvent (e.g., neat). In some cases, the methods may comprise one or more solvents. Examples of solvents that may be suitable for use in the invention include, but are not limited to, benzene, p-cresol, toluene, xylene, diethyl ether, glycol, diethyl ether, petroleum ether, hexane, cyclohexane, pentane, methylene chloride, chloroform, carbon tetrachloride, dioxane, tetrahydrofuran (THF), dimethyl sulfoxide, dimethylformamide, hexamethyl-phosphoric triamide, ethyl acetate, pyridine, triethylamine, picoline, mixtures thereof, or the like. In some embodiments, the solvent may be benzene, toluene, pentane, methylene chloride, or THF. In certain embodiments, the solvent is benzene.

In some embodiments, the method may also be performed under reduced pressure. This may be advantageous in cases where a volatile byproduct, such as ethylene, may be produced during the course of the metathesis reaction. For example, removal of the ethylene byproduct from the reaction vessel may advantageously shift the equilibrium of the metathesis reaction towards formation of the desired product. In some embodiments, the method is performed at a pressure of about less than 760 torr. In some embodiments, the method is performed at a pressure of about less than 700 torr. In some embodiments, the method is performed at a pressure of about less than 650 torr. In some embodiments, the method is performed at a pressure of about less than 600 torr. In some embodiments, the method is performed at a pressure of about less than 550 torr. In some embodiments, the method is performed at a pressure of about less than 500 torr. In some embodiments, the method is performed at a pressure of about less than 450 torr. In some embodiments, the method is performed at a pressure of about less than 400 torr. In some embodiments, the method is performed at a pressure of about less than 350 torr. In some embodiments, the method is performed at a pressure of about less than 300 torr. In some embodiments, the method is performed at a pressure of about less than 250 torr. In some embodiments, the method is performed at a pressure of about less than 200 torr. In some embodiments, the method is performed at a pressure of about less than 150 torr. In some embodiments, the method is performed at a pressure of about less than 100 torr. In some embodiments, the method is performed at a pressure of about less than 90 torr. In some embodiments, the method is performed at a pressure of about less than 80 torr. In some embodiments, the method is performed at a pressure of about less than 70 torr. In some embodiments, the method is performed at a pressure of about less than 60 torr. In some embodiments, the method is performed at a pressure of about less than 50 torr. In some embodiments, the method is performed at a pressure of about less than 40 torr. In some embodiments, the method is performed at a pressure of about less than 30 torr. In some embodiments, the method is performed at a pressure of about less than 20 torr. In some embodiments, the method is performed at a pressure of about 20 torr. In some embodiments, the method is performed at a pressure of about 19 torr. In some embodiments, the method is performed at a pressure of about 18 torr. In some embodiments, the method is performed at a pressure of about 17 torr. In some embodiments, the method is performed at a pressure of about 16 torr. In some embodiments, the method is performed at a pressure of about 15 torr. In some embodiments, the method is performed at a pressure of about 14 torr. In some embodiments, the method is performed at a pressure of about 13 torr. In some embodiments, the method is performed at a pressure of about 12 torr. In some embodiments, the method is performed at a pressure of about 11 torr. In some embodiments, the method is performed at a pressure of about 10 torr. In some embodiments, the method is performed at a pressure of about 10 torr. In some embodiments, the method is performed at a pressure of about 9 torr. In some embodiments, the method is performed at a pressure of about 8 torr. In some embodiments, the method is performed at a pressure of about 7 torr. In some embodiments, the method is performed at a pressure of about 6 torr. In some embodiments, the method is performed at a pressure of about 5 torr. In some embodiments, the method is performed at a pressure of about 4 torr. In some embodiments, the method is performed at a pressure of about 3 torr. In some embodiments, the method is performed at a pressure of about 2 torr. In some embodiments, the method is performed at a pressure of about 1 torr. In some embodiments, the method is performed at a pressure of less than about 1 torr.

In some embodiments, wherein the metathesis reaction involves an intermolecular cross-metathesis between a first species comprising an olefin and a second species comprising an olefin, the first species and second species are present in equimolar amounts. In some embodiments, wherein the metathesis reaction involves an intermolecular cross-metathesis between a first species comprising an olefin and a second species comprising an olefin, the first species and second species are not present in equimolar amounts. In certain embodiments, the first species and second species are present in a molar ratio of about 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, or 1:20. In certain embodiments, the first species and second species are present in a molar ratio of about 10:1. In certain embodiments, the first species and second species are present in a molar ratio of about 7:1. In certain embodiments, the first species and second species are present in a molar ratio of about 5:1. In certain embodiments, the first species and second species are present in a molar ratio of about 2:1. In certain embodiments, the first species and second species are present in a molar ratio of about 1:10. In certain embodiments, the first species and second species are present in a molar ratio of about 1:7. In certain embodiments, the first species and second species are present in a molar ratio of about 1:5. In certain embodiments, the first species and second species are present in a molar ratio of about 1:2.

In some cases, the oxygen-containing ligand may have a plane of symmetry, i.e., may be achiral. In some cases, the oxygen-containing ligand may lack a plane of symmetry, i.e., may be chiral, and may be provided as a racemic mixture or a purified stereoisomer. In some embodiments, the chiral, oxygen-containing ligand may be provided in at least about 80% optical purity, i.e., the oxygen-containing ligand sample contains about 90% of one enantiomer and about 10% of the other. In some embodiments, the chiral, oxygen-containing ligand may be at least about 90% optically pure, at least about 95% optically pure, or, in some cases, at least about 99% optically pure.

In some cases, the catalyst may comprise a monodentate, asymmetric oxygen-containing ligand (e.g., an alkoxide) such that, in conjunction with a stereogenic metal center, the combination of the monodentate, oxygen-containing ligand and the stereogenic metal center in part may confer shape specificity to a reaction site where the catalyst reacts with a reactant such as, for example, an olefin or an alkyne.

EXEMPLIFICATION

General: All reactions were carried out in oven-dried (135° C.) or flame-dried glassware under an inert atmosphere of dry $N_2$ unless otherwise stated. Alcohol D and substrates phenyl pent-4-enoate, dec-9-en-1-ynyltrimethylsilane, 12, 18, 1-methoxy-4-((oct-7-en-1-yloxy)methyl)benzene, tert-butyl allylcarbamate, N-allylphthalimide, and 21 were dried by azeotropic drying with $C_6H_6$ prior to use in reactions with Mo-based complexes (the numbering of compounds refers to those in the body of the text; other compounds are abbreviated by letters). Substrates allyl benzene, vinyl cyclohexane, and butyl vinyl ether were degassed by sparging with dry $N_2$ then dried by distillation from $CaH_2$. Substrates 1-decene, (allyloxy)triisopropylsilane, N-allylaniline, 8-bromooct-1-ene, I -octadecene, p-methoxyphenyl vinyl ether, and 1-hexadecene were dried by vacuum distillation from $CaH_2$. Alcohol $D^1$, and p-methoxyphenyl vinyl ether, 2 N-allylphthalimide[3], and 2,5-dioxopyrrolidin-1-yl hexacosanoate (23)[4] were synthesized according to previously reported procedures. Infrared (IR) spectra were recorded on a Bruker FTIR Alpha (ATR Mode) spectrometer, $v_{max}$ in $cm^{-1}$. Bands are characterized as strong (s), medium (m), or weak (w), broad (br). $^1$H NMR spectra were recorded on a Varian Unity INOVA 400 (400 MHz), or 500 (500 MHz) spectrometers. Chemical shifts are reported in ppm from tetramethylsilane with the solvent resonance resulting from incomplete deuteration as the internal reference ($CDCl_3$: δ 7.26, $C_6D_6$: δ 7.16). Data are reported as follows: chemical shift, integration, multiplicity (s=singlet, d=doublet, t=triplet, br=broad, m=multiplet, app=apparent), and coupling constants (Hz). Chemical shifts are reported in ppm from tetramethylsilane with the natural abundance of deuterium in the solvent as the internal reference ($CHCl_3$ in $CDCl_3$: δ 7.26). $^{13}$C NMR spectra were recorded on Varian Unity INOVA 400 (100 MHz) or 500 (125 MHz) spectrometers with complete proton decoupling. Chemical shifts are reported in ppm from tetramethylsilane with the solvent resonance resulting from incomplete deuteration as the internal reference ($CDCl_3$: δ 77.16, $C_6D_6$: δ 128.06). In the case of coupling to deuterium, the data are reported as follows: chemical shift, multiplicity (d=doublet, t=triplet), coupling constants (C-D, Hz). Enantiomer ratios were determined by HPLC (Chiral Technologies Chiralpak OJ-H column (4.6 mm×250 mm)) in comparison with authentic racemic materials. High-resolution mass spectrometry was performed on a Micromass LCT ESI-MS (positive mode) at the Boston College Mass Spectrometry Facility. Optical rotation values were recorded on a Rudolph Research Analytical Autopol IV polarimeter. Melting points were measured on a Thomas Hoover capillary melting point apparatus and are uncorrected.

Vacuum Pumps: Edwards RV8 two stage rotary vane pump generates a vacuum of 1.0 torr at point of connection to the reaction vessel. KNF Laboport N840.3FTP diaphragm vacuum pump generates a vacuum of 7.0 torr at point of connection to the reaction vessel.

Solvents: Solvents were purged with argon and purified under a positive pressure of dry argon by a modified Innovative Technologies purification system: diethyl ether (Aldrich), and dichloromethane (Aldrich) were passed through activated alumina columns; benzene (Aldrich), and pentane5 (J. T. Baker) were passed successively through activated Cu and alumina columns. Tetrahydrofuran (Aldrich) was distilled from sodium benzophenone ketyl. Ethanol (Aldrich) was distilled from $Mg/I_2$. Anhydrous acetonitrile (Aldrich) was used as received. N,N-Dimethylformamide (Acros; extra dry with molecular sieves) was used as received. Decalin (Aldrich) was distilled from sodium onto activated 4 Å molecular sieves.

Metal-based Complexes: Mo-bis(pyrrolide) complexes A, B and C were prepared according to published procedures. Mo complexes were handled in an $N_2$-filled dry box.

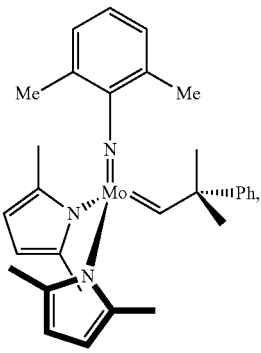

A

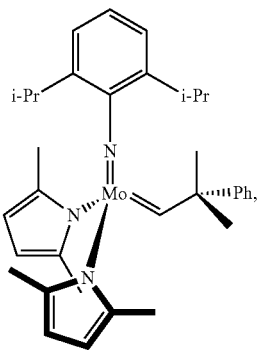

B

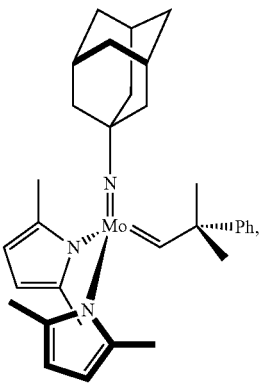

C

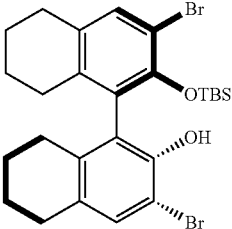

D

Reagents:

Allyl alcohol was purchased from Aldrich and used as received.

N-Allylaniline was purchased from Aldrich and distilled from $CaH_2$ prior to use.

Allyl bromide was purchased from Aldrich and vacuum distilled from $CaH_2$ prior to use.

Allyl benzene was purchased from Aldrich, sparged with dry $N_2$ and distilled from $CaH_2$ prior to use.

N-allyl-tert-butylcarbamate was purchased from Aldrich and purified by silica gel chromatography (10% ethyl acetate in hexanes) prior to use.

$d_6$-Benzene was purchased from Cambridge Isotope Laboratories and distilled from Na into activated 4 Å molecular sieves prior to use.

Benzoyl chloride was purchased from Aldrich and vacuum distilled neat prior to use.

8-Bromooct-1-ene was purchased from Aldrich and vacuum distilled from $CaH_2$ prior to use.

tert-Butyldimethylsilyl chloride was purchased from Oakwood and used as received.

n-Butyl lithium (15% in hexanes) was purchased from Strem and titrated with s-butanol (1,10-phenanthroline as indicator) prior to use.

Bis(pinacolato)diboron was purchased from Frontier Scientific, Inc., recrystallized from npentane, and dried at 60° C. under vacuum prior to use.

Butyl vinyl ether was purchased from Acros, sparged with dry $N_2$ and distilled from $CaH_2$ prior to use.

Carbon tetrabromide was purchased from Aldrich and used as received.

Cerotic acid was purchased from TCI and used as received.

Copper(I) chloride >99.999% was purchased from Strem and used as received.

1-Decene was purchased from Aldrich and vacuum distilled from $CaH_2$ prior to use.

4-(Dimethylamino)pyridine was purchased from Advanced ChemTech and used as received.

4,7-Diphenylphenanthroline was purchased from Aldrich and used as received.

Di-tert-butyl dicarbonate was purchased from Advanced ChemTech and used as received.

Ethylenediamine was purchased from Aldrich and distilled over $CaH_2$ prior to use.

1-Hexadecene was purchased from Alfa Aesar and vacuum distilled from $CaH_2$ prior to use.

Hydrogen peroxide 35 wt % aqueous solution was purchased from Aldrich and used as received.

Methanol was purchased from Aldrich and distilled from $Mg/I_2$ prior to use.

p-Methoxybenzyl chloride was purchased from Aldrich and used as received.

N-Methyl morpholine N-oxide (NMO) was purchased from Aldrich and used as received.

1-Octadecene was purchased from Aldrich and vacuum distilled from $CaH_2$ prior to use.

7-Octen-1-ol was purchased from TCI and used as received.

Osmium tetroxide was purchased as a solid from Aldrich and an aqueous solution was prepared from deionized water.

Palladium trifluoroacetate was purchased from Strem and used as received.

Palladium hydroxide on carbon was purchased from Aldrich and used as received.

(R)—N-Phthaloyl-2-aminobut-3-en-1-ol was synthesized according to a literature procedure,[7] and can also be purchased from Acros.

Potassium carbonate was purchased from Fisher and used as received.

Sodium tert-butoxide was purchased from Strem and used as received.

Sodium hydride (40% wt/wt suspension in mineral oil) was purchased from Strem and used as received.

Sodium hydroxide was purchased from Fisher and used as received.

D-2,3,4,6-tetra-O-benzylgalactose (F) was purchased from Aldrich and used as received.

Tetrabutylammonium fluoride 1 M in THF was purchased from Aldrich and used as received.

Triethylamine was purchased from Aldrich and distilled from $CaH_2$ prior to use.

Trifluoroacetic acid was purchased from Acros and used as received.

Triisopropylsilyl chloride was purchased from Aldrich and used as received.

Trimethylsilylacetylene was purchased from TCI and distilled over $CaH_2$ prior to use.

Triphenylphosphine was purchased from Aldrich and recrystallized from boiling hexanes prior to use.

Vinyl cyclohexane was purchased from Aldrich, sparged with dry $N_2$ and distilled from $CaH_2$ prior to use.

Example 1

Stereoselective In Situ-Generation of Monoaryloxide Complexes 1a-b and 2.

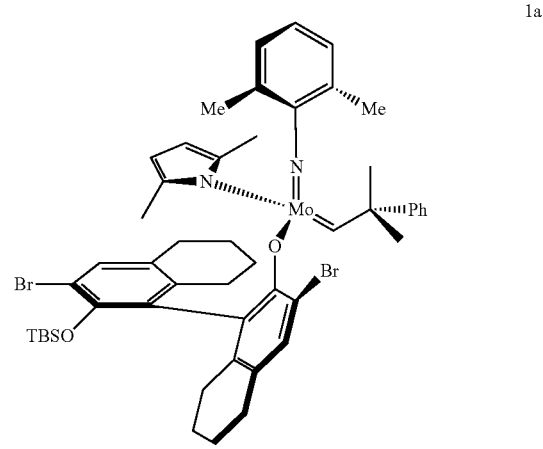

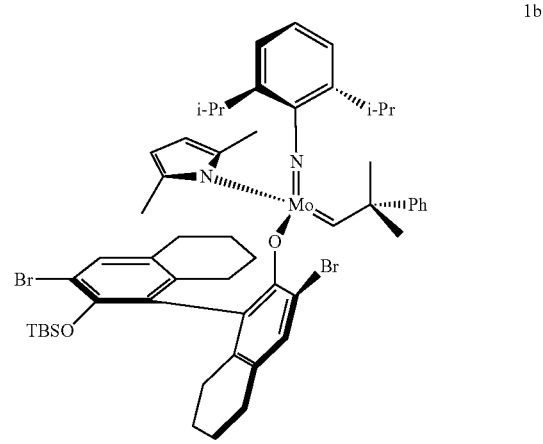

-continued

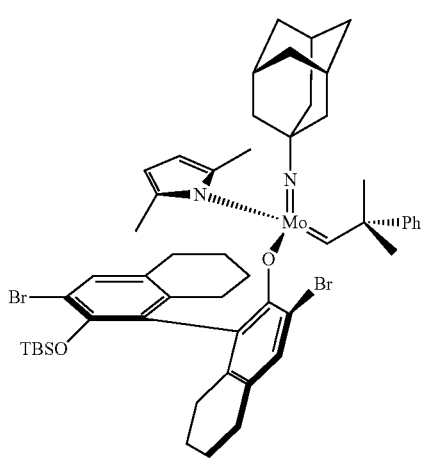

2

General Procedure: A 4-mL vial containing a magnetic stir bar was charged with Mo bispyrrolide A (5.70 mg, 10.6 μmol), alcohol D (5.90 mg, 10.6 μmol), and $C_6D_6$ (500 μL) in an $N_2$-filled glovebox. The vial was tightly capped and the mixture was allowed to stir for 1 h, after which it was transferred to a screw-cap NMR tube by a pipette. The NMR tube was tightly capped and sealed with Teflon tape. For in situ-generated complexes, only the diagnostic signals of the α-carbon of the syn-alkylidenes are reported. 1a: $^1$H NMR (400 MHz, $C_6D_6$): δ 13.02 (1H, s), 12.96 (1H, s); d.r.=1:8.8.

Representative Procedure for in situ-Generation of Complex 1a: In an $N_2$-filled glovebox, a 4-mL vial containing a magnetic stir bar was charged with Mo bis-pyrrolide A (20.0 mg, 37.2 μmol), alcohol D (21.1 mg, 37.2 μmol), and $C_6H_6$ (372 μL, 0.10 M); the mixture became brilliantly orange. The vial was capped and the solution was allowed to stir for 1 h at 22° C. The catalyst solution was transferred to the mixture by a syringe (dried at 65° C.).

Scheme 1.

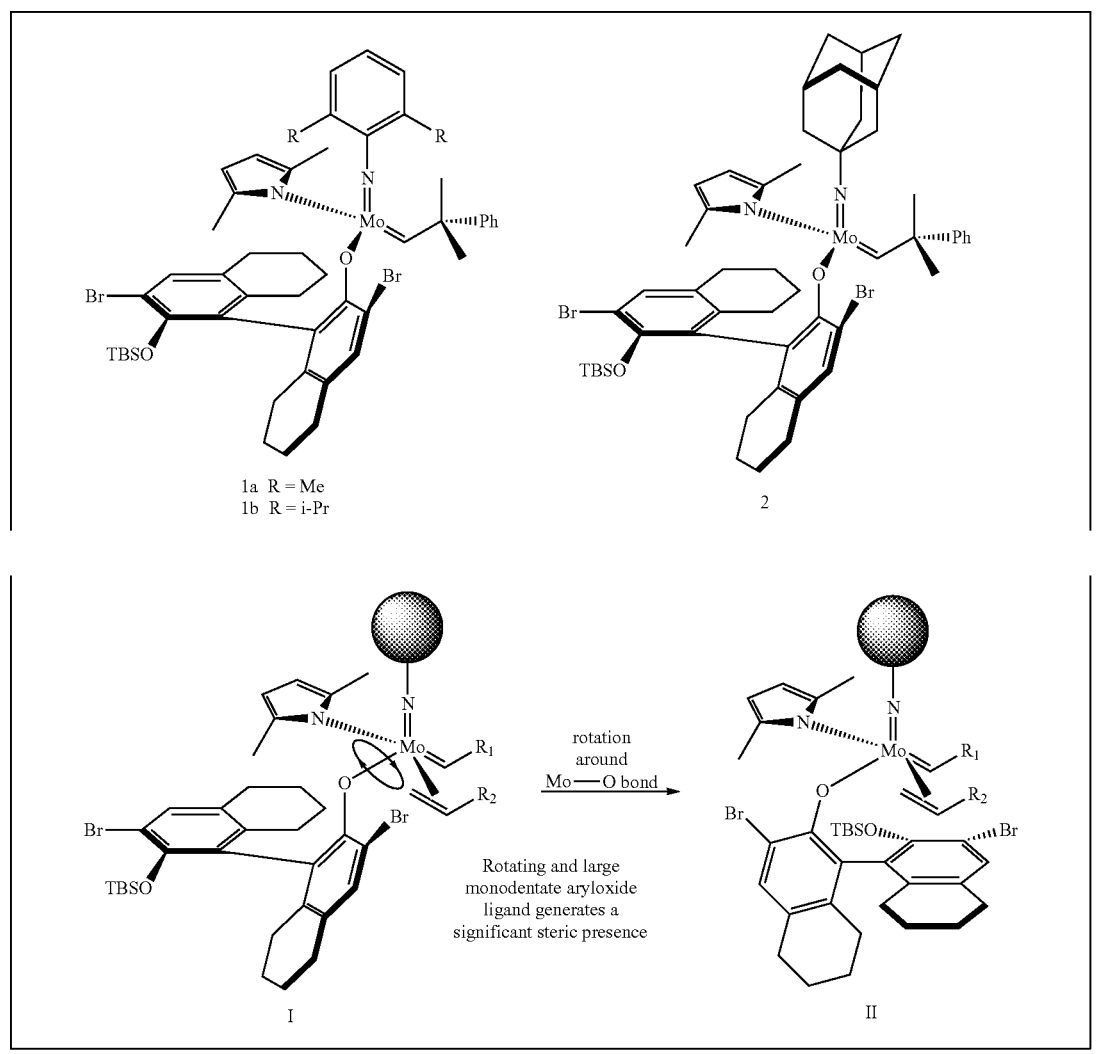

-continued

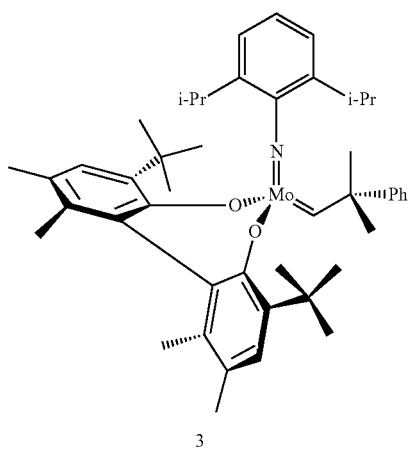

3

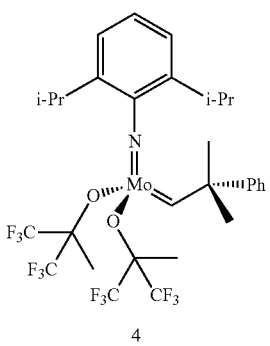

4

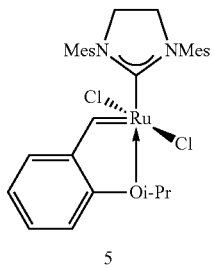

5

Example 2

Catalytic Cross-Metathesis of Enol Ether 6 and Alkene 7 with Various Catalysts

TABLE 1

Catalytic CM of Enol Ether 6 and Alkene 7 with Various Catalysts[a]

| entry | complex | 6:7 | time; conv (%)[b] | yield (%)[c] | Z:E[d] |
|---|---|---|---|---|---|
| 1 | 1a | 10:1 | 2 h; 85 | 73 | 98:2 |
| 2 | 1b | 10:1 | 2 h; 47 | nd | >98:2 |
| 3 | 2 | 10:1 | 2 h; 37 | nd | >98:2 |
| 4 | 3 | 10:1 | 2 h; <2 | — | — |
| 5 | 4 | 10:1 | 10 min; 80 | nd | 47.5:52.5 |
| 6 | 5 | 10:1 | 24 h; <2 | — | — |

[a]Reactions performed under $N_2$ atm.
[b]Values determined by analysis of 400 MHz $^1$H NMR spectra of unpurified mixtures.
[c]Yields of isolated products after purification (±5%).
[d]Values determined by $^1$H NMR analysis.

Representative Procedure for Catalytic Z-Selective Enol Ether Cross-Metathesis with Stereogenic-at-Mo Complexes: In an N2-filled dry box, a 20-mL vial equipped with a magnetic stir bar was charged with substrate. A separate 2-mL vial was charged with enol ether and in situ-generated Mo complex in $C_6H_6$. The resulting solution was allowed to mix for approximately 1 min and then transferred to the vial containing the substrate by syringe. The resulting solution was allowed to stir for the required period of time. The vessel was removed from the dry box and the reaction quenched by the addition of benchtop $Et_2O$ (~1 mL). The mixture was concentrated in vacuo (% conversion and diastereoselectivity determined by 400 MHz $^1$H NMR analysis). Purification was performed by neutral alumina or silica gel chromatography. Results reported are averages of at least two independent runs, and the reactions reported below are representative of a single run.

Designing an efficient Z-selective cross metathesis is significantly more challenging for a number of reasons. In a homocoupling, only one alkene is involved and no more than two stereoisomeric olefins can be formed; in contrast, there are two different substrates and up to six products can be generated in a cross metathesis. In the case of a catalytic ROCM, a strained cyclic alkene and a terminal olefin, reluctant to undergo homocoupling (e.g., a styrene), are selected as substrates so that the course of the catalytic process can be controlled in favor of the ROCM product. Transformations are therefore carefully crafted such that the alkylidene derived from the terminal alkene favors association with the cyclic olefin (vs. another molecule of the same type) in the ring-opening stage, generating a new Mo complex that prefers to react with a sterically less demanding terminal alkene (cross metathesis stage). The possibility of a transformation between the alkylidene generated through ring-opening and another strained—but more hindered—cyclic alkene is thus discouraged (i.e., minimal homocoupling or oligomerization). Such deliberate orchestration is not feasible with catalytic cross metathesis, where both alkenes are mono-substituted and manipulation of ring strain is not an option.

First, the ability of stereogenic-at-Mo complexes to promote cross metathesis reactions of an enol ether was evaluated; such transformations, E or Z selective, have not, to our knowledge, been previously reported. In the presence of 2.5 mol % 1a, cross metathesis between 6 and 7 (Table 1, entry 1) proceeded to 85% conversion to afford disubstituted enol ether 8a in 98% Z selectivity and 73% yield. With 1b, bearing a sterically more demanding 2,6-di-i-propyl-arylimido unit, the reaction was completely Z-selective (>98% Z) but 47% conversion is achieved within the same time span. When alkylidene 2 was used, reaction proceeded to 37% conversion and >98% Z-8a was generated; further transformation was not observed after six hours. As illustrated in Table 1 (entries 4-6), bis(aryloxide) 3 and Ru carbene 5 did not promote product formation and achiral Mo complex 4 catalyzed a non-selective cross metathesis (47.5% Z). Thus, stereogenic-at-Mo complexes prove to be uniquely effective. Moreover, in this application, although 1b or the less hindered 2 afford exceptional stereoselectivity, neither complex delivers the efficiency of 1a. The 2,5-dimethylphenylimido 1a offers the best balance in activity and stereoselectivity. Such performance variations may be observed because catalyst turnover is slower with the more sizeable 1b and the methylidene of the relatively unhindered 2 (cf. alkylidene I in Scheme 1 with $R_1$=H might suffer from a shorter life span). Consistent with the above scenario, 82% 8a is formed when cross metathesis with 1b is allowed to continue for 16 hours, whereas conversion with 2 after 10 minutes or two hours is nearly identical (~38%). There are several reasons for use of excess enol ether (6) in the abovementioned reactions. Cross metathesis generates a Mo-methylidene; this unhindered alkylidene can readily react with the Z-alkene product, reverse cross metathesis, cause equilibration and lower stereoselectivity. An enol ether reacts with a methylidene complex to circumvent diminution in Z-selectivity; the more stable alkoxy-substituted alkylidene thus generated (I in Scheme 1 with $R_1$=On-Bu) can undergo productive cross metathesis, giving rise to longer catalyst lifetime and improved turnover numbers. Furthermore, generation of the aforementioned alkoxy- or aryloxy-containing alkylidene means less of the alkyl-substituted derivative is formed, leading to a reduction in homocoupling of the aliphatic olefin. Due to electronic factors, reaction of an enol ether-derived alkylidene with another O-substituted alkene is disfavored.

Example 3

Catalytic Cross-Metathesis of Enol Ether 6 with Complex 1a

TABLE 2

Catalytic CM of Enol Ether 6 with Complex 1a[a]

| entry | 6:7 | conv to 8a (%)[b] | yield of 8a (%)[c] | Z:E[d] | homocoupled product (%)[d] |
|---|---|---|---|---|---|
| 1 | 1:1 | 42 | nd | 86:14 | 49 |
| 2 | 2:1 | 63 | 43 | 90.5:9.5 | 22 |
| 3 | 5:1 | 81 | 71 | 93:7 | 7 |
| 4 | 7:1 | 82 | nd | 93:7 | 6 |

[a-b]See Table 1.
[c-d]Yield of isolated and purified material (±5%).

We examined the efficiency of the cross metathesis process with varying amounts of 6 (Table 2). These studies established that, although fewer equivalents of 6 lead to diminished Z-selectivity and competitive homocoupling, with five equivalents of the inexpensive and commercially available enol ether (Table 2, entry 3), 8a can be obtained in 93:7 Z:E selectivity and 71% yield (7% homocoupled product). Excess enol ether 6 does not complicate product isolation, as this reagent is volatile and can be easily removed in vacuo.

Example 4

Mo-Catalyzed Z-Selective Cross-Metathesis of Vinyl Ethers

TABLE 3

Z-Selective Mo-Catalyzed Cross-Metathesis of Enol Ethers[a]

| entry | Z enol ether product | Mo complex; mol % | time (h); conv (%)[b] | yield (%)[c] | Z:E[b] |
|---|---|---|---|---|---|
| 1 | 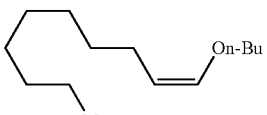<br>I (i.e., 8b) | 1a; 2.5 | 2; 59 | nd | 98:2 |
| 2 | 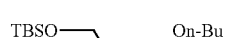<br>II | 1a; 2.5 | 2; 63 | nd | 89:11 |
| 3 | 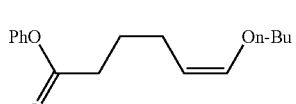<br>III | 1a, 2.5 | 2; 77 | nd | 98:2 |

TABLE 3-continued

Z-Selective Mo-Catalyzed Cross-Metathesis of Enol Ethers[a]

| entry | Z enol ether product | Mo complex; mol % | time (h); conv (%)[b] | yield (%)[c] | Z:E[b] |
|---|---|---|---|---|---|
| 4 | 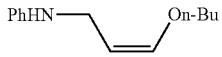<br>IV (i.e., 8e) | 1a; 5.0 | 1; 65 | 55 | >98:2 |
| 5 | 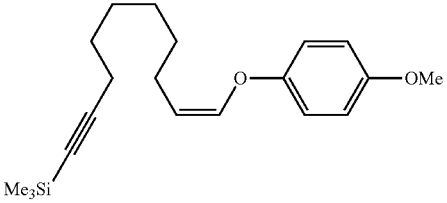<br>V (i.e., 10c) | 1b; 5.0 | 16; 47 | 47 | >98:2 |
| 6 | 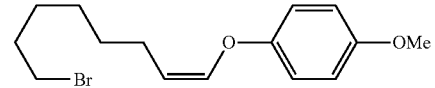<br>VI (i.e., 10b) | 1b; 5.0 | 16; 70 | nd | >98:2 |
| 7 | 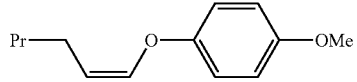<br>VII (i.e., 10a) | 1b; 5.0 | 16; 62 | 62 | >98:2 |

[a]Performed with 2.5 or 5.0 mol % bis-pyrrolide and 2.5 or 5.0 mol % enantiomerically pure (>98:2 enantiomer ratio) aryl alcohol in $C_6H_6$ (or toluene), 22° C., 1.0-16.0 h, $N_2$ atm.
[b]Determined by analysis of 400 MHz $^1$H NMR spectra of unpurified mixtures.
[c]Yield of purified products.
nd = not determined.

Although TBS-protected hydroxyl is depicted above, TIPS-protected hydroxyl also resulted in Z-selective metathesis. Regarding the 4-substituted phenyl rings depicted above, 3-substituted phenyl substrates similarly resulted in Z-selective metathesis.

TABLE 4

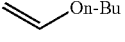
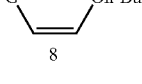
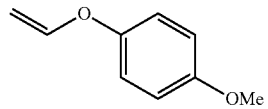
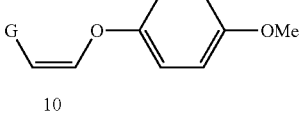

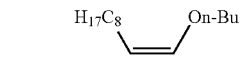
8b[b]
76% conv, 68% yield,
98% Z

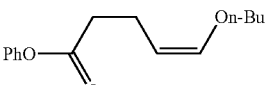
8c[b]
76% conv, 73% yield,
98% Z

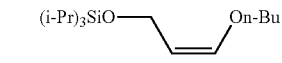
8d[b]
86% conv, 77% yield,
94% Z

TABLE 4-continued

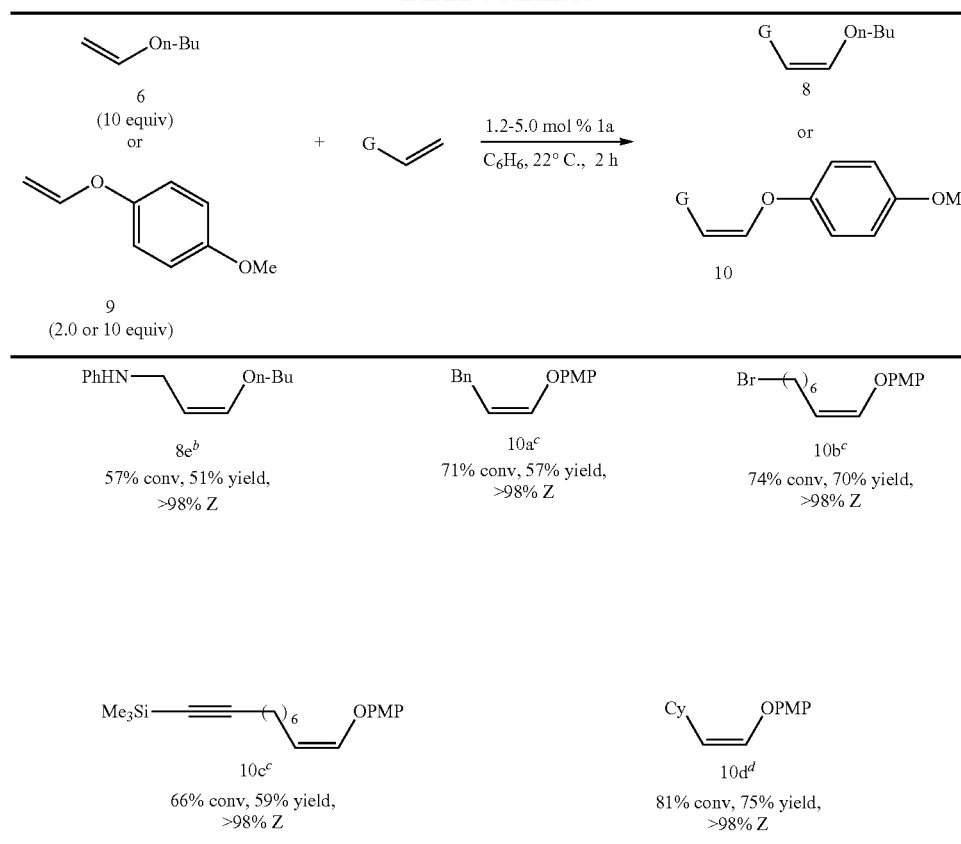

[a] Reactions performed under N$_2$ atm; conversions and Z selectivities determined by analysis of 400 MHz $^1$H NMR spectra of unpurified mixtures; yields of isolated products after purification (±5%).
[b] With 2.5 mol % 1a and 10 equiv 6.
[c] With 1.2 mol % 1a and 2.0 equiv 6.
[d] With 5.0 mol % 1a and 10 (10b) or 2.0 equiv 6 (10d).

Z-Disubstituted enol ethers were obtained in 57-77% yield through highly stereoselective (94% to >98% Z) cross metathesis reactions with Mo alkylidene 1a (Table 4). Alkyl (8) or aryl-substituted (10) Z enol ethers as well as those that bear a carboxylic ester (8c), a secondary amine (8e), a bromide (10b), or an alkyne (10c) were readily accessed. Reactions with the relatively electron-deficient 9 and electron-rich alkenes proceeded with 2.0 equivalents of the aryl-substituted enol ether; in contrast, 10 equivalents of alkyl-substituted 6 are required for similar efficiency. Such variations are likely because when 9 is used there is a better electronic match between the Mo-alkylidenes derived from the cross partners and either of the two olefins,[1,4] favoring cross metathesis versus homocoupling. It is important to note that only 1.2 mol % 1a and 2.0 equivalents of the p-methoxyphenylenol ether (e.g., 10a-b and 10d, Table 4) are sufficient for an effective and exceptionally Z-selective cross metathesis.

Scheme 2.

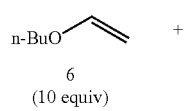

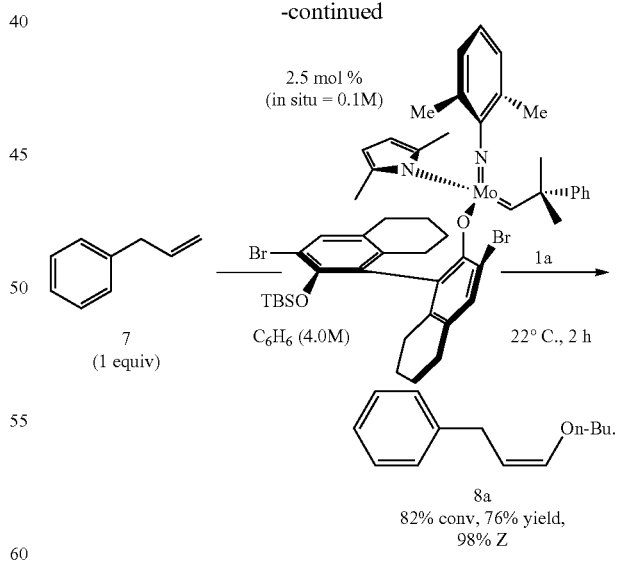

(Z)-(3-Butoxyallyl)benzene (8a). Following the general procedure for enol ether cross metathesis, allyl benzene (50.0 mg, 0.423 mmol, 7) was treated with butyl vinyl ether (424 mg, 4.23 mmol), 2.5 mol % of in situ-generated complex 1a (106 μL, 0.10 M, 10.6 μmol; final substrate concentration=4.0

M), and allowed to stir for 2 h. The unpurified product is 98% Z (as determined by 400 MHz $^1$H NMR analysis). The resulting brown oil was purified by neutral alumina chromatography (100% hexanes) to afford 8a (61.3 mg, 0.322 mmol, 76.0% yield, >98% Z isomer) as a colorless oil. The physical and spectral data were identical to those previously reported for compound 8a.[9] IR (neat): 3028 (w), 2959 (m), 2933 (m), 2872 (m), 1663 (s), 1495 (m), 1453 (m), 1373 (m), 1253 (m), 1108 (s); $^1$H NMR (400 MHz, CDCl$_3$): δ 7.32-7.16 (5H, m), [diagnostic E isomer signal: 6.37 (1H, dt, J=16.0, 1.2 Hz)], 6.08 (1H, dt, J=6.0, 1.6 Hz), 4.57 (1H, td, J=7.6, 6.2 Hz), 3.79 (2H, t, J=6.4 Hz), 3.45 (2H, d, J=7.6 Hz), 1.69-1.61 (2H, m), 1.49-1.39 (2H, m), 0.97 (3H, t, J=7.6 Hz); $^{13}$C NMR (100 MHz, CDCl$_3$): δ 145.7, 142.1, 128.4, 128.4, 125.8, 105.4, 72.2, 32.0, 30.4, 19.2, 14.0; HRMS (ESI$^+$) [M+H]$^+$ calcd for C$_{13}$H$_{19}$O: 191.1436, found: 191.1432.

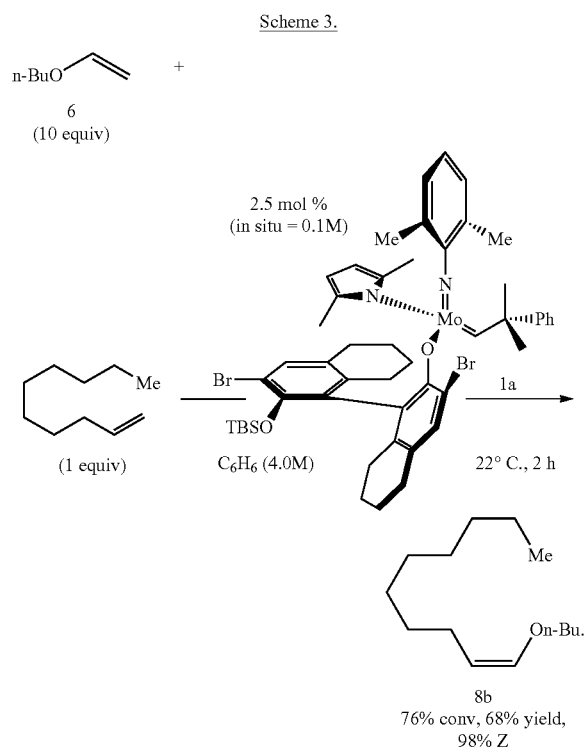

8b
76% conv, 68% yield, 98% Z (Z)-1-Butoxydec-1-ene (8b). Following the general procedure, 1-decene (50.0 mg, 0.356 mmol) was treated with butyl vinyl ether (357 mg, 3.56 mmol) and 2.5 mol % of in situ-generated complex 1a (89.0 μL, 0.10 M, 8.90 μmol; final substrate concentration=4.0 M) and allowed to stir for 2 h. The unpurified product is 98% Z (as determined by 400 MHz $^1$H NMR analysis). The resulting brown oil was purified by neutral alumina chromatography (100% hexanes) to afford 8b (51.2 mg, 0.241 mmol, 68.0% yield, 98% Z isomer) as a colorless oil. IR (neat): 2958(s), 2923 (s), 2854 (s), 1664 (s), 1464 (m), 1375 (m), 1306 (w), 1259 (m), 1102 (s); $^1$H NMR (400 MHz, CDCl$_3$): δ [diagnostic E isomer signal: 6.21 (1H, dt, J=12.8, 1.2 Hz)], 5.91 (1H, dt, J=6.4, 1.6 Hz), 4.32 (1H, td, J=7.2, 6.2 Hz), 3.70 (2H, t, J=6.4 Hz), 2.06 (2H, tdd, J=7.2, 7.2, 1.2 Hz), 1.63-1.55 (2H, m), 1.44-1.21 (14H, m), 0.93 (3H, t, J=7.6 Hz), 0.88 (3H, t, J=7.2 Hz); $^{13}$C NMR (100 MHz, CDCl$_3$): δ 145.0, 107.1, 72.0, 32.1, 32.0, 30.0, 29.6, 29.5, 29.4, 24.1, 22.8, 19.2, 14.3, 14.0; HRMS (ESI$^+$) [M+H]$^+$ calcd for C$_{14}$H$_{29}$O: 213.2218, found: 213.2220.

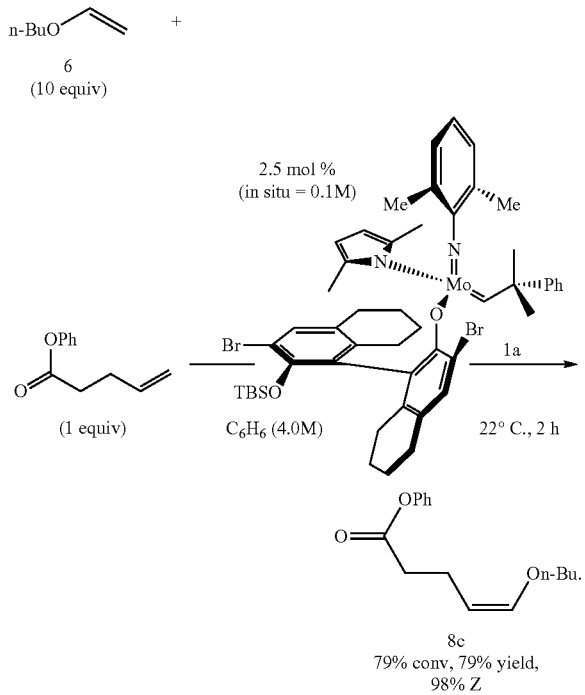

8c
79% conv, 79% yield, 98% Z (Z)-Phenyl 5-butoxypent-4-enoate (8c). Following the general procedure, phenyl pent-4-enoate (50.0 mg, 0.284 mmol) was treated with butyl vinyl ether (284 mg, 2.84 mmol) and 2.5 mol % of in situ-generated complex 1a (71.0 μL, 0.10 M, 7.09 μmol; final substrate concentration=4.0 M) and allowed to stir for 2 h. The unpurified product is 98% Z (as determined by 400 MHz $^1$H NMR analysis). The resulting oil was purified by silica gel chromatography (50:1 hexanes: Et$_2$O) to afford 8c (55.6 mg, 0.224 mmol, 79.0% yield, >98% Z isomer) as a colorless oil. IR (neat): 3040 (w), 2959 (m), 2933 (m), 2872 (m), 1759 (s), 1663 (m), 1594 (m), 1493 (m), 1374 (m), 1359 (m), 1272 (m), 1227 (m), 1195 (s), 1162 (s), 1130 (s), 1102 (s), 1072 (m); $^1$H NMR (400 MHz, CDCl$_3$): δ 7.40-7.34 (2H, m), 7.25-7.19 (1H, m), 7.11-7.07 (2H, m), [diagnostic E isomer signal: 6.37 (1H, d, J=12.8 Hz)], 6.02 (1H, dt, J=6.0, 1.2 Hz), 4.43 (1H, td, J=6.8, 6.4 Hz), 3.75 (2H, t, J=6.4 Hz), 2.66-2.60 (2H, m), 2.56-2.49 (2H, m), 1.65-1.57 (2H, m), 1.46-1.35 (2H, m), 0.94 (3H, t, J=7.4 Hz); $^{13}$H NMR (100 MHz, CDCl$_3$): δ 172.0, 150.9, 146.4, 129.4, 125.7, 121.7, 103.8, 72.2, 34.7, 32.0, 19.9, 19.1, 13.9; HRMS (ESI$^+$) [M+H]$^+$ calcd for C$_{15}$H$_{21}$O$_3$: 249.1491, found: 249.1500.

Scheme 5.

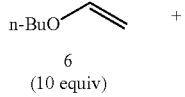

6
(10 equiv)

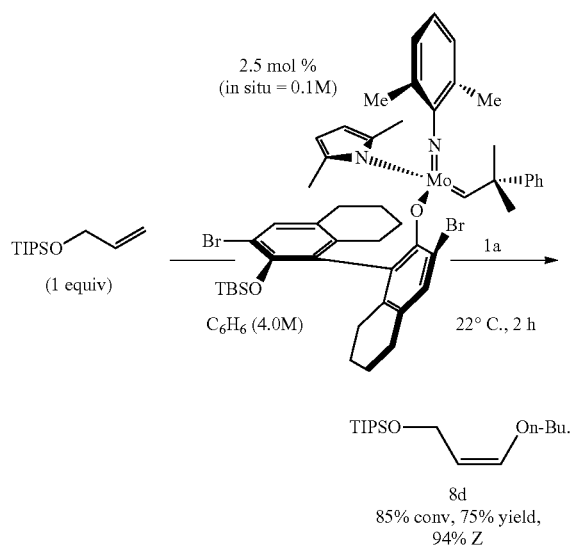

(Z)-((3-Butoxyallyl)oxy)triisopropylsdane (8d). Following the general procedure, (allyloxy)triisopropylsilane (50.0 mg, 0.233 mmol) was treated with butyl vinyl ether (234 mg, 2.33 mmol) and 2.5 mol % of in situ-generated complex 1a (58.0 µL, 0.10 M, 5.83 µmol; final substrate concentration=4.0 M) and allowed to stir for 2 h. The unpurified product was 94.5% Z (as determined by 400 MHz $^1$H NMR analysis). The resulting oil was purified by neutral alumina chromatography (100% hexanes) to afford 8d (50.3 mg, 0.176 mmol, 76.0% yield, 95.5% Z isomer) as a colorless oil. IR (neat): 2958 (s), 2941 (s), 2865 (s), 1665 (s), 1463 (m), 1381 (m), 1246 (m), 1087 (s), 1061 (s), 1013 (m), 995 (m); $^1$H NMR (400 MHz, CDCl$_3$): δ [diagnostic E isomer signal: 6.46 (1H, d, J=12.8 Hz)], 5.95 (1H, dt, J=6.0, 1.4 Hz), 4.57 (1H, dt, J=6.4, 6.4 Hz), 4.35 (2H, dd, J=6.4, 1.2 Hz), 3.73 (2H, t, J=6.6 Hz), 1.63-1.54 (2H, m), 1.43-1.33 (2H, m), 1.16-1.01 (21H, m), 0.92 (3H, t, J=7.6 Hz); $^{13}$C NMR (100 MHz, CDCl$_3$): δ 145.5, 106.9, 72.4, 57.3, 32.0, 19.1, 18.2, 13.9, 12.2; HRMS (ESI$^+$) [M+Na]$^+$ calcd for C$_{16}$H$_{34}$O$_2$Na: 309.2226, found: 309.2219.

Scheme 6.

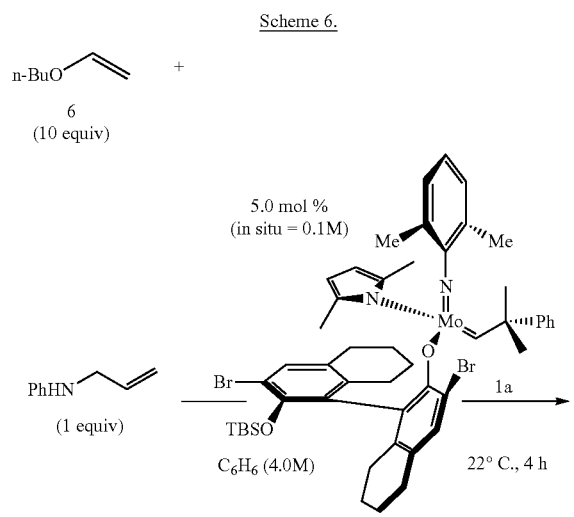

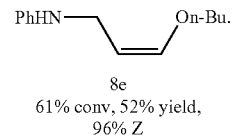

(Z)—N-(3-Butoxyallyl)aniline (8e). Following the general procedure, N-allylaniline (50.0 mg, 0.375 mmol) was treated with butyl vinyl ether (376 mg, 3.75 mmol) and 5 mol % of in situ-generated complex 1a (188 µL, 0.10 M, 18.7 µmol; final substrate concentration=2.0 M) and allowed to stir for 4 h. The unpurified product is 96% Z (as determined by 400 MHz $^1$H NMR analysis). The resulting oil was purified by silica gel chromatography (50:1 hexanes:Et$_2$O) to afford 8e (40.2 mg, 0.196 mmol , 52.0% yield, 96% Z isomer) as a light yellow oil. IR (neat): 3410 (br), 3048 (w), 2958 (m), 2932 (m), 2871 (m), 1660 (m), 1601 (s), 1503 (s), 1467 (m), 1431(w), 1375 (m), 1314 (m), 1250 (m), 1108 (s), 1094 (s), 1040 (m), 745 (s), 691 (s); $^1$H NMR (400 MHz, CDCl$_3$): ™ δ 7.19-7.14 (2H, m), 6.72-6.67 (1H, m), 6.66-6.62 (2H, m), [diagnostic E isomer signal: 6.51 (1H, d, J=12.8 Hz)], 6.08 (1H, dt, J=6.4, 1.4 Hz), 4.51 (1H, td, J=6.6, 6.4 Hz), 3.82-3.74 (1H, m), 3.81 (2H, dd, J=6.8, 1.2 Hz), 3.79 (2H, t, J=6.4 Hz), 1.67-1.59 (2H, m), 1.47-1.37 (2H, m), 0.95 (3H, t, J=7.4 Hz); $^{13}$C NMR (100 MHz, CDCl$_3$): ™ δ 148.5, 147.4, 129.3, 117.4, 113.2, 103.5, 72.6, 38.6, 32.0, 19.2, 14.0; HRMS (ESI$^+$) [M+H]$^+$ calcd for C$_{13}$H$_{20}$NO: 206.1545, found: 206.1541.

Scheme 7.

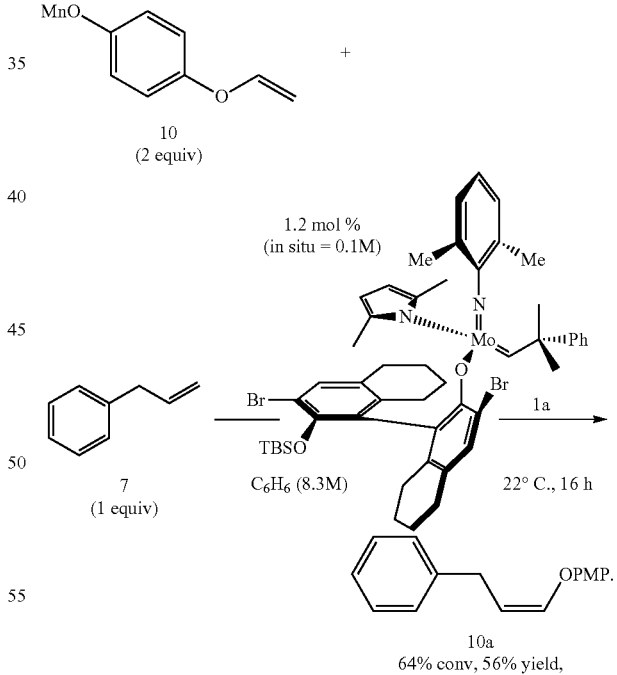

(Z)-1-Methoxy-4((3-phenylprop-1-en-1-yl)oxy)benzene (10a). Following the general procedure, allyl benzene (50.0 mg, 0.423 mmol, 7) was treated with p-methoxyphenyl vinyl ether (127 mg, 8.46 mmol) and 1.2 mol % of in situ-generated complex 1a (51.0 µL, 0.10 M, 5.08 µmol; final substrate concentration=8.3 M) and allowed to stir for 16 h. The unpurified product is >98% Z (as determined by 400 MHz $^1$H NMR analysis). Excess p-methoxyphenyl vinyl ether was removed by vacuum distillation (1.0 torr, 80° C.). The resulting oil was purified by neutral alumina chromatography (100% hexanes to 100:1 hexanes:Et$_2$O) to afford 10a (56.8 mg, 0.236 mmol, 56.0% yield, >98% Z isomer) as a colorless oil. IR (neat): 3027 (w), 3000 (w), 2950 (w), 2908 (w), 2834 (w), 1664 (m), 1502 (s), 1464 (m), 1453 (m), 1441 (m), 1384 (m), 1212 (s), 1179 (m), 1088 (m), 1064 (m), 1034 (m), 989 (m); NMR (400 MHz, CDCl$_3$): δ 7.33-7.25 (4H, m), 7.24-7.18 (1H, m), 7.01-6.95 (2H, m), 6.89-6.84 (2H, m), 6.42 (1H, dt, J=6.0, 1.6 Hz), 4.96 (1H, td, J=7.6, 6.0 Hz), 3.80 (3H, s), 3.58 (2H, dd, J=7.6, 1.2 Hz); $^{13}$C NMR (100 MHz, CDCl$_3$): δ 155.4, 151.7, 141.9, 141.2, 128.6, 128.5, 126.0, 117.6, 114.8, 110.6, 55.9, 30.4; HRMS (ESI$^+$) [M+NH$_4$]$^+$ calcd for C$_{16}$H$_{20}$NO$_2$: 258.1494, found: 258.1491.

NMR (100 MHz, CDCl$_3$): δ 155.2, 151.8, 141.4, 117.5, 114.8, 112.0, 55.8, 34.1, 33.0, 29.4, 28.4, 28.1, 23.9; HRMS (ESI$^+$) [M+H]$^+$ calcd for C$_{15}$H$_{22}$BrO$_2$: 313.0803, found: 313.0800

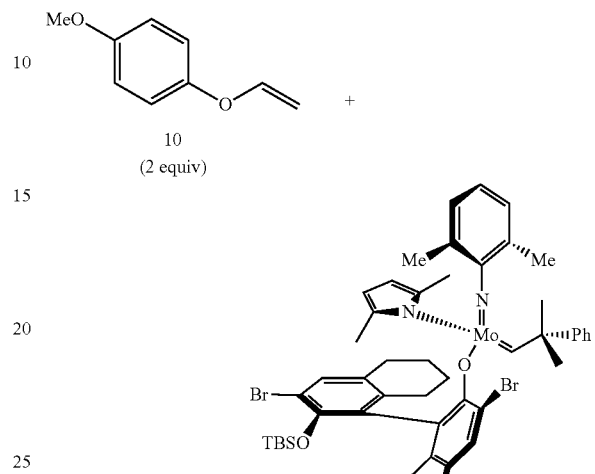

Scheme 9.

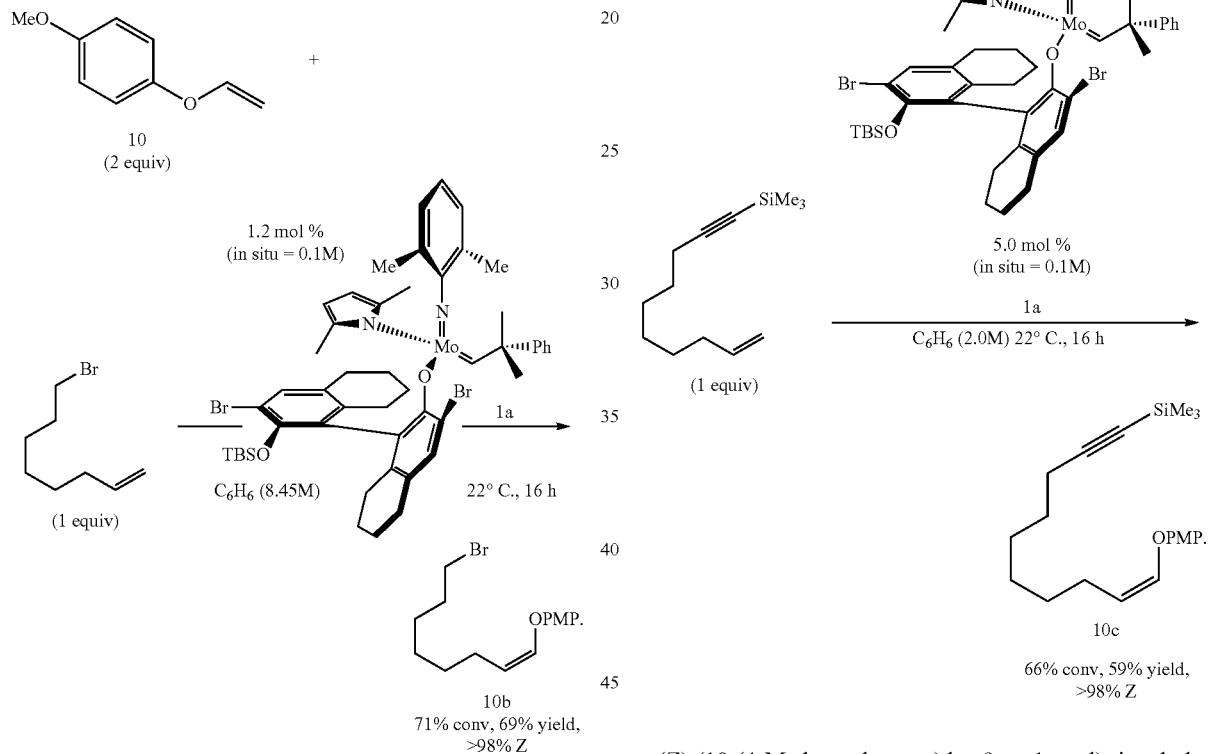

Scheme 8.

(Z)-1-((8-Bromooct-1-en-1-yl)oxy)-4-methoxybenzene (10b). Following the general procedure, 8-bromooct-1-ene (50.0 mg, 0.262 mmol) was treated with p-methoxyphenyl vinyl ether (79.0 mg, 0.5 23 mmol) and 1.2 mol % of in situ-generated complex 1a (31.0 μL, 0.10 M, 3.14 μmol; final substrate concentration=8.45 M) and allowed to stir for 16 h. The unpurified product is >98% Z (as determined by 400 MHz $^1$H NMR analysis). Excess p-methoxyphenyl vinyl ether was removed by vacuum distillation (1.0 torr, 80° C.). The resulting oil was purified by neutral alumina chromatography (100% hexanes to 100:1 hexanes:Et$_2$O) to afford 10b (56.9 mg, 0.182 mmol, 69.0% yield, >98% Z isomer) as a colorless oil. IR (neat): 2924 (s), 2854 (m), 1665 (m), 1503 (s), 1463 (m), 1441 (m), 1389 (w), 1214 (s), 1180 (m), 1102 (m), 1040 (s); $^1$H NMR (400 MHz, CDCl$_3$): δ 6.95-6.90 (2H, m), 6.86-6.82 (2H, m), 6.28 (1H, dt, J=6.0, 1.5 Hz), 4.73 (1H, td, J=7.4, 6.0 Hz), 3.78 (3H, s), 3.40 (2H, t, J=7.0 Hz), 2.24-2.17 (2H, m), 1.90-1.81 (2H, m), 1.49-1.32 (6H, m); $^{13}$C (Z)-(10-(4-Methoxyphenoxy)dec-9-en-1-ynyl)trimethylsilane (10c). Following the general procedure, dec-9-en-1-ynyltrimethylsilane (50.0 mg, 0.240 mmol) was treated with p-methoxyphenyl vinyl ether (360 mg, 2.40 mmol) and 5 mol % of in situ-generated complex 1a (120 μL, 0.10 M, 12.0 μmol: final substrate concentration=2.0 M) and allowed to stir for 16 h. The unpurified product is >98% Z (as determined by 400 MHz $^1$H NMR analysis). Excess p-methoxyphenyl vinyl, ether was removed by vacuum distillation (1.0 torr, 80° C.). The resulting oil was purified by neutral alumina chromatography (100% hexanes to 100:1 hexanes:Et$_2$O) to afford 10c (46.6 mg, 0.141 mmol, 59.0% yield, >98% Z isomer) as a colorless oil. IR (neat): 2931 (m), 2856 (m), 2173 (m), 1665 (m), 1504 (s), 1464 (m), 1442 (m), 1390 (m), 1247 (s), 1215 (s), 1180 (m), 1104 (m), 1048 (s); $^1$H NMR (400 MHz, CDCl$_3$): δ 6.95-6.90 (2H, m), 6.86-6.81 (2H, m), 6.28 (1H, dt, J=6.0, 1.4 Hz), 4.74 (1H, td, J=7.2, 6.2 Hz), 3.78 (3H, s), 2.24-2.17 (4H, m), 1.56-1.47 (2H, m), 1.46-1.30 (6H, m), 0.15 (9H, s); $^{13}$C NMR (100 MHz, CDCl$_3$): ™ δ 155.2, 151.8, 141.3, 117.5, 114.7, 112.2, 107.9, 84.4, 55.8, 29.5, 28.8, 28.8, 28.8, 24.0, 20.0, 0.3; HRMS (ESI⁺) [M+H]⁺ calcd for C$_{20}$H$_{31}$O$_2$Si: 331.2093, found: 331.2106.

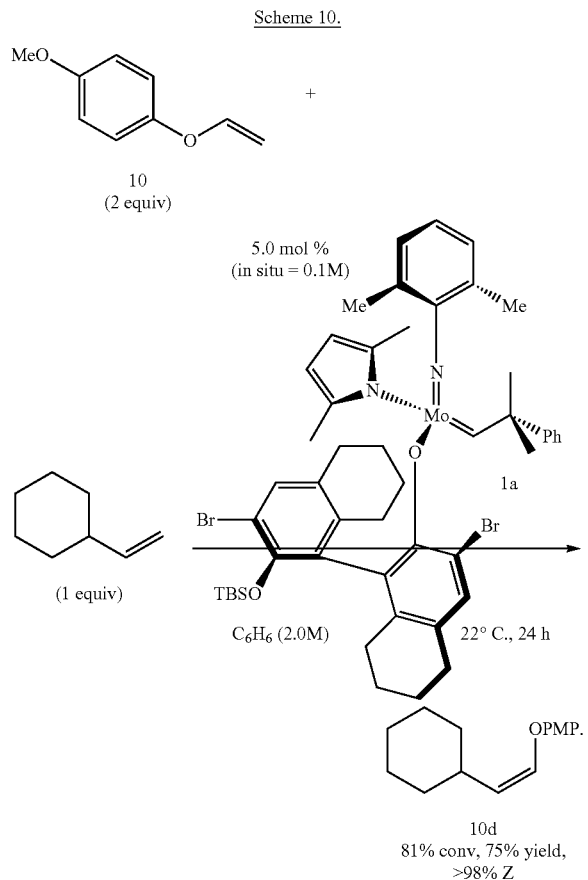

(Z)-1-((2-Cyclohexylvinyl)oxy)-4-methoxybenzene (10d). Following the general procedure, vinylcyclohexane (20.0 mg, 0.182 mmol) was treated with p-methoxyphenyl vinyl ether (55.0 mg, 0.363 mmol) and 5 mol % of in situ-generated complex 1a (91.0 μL, 0.10 M, 9.08 μmol; final substrate concentration=2.0 M) and allowed to stir for 24 h. The unpurified product is >98% Z (as determined by 400 MHz ¹H NMR analysis). Excess p-methoxyphenyl vinyl ether was removed by vacuum distillation (1.0 torr, 80° C.). The resulting oil was purified by neutral alumina chromatography (50:1 hexanes:Et$_2$O) to afford 10d (31.8 mg, 0.137 mmol, 75.0% yield, >98% Z isomer) as a colorless oil. IR (neat): 2925 (m), 2850 (m), 1664 (w), 1505 (s), 1465 (w), 1447 (w), 1392 (w), 1293 (w), 1244 (m), 1224 (s), 1180 (w), 1102 (w), 1040 (m); ¹H NMR (400 MHz, CDCl$_3$): δ 6.95-6:91 (2H, m), 6.86-6.82 (2H, m), 6.17 (1H, dd, J=6.4, 1.2 Hz), 4.63 (1H, d, J=9.2, 6.0 Hz), 3.78 Hz (3H, s), 2.65-2.54 (1H, m), 1.78-1.60 (5H, m), 1.39-1.06 (5H, m); ¹³C NMR (100 MHz, CDCl$_3$): δ 155.2, 151.9, 139.8, 118.6, 117.5, 114.8, 55.9, 33.6, 33.5, 26.3, 26.1; HRMS (ESI⁺) [M+H]⁺ calcd for C$_{15}$H$_{21}$O$_2$: 233.1542, found: 233.1542.

Example 5

Effect of Reduced Pressure on Catalytic Cross-Metathesis of Vinyl Ethers

In some embodiments, wherein the vinyl enol ether is more valuable than the second olefin-containing species, it is desired to use a reduced amount of enol ether relative to the 10:1 ratios depicted above. However, lowering the enol ether concentration in certain instances (e.g., when the second olefin-containing species is an aliphatic olefin) can lead to reduced efficiency and/or Z-selectivity. To address the complication regarding the levels of conversion in the cross-metathesis reactions, and without wishing to be bound by any particular theory, it was reasoned that, if the catalytic reactions are performed under vacuum sufficient to remove the ethylene generated as the byproduct but not the lower molecular weight reactants, a more efficient process could be achieved. The mechanistic basis of this contention may be founded on the scenario that the presence of ethylene may result in high concentrations of highly reactive stereogenic-at-Mo methylidene complexes. Such complexes could react with the desired Z olefin to regenerate starting materials and effect equilibration favoring the lower energy E isomer.

Figure 3:
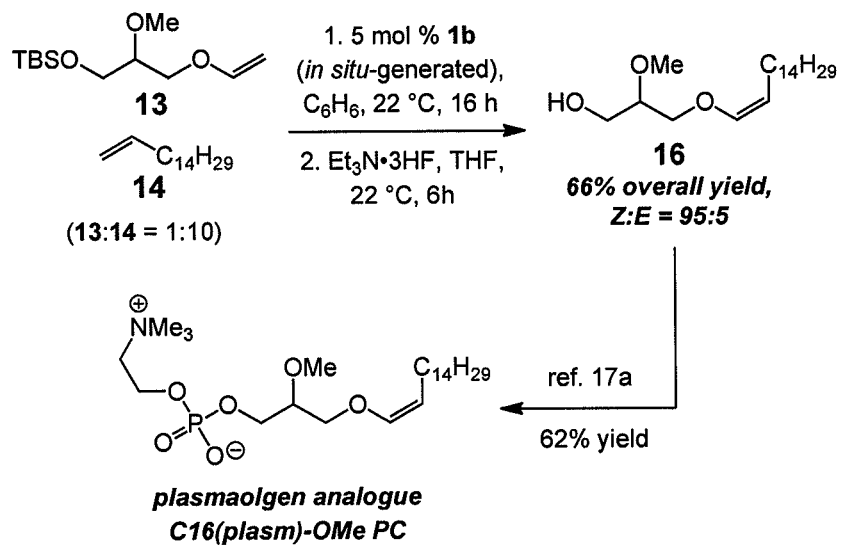
FIG. 3 illustrates the synthesis of a plasmaolgen analogue using a Z-selective cross-metathesis reaction.

Initial Study on the Effect of Reduced Pressure on Catalytic Cross-Metathesis of Vinyl Ethers: When a 5:1 mixture of enol ether 13 and 1-hexadecene (14) were subjected to 5 mol % Mo complex 1b (entry 1, Table 3), 68% conversion was obtained after 16 hours and disubstituted enol ether 15 is obtained in 90:10 Z:E ratio. When the same reaction was carried out under reduced pressure (entry 2, ~10 torr), 87% conversion was observed and 15 was generated with improved Z-selectivity. As the data in entries 3-5 indicate, when cross metathesis is carried out under vacuum, excess of the more easily accessible and less valuable terminal alkene can be used; under such conditions, 64-77% conversion to the desired disubstituted enol ether was observed without diminution in Z-selectivity (95% Z). As illustrated in FIG. 3, enol ether 16, as described in Shin et al., J. Am. Chem. Soc. 2001, 123, 508-509, in the synthesis of plasmalogen analogue C16 (plasm)-OMe PC can be obtained in 66% overall yield (for two steps) and in 95:5 Z:E selectivity.

TABLE 5

| entry | Mo complex | 13:14 | time (h); conv (%)[b] | condition[c] | Z:E[b] |
|---|---|---|---|---|---|
| 1 | 1b | 5:1 | 16; 68 | ambient | 90:10 |
| 2 | 1b | 5:1 | 16; 87 | vacuum[c] | 95:5 |
| 3 | 1b | 1:10 | 2; 64 | vacuum | 95:5 |
| 4 | 1a | 1:10 | 2; 77 | vacuum | 95:5 |
| 5 | 2 | 1:10 | 2; 66 | vacuum | 96:4 |

[a-b]See Table 1.

[c]Vacuum of approximately 11.0 torr applied.

Applications to Stereoselective Synthesis of C18 (plasm)—16:0 (PC).

TABLE 6

Effect of Reduced Pressure on Catalytic Cross-Metathesis of Synthon 11

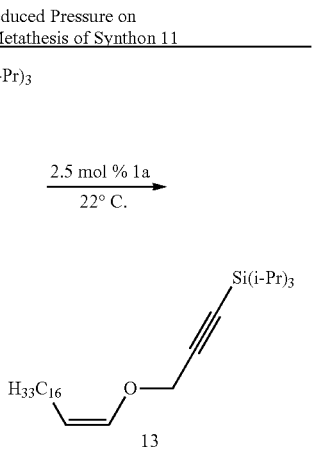

| entry | 11:12 | time; conv (%)[b] | solvent | condition | Z:E[b] |
|---|---|---|---|---|---|
| 1 | 5:1 | 2 h; 85 | $C_6H_6$ | ambient | >98:2 |
| 2 | 1:1 | 2 h; 47 | $C_6H_6$ | ambient[c] | 91.5:9.5 |
| 3 | 1:1 | 2 h; 78 | $C_6H_6$ | 1.0 torr | 97:3 |
| 4 | 1:2 | 2 h; 88 | Decalin | 1.0 torr | 97:3 |

Methods of the present invention are useful for, inter alia, the diastereo- and enantioselective synthesis of C18 (plasm)-16:0 (PC) (cf. Scheme 11). This initiative, however, posed an additional challenge in that the enol ether (11, Table 6) to be used is more valuable than the commercially available and inexpensive 1-octadecene (12), rendering the use of excess amounts of the former unfavorable. Lowering the enol ether concentration, however, diminished efficiency and Z-selectivity, as detailed above and substantiated by the data in Table 6 (entries 1-2; 85% and 47% cony. with 5:1 and 1:1 11:12). Larger quantities of the less valuable 12 would improve yield and selectivity, since Mo methylidene concentration is likely lowered through its reaction with excess alkene. On the other hand, increased amounts of the aliphatic olefins, unlike an enol ether, can give rise to homocoupling and ethylene generation. Ethylene is detrimental to the rate of the desired cross metathesis because it competes with the substrates for reaction with the available alkylidene, and causes diminished stereoselectivity by increasing methylidene concentration (Z olefin isomerization; see above). It was surprisingly found that an efficient cross metathesis can be induced to proceed with only a relatively slight excess of the aliphatic olefin (12), if the negative effects of the generated ethylene were to be attenuated by performing the reaction under vacuum. Indeed, as shown in Table 6, when catalytic cross metathesis is performed with an equal amount of 11 and 12 under 1.0 torr (entry 3), efficiency (78% vs 47% cony in entry 2) as well as stereoselectivity is substantially improved (97% vs 91.5% Z).

Scheme 11.

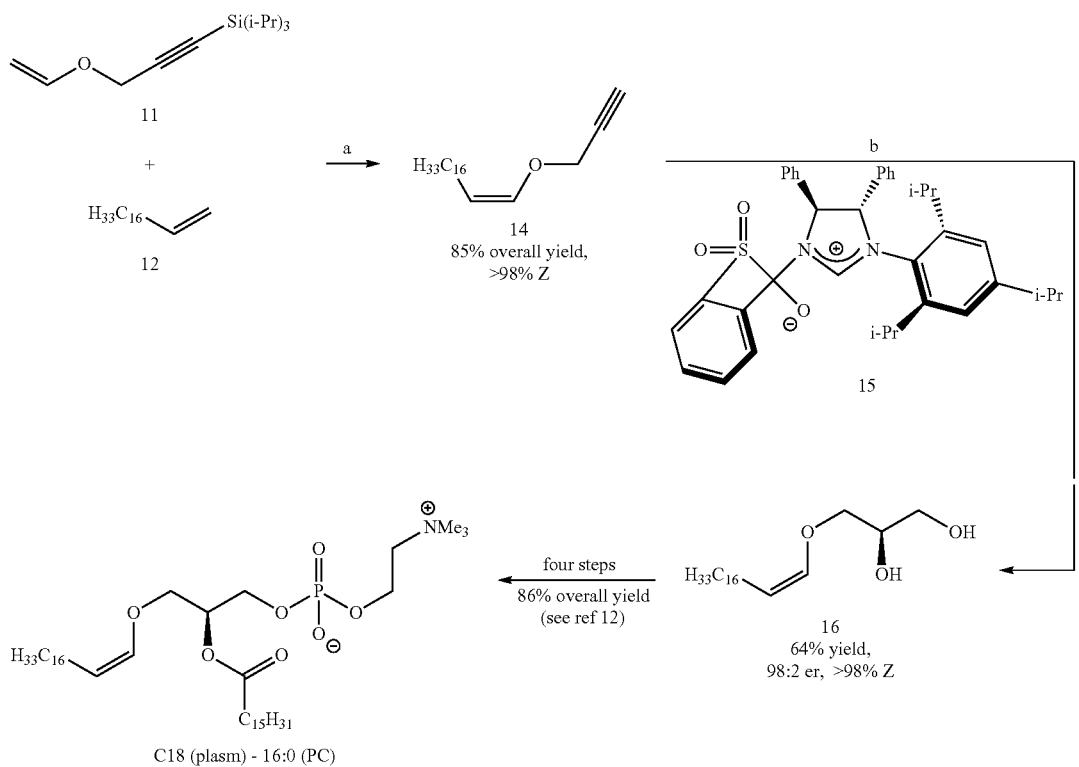

Conditions: (a) 1. See entry 4, Table 4. 2. 5.0 equiv (n-Bu)$_4$NF, THF, 22° C., 2 h., 2.5 mol % CuCl, 20 mol % NaOt-Bu, 2.1 equiv B$_2$(pin)$_2$, 3.0 equiv MeOH, THF, 0° C., 24 h; 30% H$_2$O$_2$, NaOH in aqueous THF, 1.0 h.

Scheme 11 depicts the diastereo- and enantioselective synthesis of C18 (plasm)-16:0 (PC). Under vacuum, with two equivalents of 12 (vs 11) and decalin as solvent (to prevent precipitation of the homocoupled byproduct causing catalyst sequestration) 89% conversion is observed in two hours and Z-13 is obtained with 97% selectivity (entry 4, Table 5). Removal of the silyl group delivers stereoisomerically pure Z-14 in 85% overall yield (Table 4). Importantly, catalytic cross metathesis between 11 and 12 has been performed on gram-scale with 1.0 mol % of in situ-generated 1a and two equivalents of 12, affording Z-13 with >98% stereoselectivity and in 71% yield after purification (3 h, 1.0 torr, 79% conv). Cu-catalyzed site- and enantioselective dihydroboration furnishes 16 (98:2 er), which has been previously converted to C18 (plasm)-16:0 (PC) in four steps and 86% overall yield.

Scheme 12.

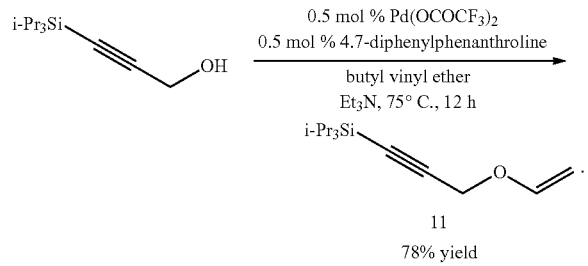

78% yield

Triisopropyl(3-(vinyloxy)prop-1-yn-1-yl)silane (11).[10] Scheme 12 depicts the synthesis of triisopropyl(3-(vinylaxy)prop-1-yn-1-yl)silane (11). A 100-mL round-bottom flask equipped with stir bar was charged with palladium trifluoroacetate (16.0 mg, 47.1 mmol), 4,7-diphenylphenanthroline (16.0 mg, 47.1 μmol), and butyl vinyl ether (23.1 mL, 188 mmol). 3-(Triisopropylsilypprop-2-yn-1-ol[11] (2.00 g, 9.42 mmol) and triethylamine (982 μL, 7.06 mmol) were added to the yellow solution. The flask was fitted with a reflux condenser and allowed to stir at 75° C. for 16 h. The Pd catalyst was removed by passing the reaction mixture through a short (~2.5 cm) plug of celite and activated charcoal. The resulting unpurified oil was purified by silica gel chromatography (100:1 hexanes:Et$_3$N) to afford 11 (1.75 g, 7.34 mmol, 78.0% yield) as a colorless oil. IR (Neat): 2944 (s), 2893 (m), 2866 (s), 1639 (m), 1617 (m), 1464 (m), 1368 (m), 1355 (m), 1318 (m), 1189 (s), 1152 (m), 1067 (m), 1054 (m), 1030 (m), 1017 (m); $^1$H NMR (400 MHz, CDCl$_3$): δ 6.46 (1H, dd, J=14.4, 6.8 Hz), 4.42 (2H, s), 4.33 (1H, dd, J=14.0, 2.4 Hz), 4.13 (1H, dd, J=6.8, 2.0 Hz), 1.08-1.06 (21H, m); $^{13}$C NMR (100 MHz, CDCl$_3$): δ 150.4, 101.8, 88.9, 88.5, 56.8, 18.7, 11.3; HRMS (ESI$^+$) [M+H]$^+$ calcd for C$_{14}$H$_{27}$OSi: 239.1831, found: 239.1830.

Scheme 13.

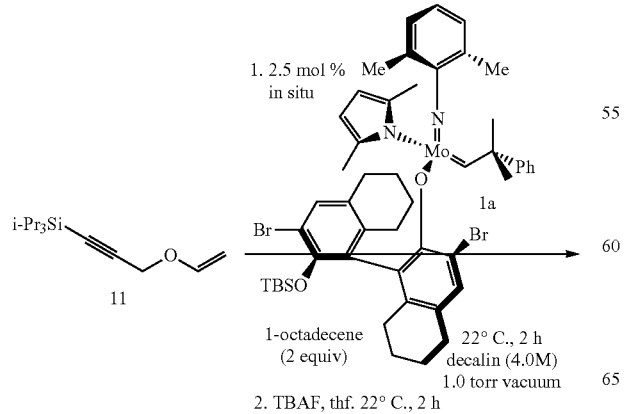

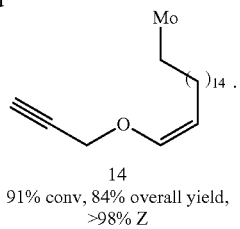

14
91% conv, 84% overall yield,
>98% Z (Z)-1-(prop-2-yn-1-yloxy)octadec-1-ene (14). Scheme 13 depicts the synthesis of (Z)-1-(prop-2-yn-1-yloxy)octadec-1-ene (14). In an N$_2$-filled dry box, a 20-mL vial equipped with a magnetic stir bar was charged with substrate 11 (50.0 mg, 0.2 10 mmol), and 2.5 mol % of in situ-generated complex 1a (52.0 μL, 0.10 M, 5.24 μmol; final substrate concentration=4.0 M). A separate 2-mL vial was charged with 1-octadecene (106 mg, 0.4 19 mmol) and decalin (106 μL). The resulting solution was transferred to substrate 11 and catalyst by syringe, a septum, fitted with an outlet needle, was quickly attached to the vial and an adapter was attached to the top of the septum and vacuum (~1.0 torr) applied. The resulting solution was allowed to stir for 2 h. The reaction vessel was removed from the dry box and the reaction quenched by the addition of benchtop Et$_2$O (~1 mL). The unpurified product is 98% Z (as determined by 400 MHz $^1$H NMR analysis).

The unpurified residue was dissolved in Et$_2$O and passed through a 2.5 cm plug of neutral alumina to remove inorganic salts. The solution was then concentrated. In a 25-mL round-bottom flask equipped with a stir bar, the resulting residue was treated with TBAF (1.0 M in THF, 1.05 mL, 1.05 mmol), and allowed to stir for 2 h. The solution was diluted with Et$_2$O (~10 mL), passed through a 5 cm plug of neutral alumina, and concentrated. The resulting white solid was purified by chromatography on neutral alumina (100% hexanes) to afford 14 (53.7 mg, 0.175 mmol, 84.0% yield, >98% Z isomer) as a white solid. M.P. 30-31° C.; IR (neat): 3311 (w), 2923 (s), 2853 (s), 1666 (w), 1466 (w), 1358 (w), 1278 (w), 1098 (m), 723 (w), 667 (w), 631 (w); $^1$H NMR (400 MHz, CDCl$_3$): δ 6.02 (1H, dt, J=6.4, 1.4 Hz), 4.50 (1H, td, J=7.6,6.3 Hz), 4.35 (2H, d, J=2.4 Hz), 2.46 (1H, t, J=2.6 Hz), 2.11-2.04 (2H, m), 1.38-1.19 (28H, m), 0.88 (3H, t, J=7.0 Hz); $^{13}$C NMR (100 MHz, CDCl$_3$): δ 143.1, 109.8, 79.3, 74.9, 58.9, 32.1, 29.9, 29.8, 29.8, 29.7, 29.5, 29.4, 24.1, 22.8, 14.3; HRMS (ESI$^+$) [M+H]$^+$ calcd for C$_{21}$H$_{39}$O: 307.3001, found: 307.3000.

Scheme 14.

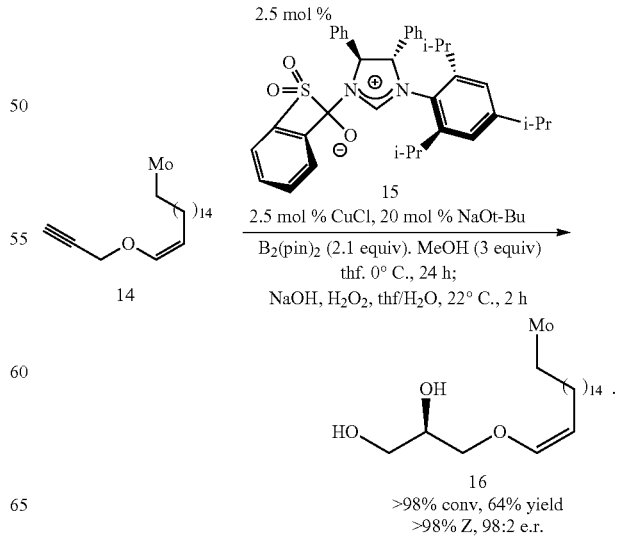

16
>98% conv, 64% yield
>98% Z, 98:2 e.r.

(R,Z)-3-(Octadec-1-en-1-yloxy)propane-1,2-diol (16). Scheme 14 depicts the synthesis of (R,Z)-3-(Octadec-1-en-1-yloxy)propane-1,2-diol (16). In an $N_2$-filled glovebox an oven-dried (135° C.) 25-mL round-bottom flask equipped with stir bar was charged with CuCl (2.00 mg, 20.4 1&mol), imidazolinium salt 16[13] (11.8 mg, 20.4 µmol), sodium tert-butoxide (15.7 mg, 0.163 mmol), THF (2.0 mL), and the mixture allowed to stir for 20 min. Bis(pinacolato) diboron was added to the solution (solution turns brown), and the mixture allowed to stir for 20 min. The solution was allowed to cool to 0° C., after which a solution of enyne 14 (250 mg, 0.8 16 mmol) in THF (2.0 mL) and MeOH (99.0 µL, 2.45 mmol) were added over a period of one minute, and the mixture was allowed to stir for 24 h at 0° C. The resulting solution was diluted with ethyl acetate (~10 mL) and passed through a 2.5 cm plug of silica gel, and the volatiles were removed in vacuo. The resulting oil was dissolved in THF (2.0 mL), allowed to cool to 0° C., and treated with an aqueous solution of $H_2O_2$ [$H_2O$ (2.0 mL), NaOH (326 mg, 8.156 mmol), and $H_2O_2$ (35 wt % solution in $H_2O$, 396 µL, 4.08 mmol)]. The biphasic mixture was allowed to warm to 22° C. over 30 min and stirred for 1 h. The mixture was diluted with EtOAc (5 mL) and the organic layer separated. The aqueous layer was washed with EtOAc (3×10 mL). The combined organic layers were dried over $K_2CO_3$, filtered, and concentrated. The resulting brown oil was purified by silica gel chromatography (5:1 hexanes:EtOAc) to afford 16 (178 mg, 0.520 mmol, 64.0% yield) as a white solid (98:2 er). 16 had been previously converted to C18 (plasm)-16:0 (PC) in four steps and 86% overall yield. M.P. 55-56° C.; IR (neat): 3326 (br), 2954 (s), 2917 (s), 2849 (s), 1663 (w), 1464 (w), 1378 (w), 1280 (w), 1150 (w), 1111 (w), 1055 (w); $^1$H NMR (400 MHz, CDCl$_3$): δ 5.94 (1H, dt, J=6.4, 1.3 Hz), 4.41 (1H, td, J=7.2, 6.4 Hz), 3.96-3.89 (1H, m), 3.83-3.72 (3H, m), 3.69-3.62 (1H, m), 2.46 (1H, d, J=4.4 Hz), 2.09-1.96 (3H, m), 1.38-1.13 (28H, m), 0.88 (3H, t, J=6.8 Hz); $^{13}$C NMR (100 MHz, CDCl$_3$): δ 144.6, 108.5, 73.4, 70.7, 63.8, 32.1, 29.9, 29.8, 29.7, 29.5, 29.5, 24.1, 22.8, 14.3; HRMS (ESL$^+$) [M+H]$^+$ calcd for $C_{21}H_{43}O_3$: 343.3212, found: 343.3219; $[α]^{20}_D$ [+1.39 (c 2.23 CHCl$_3$) for a sample of 98:2 er [S enantiomer Lit.[12]] $[α]^{20}_D$ [−1.65 (c 4.10, CHCl$_3$)]. The enantiomeric purity of 16 (98:2 e.r.) was determined by acylation to the corresponding bisbenzoate E (see below), and HPLC analysis in comparison with authentic racemic material. The absolute stereochemistry was determined through comparison to (R)-17 synthesized by Bittman et al.[12]

(S,Z)-3-(Octadec-1-en-1-yloxy)propane-1,2-diyl dibenzoate (E). Scheme 15 depicts the synthesis of (S,Z)-3-(octadec-1-en-1-yloxy)propane-1,2-diyl dibenzoate (E). A 5-mL round-bottom flask equipped with stir bar was charged with substrate 17 (20.0 mg, 0.0584 mmol), Et$_3$N (24.4 µL, 0.175 mmol), CH$_2$Cl$_2$ (584 µL), and was allowed to cool to 0° C. Benzoyl chloride (14.9 µL, 0.128 mmol) was added slowly over 1 minute. The mixture was allowed to stir for 1 h at 0° C., then 1 h at 22° C., and was then diluted with a saturated aqueous solution of sodium bicarbonate (2 mL), and EtOAc (5 mL). The organic layer was separated and the aqueous layer washed with EtOAc (2×5 mL). The combined organic layers were dried over anhydrous $K_2CO_3$, filtered, and concentrated. The resulting brown residue was purified by chromatography on silica gel (10:1 hexanes:EtOAc) to afford E (29.7 mg, 0.0539 mmol, 92.0% yield, >98% Z isomer) as a colorless oil. IR (Neat): 2922 (s), 2852 (s), 1723 (s), 1665 (w), 1602 (w), 1452 (m), 1378 (w), 1315 (m), 1259 (s), 1176 (m), 1106 (s), 1067 (m), 1026 (m); $^1$H NMR (400 MHz, CDCl$_3$): δ 8.08-8.00 (4H, m), 7.59-7.53 (2H, m), 7.47-7.39 (4H, m), 5.98 (1H, dt, J=6.4, 1.4 Hz), 5.63-5.58 (1H, m), 4.70 (1H, dd, J=12.0,4.0 Hz), 4.61 (1H, dd, J=12.0,6.4 Hz), 4.42 (1H, td, J=7.2,6.4 Hz), 4.10 (1H, dd, J=11.2,5.2 Hz), 4.06 (1H, dd, J=11.2,5.2 Hz), 2.09-2.01 (2H, m), 1.35-1.16 (28H, m), 0.88 (3H, t, J=6.8 Hz); $^{13}$C NMR (100 MHz, CDCl$_3$): δ 166:3, 165.9, 144.7, 133.4, 133.3, 130.0, 129.8, 129.8 128.6, 128.5, 108.8, 71.0, 70.1, 63.2, 32.1, 29.9, 29.8, 29.7, 29.5, 29.4, 24.0, 22.8, 14.3, 14.3; HRMS (ESI$^+$) [M+Na]$^+$ calcd for $C_{35}H_{50}O_5$Na. 573.3556, found: 573.3541; $[α]^D_{20}$ +5.79 (c 1.49 CHCl$_3$) for a sample of 98:2 er. As mentioned above, the enantiomeric purity of E (98:2 e.r.) was determined by HPLC analysis (Chiralpak OJ(H), 100% hexanes, 0.5 mL/min, 254 nm) in comparison with authentic racemic material.

Noteworthy is that the only previous synthesis of 16 involved nine transformations starting with (S)-isopropylidene glycerol (vs five reactions from (i-Pr)$_3$Si-acetylene, Scheme 13 by a sequence that included the use if highly toxic hexamethylphosphoramide and a catalytic hydrogenation with lead-containing salts. Also noteworthy is that the corresponding E isomer of the natural product has been shown to be less active.

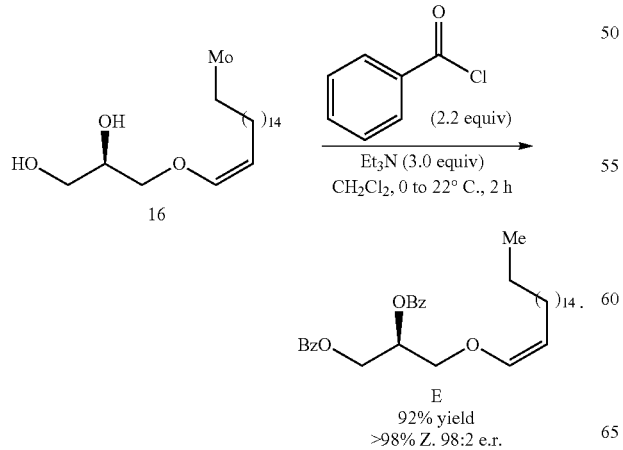

Scheme 15.

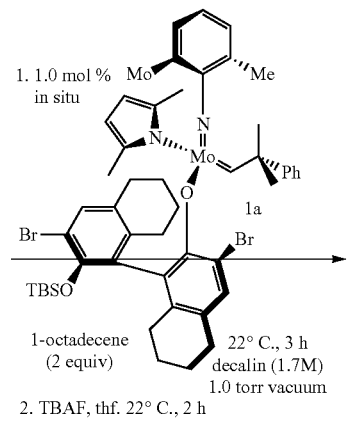

Scheme 16.

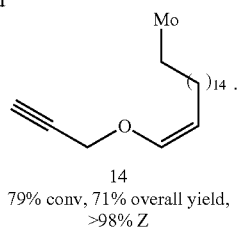

14
79% conv, 71% overall yield,
>98% Z

Gram Scale Cross-Metathesis of 11 with 1.0 mol % Mo Catalyst.

Scheme 16 depicts the cross metathesis of 11 on gram scale. Importantly, catalytic cross metathesis between 11 and 12 has been performed on gram-scale with 1.0 mol % of in situ-generated 1a and two equivalents of 12, affording Z-14 with >98% stereoselectivity and in 71% yield after purification (3 h, 1.0 torr, 79% cony). Following the exact same procedure described above, substrate 11 (1.00 g, 4.19 mmol) was treated with 1-octadecene (2.12 g, 8.39 mmol), decalin (2.10 mL), and 1.0 mol % of in situ-generated complex 1a (419 µL, 0.10 M, 41.9 µmol; final substrate concentration=1.7 M), and allowed to stir for 3 h under vacuum (1.0 torr). The unpurified product was >98% Z (as determined by 400 MHz $^1$H NMR analysis). Treatment with TBAF and purification on neutral alumina afforded compound 14 (0.9 14 g, 2.98 mmol, 71.0% yield, >98% Z isomer) as a white solid. The physical and spectral data were identical to those previously reported for enyne 14, detailed above.

Example 6

Catalytic Cross-Metathesis of Allylic Amines or Amides

Catalytic Cross-Metathesis of Allylic Amide 17 with Complex 1a. A second class of catalytic cross metathesis that was investigated involved reactions of allylic amines and their derivatives with terminal alkenes. These transformations pose the added complication that both substrates can undergo homocoupling. Preliminary investigations with enantiomerically pure allylic amide 17 (from commercially available alcohol) and 1-hexadecene 18, summarized in Table 5, indicated that the optimal catalyst for this class of processes is derived from adamantylimido complex 2, affording the desired Z alkene in 88% yield and with 97% stereoselectivity (entry 3).

TABLE 7

Catalytic Cross-Metathesis of Allylic Amide 17 with Complex 1a.

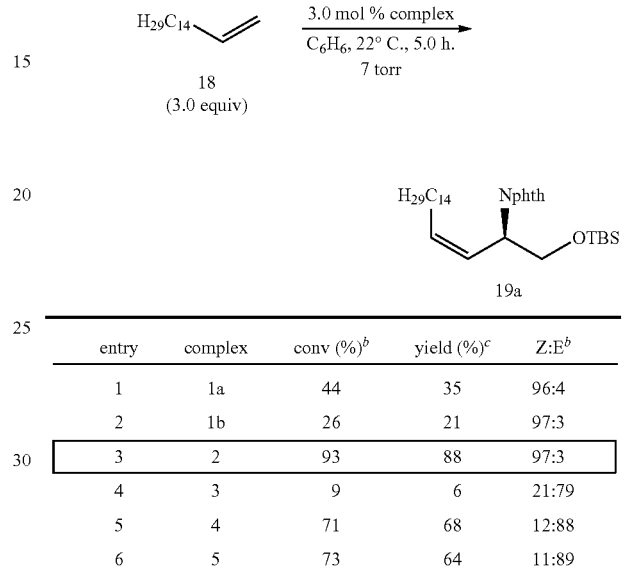

| entry | complex | conv (%)$^b$ | yield (%)$^c$ | Z:E$^b$ |
|---|---|---|---|---|
| 1 | 1a | 44 | 35 | 96:4 |
| 2 | 1b | 26 | 21 | 97:3 |
| 3 | 2 | 93 | 88 | 97:3 |
| 4 | 3 | 9 | 6 | 21:79 |
| 5 | 4 | 71 | 68 | 12:88 |
| 6 | 5 | 73 | 64 | 11:89 |

$^{a\text{-}c}$See Table 1.

Although arylimido derivatives 1a-b generate 19a with similar selectivity (entries 1-2, Table 7), conversions are lower (26-44% vs 88% cony). The higher efficiency of cross metathesis with 2, in contrast to those involving enol ethers (Table 3), might be the result of cross metathesis with 17 being performed under vacuum, allowing minimal amounts of the relatively unstable methylidene to be formed. Chiral complex 3 is less effective and achiral Mo alkylidene 4 and Ru carbene 5 furnish the E isomer predominantly (79-89%). A weaker vacuum (7.0 torr vs 1.0 torr for cross metathesis with enol ethers) is sufficient, indicating that such cross metathesis conditions can be applied to cases that involve relatively volatile substrates.

General Procedure for Catalytic Z-Selective Cross-Metathesis of Allylic Amides with Stereogenic-at-Mo Complexes: In an N$_2$-filled dry box, a 4-mL vial equipped with a magnetic stir bar was charged with allylic amide and in situ-generated Mo complex in C$_6$H$_6$. The second cross partner was then added by a syringe, and a septum, fitted with an outlet needle, was quickly attached to the vial. An adapter was attached to the top of the septum, and vacuum (7.0 torr) was applied. The resulting solution was allowed to stir under vacuum for the required period of time. The reaction vessel was removed from the dry box and the reaction was quenched by addition of benchtop Et$_2$O (~1 mL). The mixture was concentrated in vacuo (% conversion and diastereoselectivity determined by 400 MHz $^1$H NMR analysis). Purification was performed by silica gel chromatography. Results reported in the paper are averages of at least two independent runs, and the reactions reported below are representative of a single run.

TABLE 8

Synthesis of Z-1,2-Disubstituted Allylic Amides by Catalytic Cross Metathesis

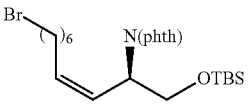

| 19b | 19c | 19d |
|---|---|---|
| 96% conv, 93% yield | 98% conv, 97% yield | 65% conv, 63% yield |
| 96% Z | 93% Z | 96% Z |

| 19e[b] | 19f[c] | 19g[c] |
|---|---|---|
| 65% conv, 65% yield | 80% conv, 75% yield | 87% conv, 87% yield |
| 97% Z | 81% Z | 85% Z |

[a]Performed with 3.0 mol % 2 and 3.0 equiv of non-N-containing cross partner; 7.0 torr, 5.0 h, 22° C.; conv and Z selectivities by $^1$H NMR analysis. Yields of pure Z isomers (±5%).
[b]Reduced pressure not used.
[c]Time = 1.0 h.

Various allylic amides and terminal alkenes, including those that contain a halide (cf. 19b), a Lewis basic group (cf. 19c-d) or a sterically demanding substituent (cf. 19e), were used in efficient Z-selective catalytic cross metathesis (Table 8). Stereoselective formation of 19f-g is noteworthy since the relatively less hindered unsaturated amides are more prone to homocoupling and the Z alkene products undergo equilibration to the E isomer more readily, as manifested by the lower Z:E ratios. Although in certain cases ten equivalents of a cross partner is used for maximum efficiency, lower amounts of alkene substrates can result in useful cross metathesis processes. For example, with 3.0 mol % 2 and three equivalents of the aliphatic alkene (vs. 5 mol % and 10 equiv), 19g was isolated in 62% yield and 90% Z selectivity (80% cony, 5.0 min, 22° C.).

Scheme 17.

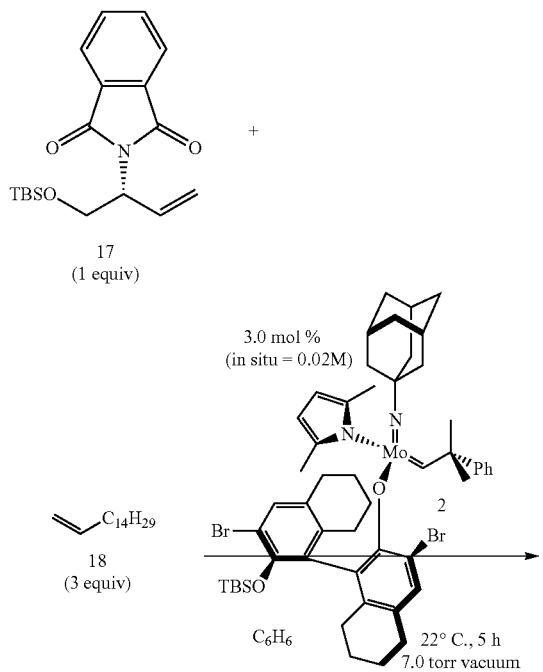

-continued

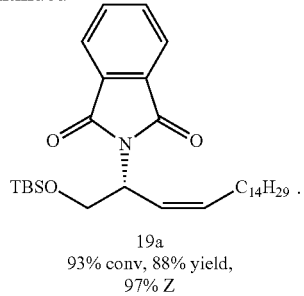

19a
93% conv, 88% yield,
97% Z (R,Z)-2-(1-((tert-Butyldimethylsilyl)oxy)octadec-3-en-2-yl)isoindoline-1,3-dione (19a). Following the allylic amide cross-metathesis general procedure, phthalimide 17 (19.0 mg, 0.0574 mmol) was treated with 1-hexadecene (49.0 µL, 0.17 1 mmol, 18), 3.0 mol % of in situ-generated complex 2 (86.0 µL, 0.02 M, 1.72 µmol), and allowed to stir under vacuum for 5 h. The unpurified product is 97% Z (as determined by 400 MHz $^1$H NMR analysis). The resulting brown oil was purified by silica gel chromatography (98:2 hexanes:EtOAc) to afford Z-19a (27.4 mg, 0.0520 mmol, 89.0% yield, 96% Z isomer) as a colorless oil. Z-19a: IR (neat): 2924 (s), 2853 (m), 1774 (w), 1713 (s), 1467 (m), 1386 (m), 1360 (m), 1333 (m), 1256 (m), 1107 (m), 1068 (m), 1018 (m), 838 (m); $^1$H NMR (400 MHz, CDCl$_3$): δ 7.9 (2H, dd, J=5.4, 3.0 Hz), 7.77 (2H, dd, J=5.8, 3.0 Hz) 5.96 (1H, ddt, J=10.8, 9.2, 1.6 Hz), 5.70 (1H, ddd, J=10.8, 7.4, 1.1 Hz), 5.27 (1H, ddd, J=10.0, 5.8, 0.9 Hz), 4.21 (1H, dd, J=10.0, 10.0 Hz), 3.82 (1H, dd, J=10.0, 5.6 Hz), 2.23 (2H, m), 1.35-1.22 (24H, m), 0.96 (3H, t, J=6.8 Hz), 0.83 (9H, s), 0.08 (3H, s), 0.01 (3H, s); $^{13}$C NMR (100 MHz, CDCl$_3$): δ 168.4, 136.0, 133.9, 132.3, 123.4, 123.2, 62.7, 50.5, 32.1, 29.9, 29.8, 29.8, 29.7, 29.7, 29.6, 29.5, 29.4, 27.9, 25.8, 25.8, 22.8, 18.1, 14.3, −5.3, −5.4; HRMS (ESI$^+$) [M+H]$^+$ calcd for C$_{32}$H$_{54}$NO$_3$Si 528.3873, found: 528.3851; [α]$^{20}_D$+15.8 (c 0.760, CDCl$_3$) for a sample of 98:2 e.r., 96:4 Z:E. E-19a: IR (neat): 2924 (m), 2853 (m), 1774 (w), 1711 (s), 1467 (m), 1387 (m), 1362 (m), 1333 (m), 1253 (m), 1172 (w), 1105 (w), 1064 (w), 1017 (w), 1006 (w), 971 (w), 909 (w), 874 (w), 836 (s), 814 (w), 776 (m), 757 (m), 718 (s), 668 (w), 649 (w), 530 (m), 405 (w); $^1$HNMR (400 MHz, CDCl$_3$): 8.9 (2H, dd, J=5.6, 3.2 Hz), 7.81 (2H, dd, J=5.4, 3.0 Hz), 5.94-5.81 (2H, m), 4.96-4.90 (1H, m), 4.21 (1H, dd, J=10.0, 10.0 Hz), 3.86 (1H, dd, J=10.0, 6.0 Hz), 2.09 (2H, dd, J=13.4, 7.0 Hz), 1.44-1.32 (24H, m), 0.96 (3H, t, J=6.8 Hz), 0.82 (9H, s), 0.07 (3H, s), 0.00 (3H, s); $^{13}$C NMR (100 MHz, CDCl$_3$): 8 168.5, 136.5, 133.9, 132.3, 123.8, 123.2, 62.8, 55.9, 32.5, 32.1, 29.9, 29.8, 29.8, 29.7, 29.6, 29.5, 29.3, 29.1, 25.8, 25.8, 22.8, 18.1, 14.3, −5.3, −5.4; HRMS (ESI$^+$) [M+Na]$^+$ calcd for C$_{32}$H$_{53}$NO$_3$SiNa: 550.3692, found: 550.3681; +0.64 (c 1.65, CDCl$_3$) for a sample of 98:2 e.r., 9:91 Z:E.

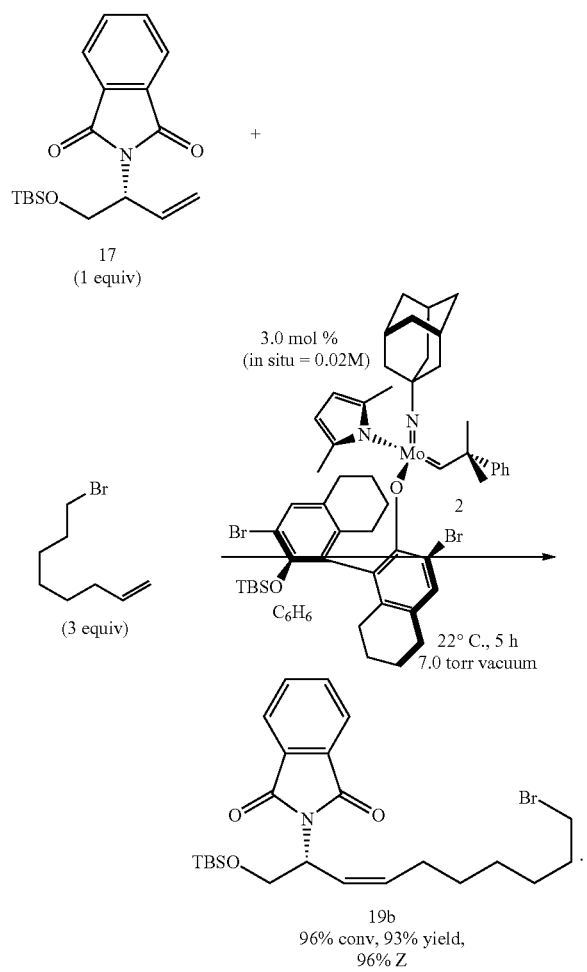

Scheme 18.

17
(1 equiv)

(3 equiv)

3.0 mol %
(in situ = 0.02M)

C$_6$H$_6$
22° C., 5 h
7.0 torr vacuum 19b
96% conv, 93% yield,
96% Z (R,Z)-2-(10-Bromo-1-((tert-butyldimethylsilyl)oxy)dec-3-en-2-yl)isoindoline-1,3-dione (19b). Following the allylic amide cross metathesis general procedure, phthalimide 17 (19.6 mg, 0.0637 mmol) was treated with 8-bromooctene (34.7 mg, 0.182 mmol), 3.0 mol % of in situ-generated complex 2 (95.0 μL, 0.02 M, 1.90 μmol), and allowed to stir under vacuum for 5 h. The unpurified product is 96% Z (as determined by 400 MHz $^1$H NMR analysis). The resulting brown oil was purified by silica gel chromatography (96:2:2 hexanes:EtOAc:CH$_2$Cl$_2$) to afford 19b (29.2 mg, 0.0590 mmol, 93.0% yield, 95% Z isomer) as a clear, colorless oil. IR (neat): 2928 (m), 2856 (m), 1773 (w), 1708 (s), 1468 (m), 1385 (m), 1358 (m), 1333 (m), 1255 (m), 1105 (m), 1065 (m), 1017 (w), 1006 (w), 836 (s), 717 (s); $^1$H NMR (400 MHz, CDCl$_3$): δ 7.76 (2H, dd, J=5.6, 2.8 Hz), 7.70 (2H, dd, J=5.6, 3.2 Hz), 5.84 (1H, dd, J=10.8, 9.2 Hz), 5.62 (1H, dt, J=10.8, 7.6 Hz), 5.18 (1H, dt, J=9.5, 6.0 Hz), 4.12 (1H, dd, J=9.8, 9.8 Hz), [diagnostic E isomer signal: 3.78 (1H, dd, J=12.0, 8.0 Hz)], 3.74 (1H, dd, J=10.2, 5.8 Hz), 2.17 (2H, ddd, J=14.2, 6.9, 1.2 Hz), 1.82-1.75 (2H, m), 1.43-1.24 (8H, m), 0.75 (9H, s), 0.01 (3H, s), −0.08 (3H, s); $^{13}$C NMR (100 MHz, CDCl$_3$): δ 168.4, 135.6, 134.0, 132.2, 123.8, 123.2, 62.6, 55.8, 50.4, 34.0, 32.8, 29.3, 28.4, 28.3, 28.2, 27.7, 25.8, 18.1, −5.3, −5.4; HRMS (ESI$^+$) [M+H]$^+$ calcd for C$_{24}$H$_{37}$BrNO$_3$: 496.1706, found: 496.1711; [α]$^{20}_D$+16.6 (c 1.88, CDCl$_3$) for a sample of 98:2 e.r., 95:5 Z:E.

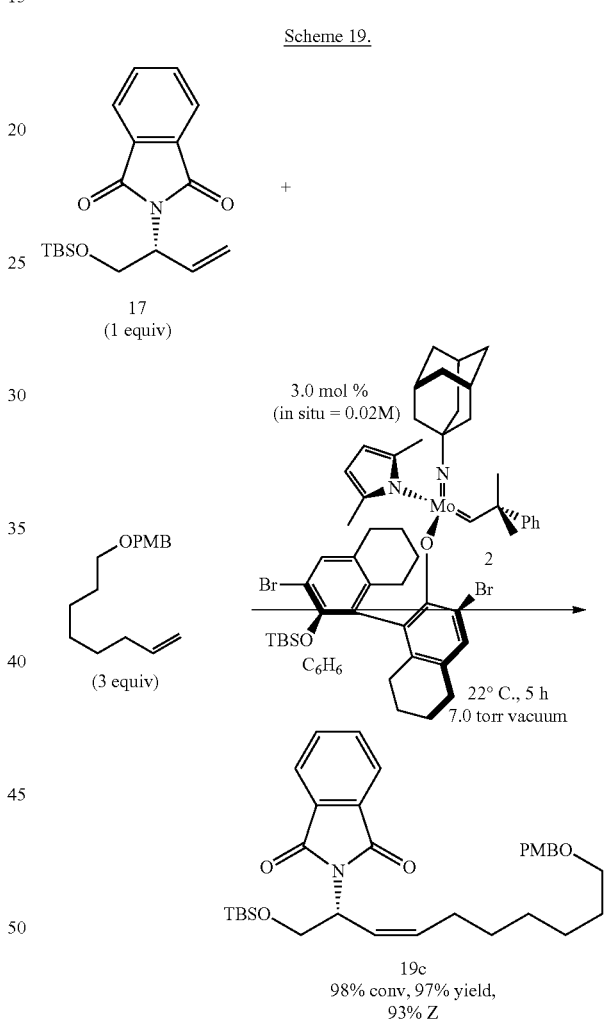

Scheme 19.

17
(1 equiv)

(3 equiv)

3.0 mol %
(in situ = 0.02M)

C$_6$H$_6$
22° C., 5 h
7.0 torr vacuum 19c
98% conv, 97% yield,
93% Z (R,Z)-2-(1-((tert-Butyldimethylsilyl)oxy)-10-((4-methoxybenzyl)oxy)dec-3-en-2-yl)isoindoline-1,3-dione (19 c). Following the allylic amide cross metathesis general procedure, phthalimide 17 (22.7 mg, 0.0690 mmol) was treated with 1-methoxy-4-((oct-7-en-1-yloxy)methyl)benzene (50.1 mg, 0.202 mmol), 3.0 mol % of in situ-generated complex 2 (102 μL, 0.02 M, 2.04 μmol), and allowed to stir under vacuum for 5 h. Z-selectivity could not be determined from 400 MHz $^{1H}$ NMR spectrum of unpurified product. The resulting brown oil was purified by silica gelchromatography (92:4:4 hexanes: EtOAc:CH$_2$Cl$_2$) to afford 19c (37.4 mg, 0.0680 mmol, 99.0% yield, 93% Z isomer) as a colorless oil.

IR (neat): 2927 (m), 2855 (m), 1773 (w), 1711 (s), 1613 (w), 1512 (m), 1466 (m), 1385 (m), 1358 (m), 1333 (m), 1301 (m), 1247 (m), 1172 (m), 1099 (s), 1037 (m), 1006 (m); $^1$HNMR (400 MHz, CDCl$_3$): δ 7.81 (2H, dd, J=5.2, 3.2 Hz), 7.68 (2H, dd, J=5.4, 3.0 Hz), 7.25 (2H, d, J=8.4 Hz), 6.87 (2H, d, J=8.4 Hz), 5.83 (1H, m), 5.63 (1H, m), 5.19 (1H, m), [diagnostic E isomer signal: 4.88-4.84 (1H, m)], 4.41 (2H, s), 4.12 (1H, dd, J=10.0, 10.0 Hz), 3.80 (3H, s), 3.73 (1H, dd, J=10.0, 5.6 Hz), 3.40 (2H, t, J=6.6 Hz), 2.15 (2H, dd, J=14.4, 7.2 Hz), 1.54 (2H, t, J=7.2 Hz), 1.35-1.26 (6H, m), 0.74 (9H, s), −0.01 (3H, s), −0.08 (3H, s); $^{13}$C NMR (100 MHz, CDCl$_3$): δ 168.4, 159.2, 135.8, 133.9, 132.2, 131.0, 129.4, 123.5, 123.2, 113.9, 72.6, 70.3, 62.6, 55.4, 50.5, 29.8, 29.5, 29.2, 27.8, 26.2, 25.8, 18.1, −5.3, −5.4; HRMS (ESI$^+$) [M−H]$^+$ calcd for C$_{32}$H$_{44}$NO$_5$Si: 550.2997, found: 550.2989; [α]$^{20}_D$+16.2 (c 2.09, CDCl$_3$) for a sample of 98:2 e.r., 93:7 Z:E.

(92:4:4 hexanes:EtOAc:CH$_2$Cl$_2$) to afford 19d (9.00 mg, 0.0189 mmol, 67.0% yield, 93% Z isomer) as a pale yellow oil. IR (neat): 2954 (w), 2928 (w), 2856 (w), 1761 (m), 1708 (s), 1492 (m), 1469 (m), 1385 (m), 1358 (m), 1334 (m), 1254 (m), 1195 (m), 1162 (m), 1127 (m), 1108 (m), 1068 (m), 1025 (m), 1005 (m), 836 (s), 718 (s); $^1$H NMR (400 MHz, CDCl$_3$): δ ™7.80(2H, dd, J=5.4, 3.0 Hz), 7.68 (2H, dd, J=5.6, 3.2 Hz), 7.33 (2H, m), 7.19 (1H, m), 7.04 (2H, dd, J=8.6, 1.0 Hz), 5.96 (1H, dd, 10.6, 10.0 Hz), 5.74-5.68 (1H, m), 5.24 (1H, m), [diagnostic E isomer signal: 4.92-4.86 (1H, m)], 4.13 (1H, t, J=9.8 Hz), 3.79 (1H, dd, J=10.2, 5.8 Hz), 2.64-2.62 (4H, m), 0.75 (9H, s), −0.01 (3H, s), −0.08 (3H, s); $^{13}$C NMR (100 MHz, CDCl$_3$): δ 170.6, 168.3, 150.8, 134.0, 133.0, 132.2, 129.5, 125.9, 125.5, 123.2, 121.7, 62.5, 50.3, 34.1, 25.8, 23.3, 18.1, −5.3, −5.5; HRMS (ESI$^+$) [M+H]$^+$ calcd for C$_{27}$H$_{34}$NO$_5$Si: 480.2206, found: 480.2193; [α]$^{20}_D$+ 18.2 (C 0.450, CDCl$_3$) for a sample of 98:2 e.r., 95:5 Z:E.

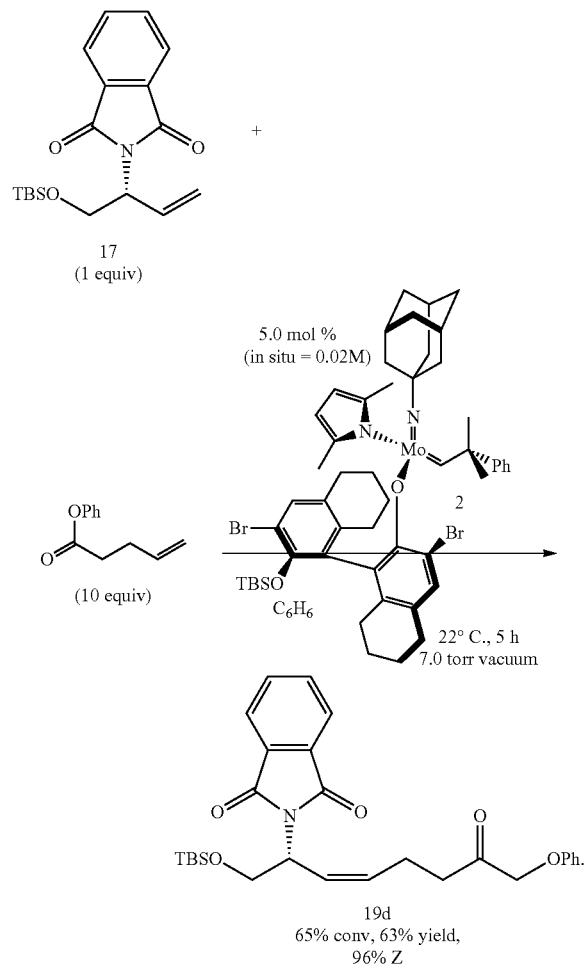

Scheme 20.

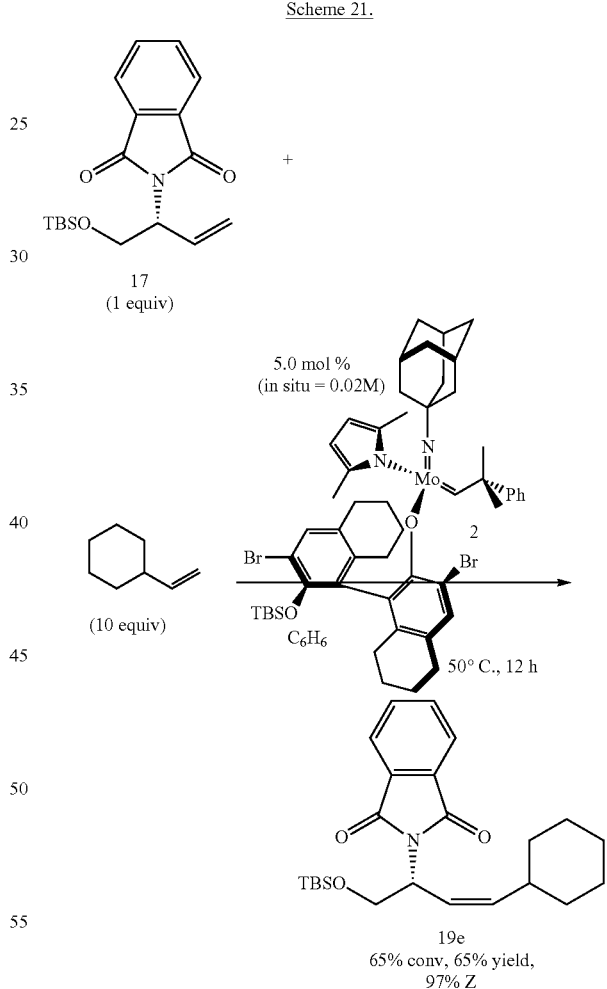

Scheme 21.

(R,Z)-phenyl 7-((tert-Butyldimethylsilyl)oxy)-6-(1,3-dioxoisoindolin-2-yl)hept-4-enoate (19d). Following the allylic amide cross metathesis general procedure, phthalimide 17 (9.30 mg, 0.028 1 mmol) was treated with phenyl pent-4-enoate (51.3 mg, 0.29 1 mmol), 5.0 mol % of in situ-generated complex 2 (65.0 !lL, 0.02 M, 1.30 µmol), and allowed to stir under vacuum for 5 h. The unpurified product is 96% Z (as determined by 400 MHz $^1$H NMR analysis). The resulting brown oil was purified by silica gel chromatography (R,Z)-2-(1-((tert-Butyldimethylsilyl)oxy)-4-cyclohexylbut-3-en-2-yl)isoindoline-1,3-dione (19e). Following the allylic amide cross metathesis general procedure, phthalimide 17 (11.4 mg, 0.0344 mmol) was treated with vinylcyclohexane (43.5 mg, 0.395 mmol), 5.0 mol % of in situ-generated complex 2 (85.0 µL, 0.02 M, 1.70 µmol), and allowed to stir for 12 h. The unpurified product is 97% Z (as determined by 400 MHz $^1$H NMR analysis). The resulting brown oil was purified by silica gel chromatography (96:2:2 hexanes: EtOAc:CH$_2$Cl$_2$) to afford 19e (8.60 mg, 0.0210 mmol, 61.0% yield, 94% Z isomer) as a clear, colorless oil. IR (neat): 2925 (m), 2853 (m), 1773 (w), 1709 (s), 1468 (m), 1385 (m), 1360 (m), 1333 (m), 1256 (w), 1103 (m), 1064 (m), 1005 (m), 835 (s), 717 (s); $^1$H NMR (500 MHz, CDCl$_3$): δ 7.82 (2H, dd, J=5.5, 3.0 Hz), 7.69 (2H, dd, J=5.5, 3.5 Hz), 5.73 (1H, ddd, J=10.4, 9.2, 0.8 Hz), 5.46 (1H, ddd, J=10.4, 10.4, 0.8 Hz), 5.21 (1H, td, 9.3, 5.5 Hz), [diagnostic E isomer signal: 4.84-4.82 (1H, m)], 4.12 (1H, t, J=10.0 Hz), 3.73 (1H, dd, J=10.0, 6.0 Hz), 2.48-2.41 (1H, m), 1.73-1.63 (3H, m), 1.55-1.48 (1H, m), 1.38-1.25 (3H, m), 1.19-0.99 (3H, m), 0.75 (9H, s), 0.00 (3H, s), 0.07 (3H, s); $^{13}$C NMR (100 MHz, CDCl3): δ 168.4, 141.6, 133.9, 132.2, 123.2, 121.4, 62.9, 50.8, 36.9, 33.5, 33.1, 26.1, 25.8, 25.8, 25.7, 18.2, −5.3, −5.4; HRMS (ESI$^+$) [M+H]$^+$ calcd for C$_{24}$H$_{36}$NO$_3$Si: 414.2464, found: 414.2465; $[α]^{20}_D$+28.3 (c 0.630, CDCl$_3$) for a sample of 98:2 e.r., >98:2 Z:E.

Scheme 22.

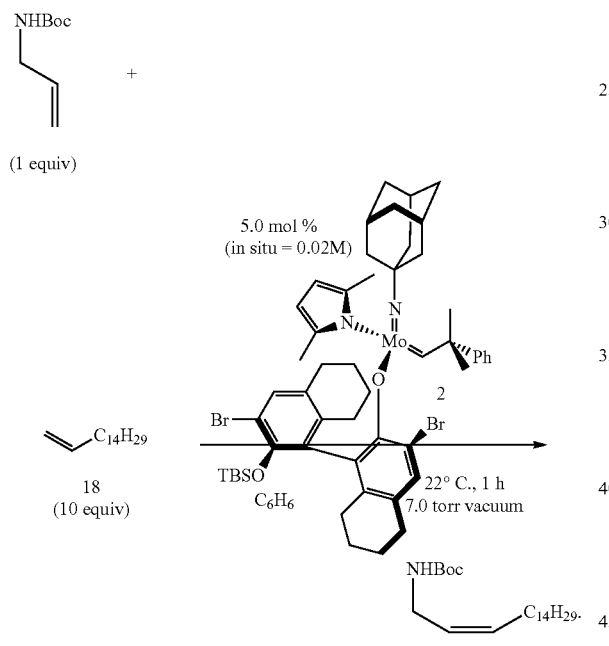

19f
80% conv, 75% yield,
81% Z (Z)-tert-Butyl heptadec-2-en-1-ylcarbamate (19f). Following the allylic amide CM general procedure, tert-butyl allylcarbamate (4.40 mg, 0.0280 mmol) was treated with 1-hexadecene (64.5 mg, 0.290 mmol), 5.0 mol % of in situ-generated complex 2 (75.0 µL, 0.02 M, 1.50 µmol), and allowed to stir under vacuum for 1 h. Z-selectivity could not be determined from 400 MHz $^1$H NMR spectrum of unpurified product. The resulting brown oil was purified by silica gel chromatography (96:2:2 hexanes:EtOAc:CH$_2$Cl$_2$) to afford 19f (8.30 mg, 0.0230 mmol, 84.0% yield, 81% Z isomer) as a white, crystalline solid. M.P. 42-46° C.; IR (neat): 3353 (br), 2922 (s), 2853 (s), 1700 (s), 1501 (m), 1457 (m), 1390 (m), 1365 (m), 1247 (m), 1170 (s), 1046 (w), 1023 (w); $^1$H NMR (400 MHz, CDCl$_3$): 5.60-5.34 (overlapping Z/E 2H, m), 4.45 (overlapping Z/E, 1H, br d, J=15.6 Hz), 3.74 (E, 1H, br s), 3.66 (Z, 1H, br s), 2.06-1.96 (overlapping Z/E, 2H, m), 1.43 (overlapping Z/E, 9H, s), 1.41-1.24 (overlapping Z/E, 24H, m), 0.86 (overlapping Z/E, 3H, t, J=7.8 Hz); $^{13}$C NMR (100 MHz, CDCl$_3$): 156.0, 155.9, 133.4, 126.3, 125.9, 79.4, 77.4, 32.4, 32.1, 29.9, 29.8 29.8, 29.8, 29.7, 29.7, 29.5, 29.4, 29.3, 28.6, 27.5, 22.8, 19.2, 14.3; HRMS (ESI$^+$) [M+Na]$^+$ calcd for C$_{22}$H$_{43}$NO$_2$Na: 376.3191, found: 376.3184.

Scheme 23.

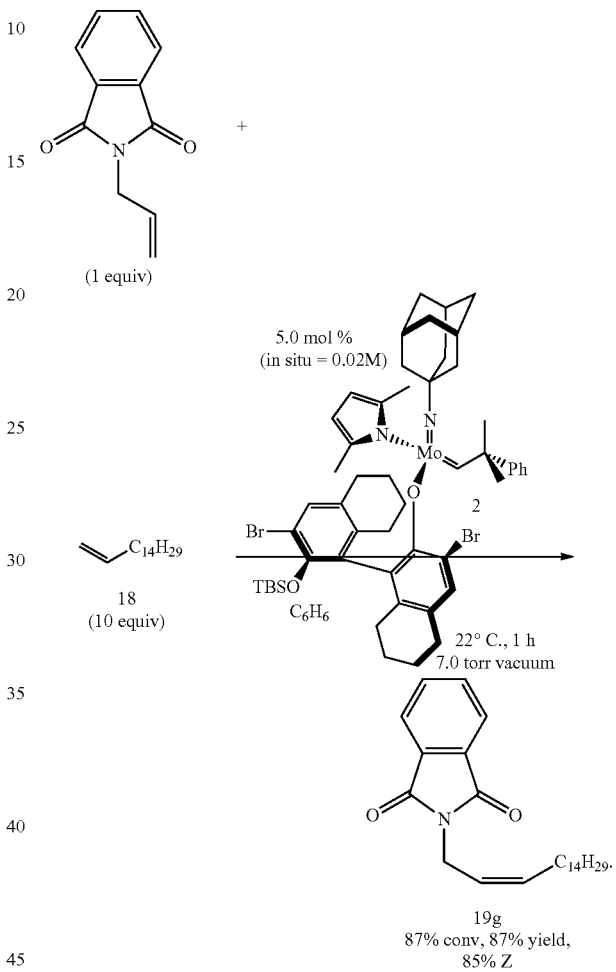

19g
87% conv, 87% yield,
85% Z (Z)-2-(Heptadec-2-en-1-yl)isoindoline-1,3-dione (19g). Following the allylic amide cross metathesis general procedure, 2-allylisoindoline-1,3-dione (5.50 mg, 0.0290 mmol) was treated with 1-hexadecene (63.8 mg, 0.290 mmol), 5.0 mol % of in situ-generated complex 2 (75.0 µL, 0.02 M, 1.50 i&mol; final substrate concentration=0.19 M) and allowed to stir for 1 h. The unpurified product is 85% Z (as determined by 400 MHz $^1$H NMR analysis). The resulting brown oil was purified by silica gel chromatography (96:2:2 hexanes: EtOAc:CH$_2$Cl$_2$) to afford 19g (9.80 mg, 0.0260 mmol, 87.0% yield, 85% Z isomer) as a white, crystalline solid. M.P. 56-60° C.; IR (neat): 2954(w), 2916 (s), 2849 (m), 1771 (w), 1698 (s), 1614 (w), 1464 (m), 1429 (m), 1400 (m), 1356 (w), 1335 (w), 1294 (w), 1189 (w), 1173 (w), 1155 (w), 1089 (w), 1071 (w), 1052 (w), 1024 (w), 962 (m), 930 (m); $^1$H NMR (400 MHz, CDCl$_3$): 7.84 (2H, dd, J=5.4, 3.0 Hz), 7.70 (2H, dd, J=5.4, 3.0 Hz), 5.78-5.71 (1H, m), 5.54-5.44 (1H, m), 4.23 (2H, dd, J=6.2, 0.8 Hz), [diagnostic E isomer signal: 4.22 (1H, d, J=8 Hz)], 1.99 (2H, dd, J=13.6, 6.8 Hz), 1.43-1.19 (24H, m), 0.88 (3H, t, J=6.8 Hz); $^{13}$C NMR (100 MHz, CDCl$_3$): 168.2, 135.6, 134.0, 132.4, 123.4, 123.3, 123.1, 77.4, 39.8, 32.3, 32.1, 29.9, 29.8, 29.8, 29.7, 29.7, 29.6, 29.6, -29.5, 29.3, 29.0, 22.8, 14.3; HRMS (ESI$^+$) [M+H]$^+$ calcd for C$_{25}$H$_{38}$NO$_2$: 384.2903, found: 384.2905.

Synthesis of Selected Substrates for Cross Metathesis Reactions:

Dec-9-en-1-ynyltrimethylsiktne. A 250-mL round-bottom flask equipped with a stir bar and a water-jacketed reflux condenser was charged with trimethylsilylacetylene (6.00 mL, 42.0 mmol). THF (50 mL) was added, and the mixture was allowed to cool to 0° C. (ice-bath). nButyllithium (29.0 mL, 42.0 mmol, 1.46 M solution in hexanes) was added dropwise by a syringe, and the ice-bath was removed following the addition. The mixture was allowed to warm to 22° C. as it stirred for 1 h, at which point 8-bromo-1-octene (3.50 mL, 21.0 mmol) was added, and the mixture was allowed to reflux for 12 h. The mixture was allowed to cool to 0° C., quenched by addition of 50 mL water, washed with CH$_2$Cl$_2$ (5×50 mL). The combined organic layers were washed in brine (1×50 mL), dried over MgSO$_4$, filtered, and concentrated in vacuo. The resulting brown oil was filtered through a plug of silica gel (eluted in pentane), the filtrate was concentrated and the resulting brown oil distilled under vacuum (1.0 torr). The resulting yellow oil was re-distilled under vacuum (1.0 ton) to afford dec-9-en-1-ynyltrimethylsilane (0.700 g, 3.40 mmol, 14.0% yield) as a colorless oil. IR (neat): 3078 (w), 2929 (m), 2857 (w), 2175 (m), 1641 (w), 1461 (w), 1325 (w), 1248 (m), 1032 (w), 994 (w), 910 (m), 837 (s), 758 (s), 725 (w), 697 (w), 638 (m), 575 (w), 450 (w); $^1$H NMR (400 MHz, CDCl$_3$): δ 5.86-5.76 (1H, m), 4.99 (1H, dd, J=17.2, 2.0 Hz), 4.93 (1H, dd, J=10.0,0.8 Hz), 2.21 (2H, t, J. 7.2 Hz), 2.05 (2H, app q, J=7.1 Hz), 1.55-1.48 (2H, m), 1.40-1.28 (6H, m), 0.14 (9H, s); $^{13}$C NMR (100 MHz, CDCl$_3$): δ 139.2, 114.4, 107.8, 84.4, 33.9, 28.9, 28.8, 28.7, 28.7, 20.0, 0.3; HRMS (ESI$^+$) [M+H]$^+$ calcd for C$_{13}$H$_{25}$Si: 209.1726, found: 209.1719.

1-Methoxy-4-((oct-7-en-1-yloxy)methyl)benzene. A 250 mL round-bottom flask equipped with stir bar was charged with 7-octen-1-ol (1.20 mL, 7.80 mmol). Anhydrous DMF (60 mL) was added, and the solution was allowed to cool to 0° C. (ice-bath). Sodium hydride (2.40 g, 40.0 mmol) was added in portions, and the mixture was allowed to stir until gas evolution ceased. p-Methoxybenzyl chloride (2.1 mL, 16 mmol) was added by a syringe and the mixture was allowed to stir for 24 h. The reaction was quenched by addition of a saturated aqueous solution of sodium bicarbonate (100 mL), and washed with ethyl acetate (5×100 mL). The combined organic layers were washed with water (3×100 mL) to remove dmf, further washed in brine (1×50 mL), dried over MgSO$_4$, filtered, and concentrated in vacuo. The resulting yellow oil was purified by silica gel chromatography (96:4 hexanes: EtOAc), delivering 1-methoxy-4-((oct-7-en1-yloxy)methyl) benzene (946 mg, 3.81 mmol, 49.0% yield) as a colorless oil. IR (neat): 3074 (w), 2998 (m), 2929 (m), 2854 (w), 1640 (m), 1613 (w), 1586 (w), 1511 (m), 1463 (m), 1441 (w), 1361 (w), 1301 (m), 1245 (s), 1208 (w), 1172 (m), 1095 (s), 1036 (s), 995 (w), 909 (m), 819 (s), 755 (w), 727 (w), 707 (w), 637 (w), 571 (w), 513 (w), 418 (w); $^1$H NMR (400 MHz, CDCl$_3$): δ 7.25 (2H, d, J=8.8 Hz), 6.87 (2H, d, J=8.4 Hz), 5.80 (1H, m), 4.98 (1H, dd, J=17.2, 2.0 Hz), 4.92 (1H, dd, J=10.0, 2.4 Hz), 4.42 (2H, s), 3.79 (3H, s), 3.43 (2H, t, J=6.6 Hz), 2.03 (2H, app q, J=6.9 Hz), 1.63-1.56 (2H, m), 1.41-1.27 (6H, m); $^{13}$C NMR (100 MHz, CDCl$_3$): δ 159.2, 139.2, 130.9, 129.3, 114.3, 113.8, 72.6, 70.3, 55.3, 33.8, 29.8, 29.1, 29.0, 26.2; HRMS (ESI$^+$) [M+NH$_4$]$^+$ calcd for C$_{16}$H$_{28}$NO$_2$: 266.2120, found: 266.2130.

(R)-2-(1-((tert-butyldimethylsilyl)oxy)but-3-en-2-yl) isoindoline-1,3-dione (17). A 50-mL round-bottom flask equipped with stir bar was charged with (R)—N-phthaloyl-2-aminobut-3-en-1-ol (1.49 g, 6.88 mmol) and imidazole (720 mg, 10.6 mmol). A separate oven-dried 50-mL flask equipped with a stir bar was charged with tert-butyldimethylsilyl chloride (2.20 g, 14.6 mmol) and anhydrous DMF (15 mL); the mixture was allowed to stir until all solids were dissolved. The solution of silyl chloride was transferred by syringe to the alcohol and imidazole. The resulting mixture was allowed to stir for 48 h at 22° C. The reaction was quenched by addition of water (50 mL) and washed with ethyl acetate (5×50 mL). The combined organic layers were washed with H$_2$O (3×100 mL) to remove residual DMF, further washed with brine (1×50 mL), dried over MgSO$_4$, filtered, and concentrated in vacuo. The resulting yellow oil was purified by silica gel chromatography (95:5 hexanes: EtOAc) to afford 17 (1.89 g, 5.71 mmol, 83.0% yield) as a colorless oil. Upon azeotropic drying with anhydrous benzene 17 was obtained as a white crystalline solid. M.P. 39-40° C.; IR (neat): 2953 (w), 2931 (w), 2857 (w), 1769 (w), 1704 (s), 1612 (w), 1595 (w), 1466 (m), 1425 (w), 1386 (s), 1361 (s), 1335 (w), 1292 (w), 1256 (m), 1188 (w), 1173 (w), 1102 (s), 1067 (w), 1029 (w), 1005 (w), 938 (m), 887 (w), 836 (s), 796 (w), 774 (m), 723 (w), 715 (s), 699 (w), 673 (m), 611 (w), 531 (m), 417 (w); $^1$H NMR (400 MHz, CDCl$_3$): δ 7.83 (2H, dd, J=5.2, 3.2 Hz), 7.70 (2H, dd, J=5.4, 3.0 Hz), 6.17 (1H, ddd, J=17.2, 10.4, 7.2 Hz), 5.30 (1H, d, J=17.2 Hz), 5.24 (1H, dd, J=10.4, 0.8 Hz), 4.93-4.87 (1H, m), 4.15 (1H, t, J=9.8 Hz), 3.85 (1H, dd, J=10.0, 6.0 Hz), 0.74 (9H, s), 0.01 (3H, s), -0.08 (3H, s); $^{13}$C NMR (100 MHz, CDCl$_3$): δ 168.4, 134.0, 132.4, 132.1, 123.2, 119.1, 62.3, 56.0, 25.7, 18.1, -5.3, -5.5; CDCl$_3$) HRMS (ESI$^+$) [M+H]$^+$ calcd for C$_{18}$H$_{26}$NO$_3$Si: 332.1682, found: 332.1680; [α]$^{20}$$_D$+13.4 (c 0.730 CDCl$_3$) for a sample of 98:2 e.r. The enantiomeric purity of starting alcohol (R)—N-Phthaloyl-2-aminobut-3-en-1-ol (98:2 e.r.) was determined by HPLC analysis (Chiralpak AS(H), 95:5 hexanes: isopropanol, 0.5 mL/min, 254 nm) in comparison with authentic racemic material.

Phenyl pent-4-enoate. A 250-mL round-bottom flask equipped with a stir bar was charged with 4-pentenoic acid (5.10 mL, 50.0 mmol) and CH$_2$Cl$_2$ (40 mL), followed by thionyl chloride (4.00 mL, 55.0 mmol). The mixture was allowed to stir for 30 min, at which point phenol (9.45 g, 100 mmol) was added as a solution in CH$_2$Cl$_2$ (10 mL). The mixture was allowed to cool to 0° C. (ice-bath), and triethylamine (28 mL, 200 mmol) was added dropwise by a syringe over 5 min (N.B., strong exotherm). The resulting solution was allowed to stir for 12 h at 22° C. The reaction was quenched by addition of a saturated aqueous solution of NaHCO$_3$ (100 mL). The organic layer was separated, and the aqueous layer washed with CH$_2$Cl$_2$ (5×50 mL). The combined organic layers were washed with water (1×50 mL), brine (1×50 mL), dried over MgSO$_4$, filtered, and concentrated in vacuo. The resulting oil was purified by silica gel chromatography (95:5 hexanes:EtOAc) to deliver a colorless oil. The oil was distilled from CaH$_2$ under reduced pressure (1.0 torr) to afford phenyl(4-pentenoate) (2.58 g, 14.6 mmol, 29.0% yield) as a colorless oil. Spectral data matched those in the literature.

Figure 4:
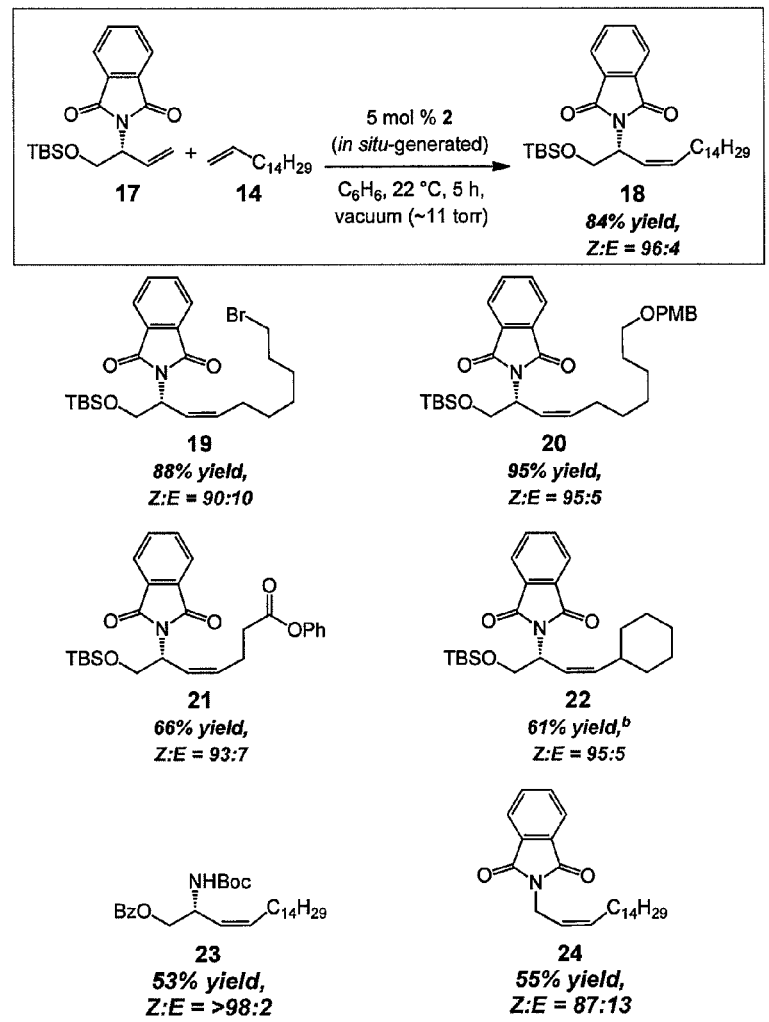
FIG. 4 shows the stereoselective synthesis of various Z-allylic amines.

As described above and herein, methods of the present invention can be readily applied to a variety of cross metathesis reactions of allylic amines and/or allylic amides. Exemplary such reactions are summarized in FIG. 4. Particularly noteworthy is the cross metathesis of sterically congested α-branched vinylcyclohexane with an equally hindered α-substituted allylic amide 17 to afford phthalimide 22 with reasonable efficiency (61% yield) using methods of the present invention. Z-selectivity remained high (95% Z) in spite of the sizeable substituents of the cis alkene. Highly stereoselective formation of Boc-amide 23 demonstrated that methods of the present invention can be extended to N-containing alkenes that bear other useful protecting groups. The relatively lower selectivity obtained with terminal phthalimide 24 (87% Z) may be, at least partly, attributed to a more facile reaction of a Mo alkylidene with Z-24, establishing partial equilibration. Two points regarding the transformations in FIG. 4 merit mention. First, all reactions (except for 22) were performed under vacuum (~11 torr). When reactions were performed under ambient conditions, cross metathesis processes were significantly less efficient. For example, synthesis of 18 proceeded to only 48% conversion (41% yield, >98% Z vs 92% conv, 84% yield and >98% Z) when reduced pressure was not applied. Second, in the presence of 5 mol % Mo-based alkylidenes 1a and 1b, reactions proceeded with equally high levels of stereoselectivity but with substantially lower efficiency (e.g., ~25% conversion for formation of 18 with complex 1b).

Example 8

Application to Stereoselective Synthesis of Phytosphingosine

Figure 5:
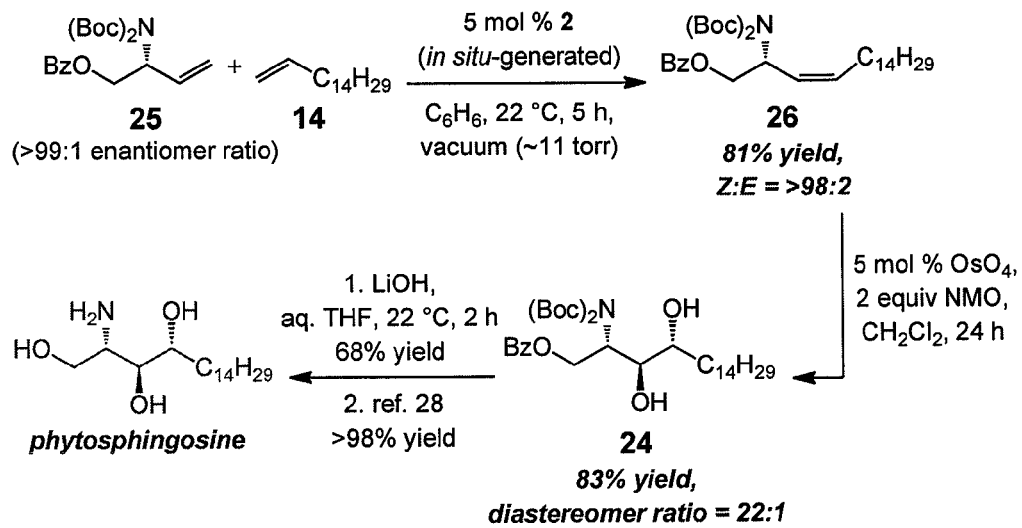
FIG. 5 shows the synthesis of phytosphingosine using a Z-selective cross-metathesis reaction.

As shown in FIG. 5, methods of the present invention may further provide the opportunity for the design of expeditious routes for preparation of enantiomerically pure phytosphingosine, a sphingolipid found in the human kidney, liver, and intestine (FIG. 5) in a highly diastereoselective manner. Mo-catalyzed cross-metathesis of enantiomerically pure bis-Boc allylic amide 25 with 1-hexadecene delivered disubstituted alkene 26 in 81% yield after purification exclusively as a Z olefin isomer (>98% Z). Subsequent dihydroxylation proceeded diastereoselectively (22:1 dr) to afford 26 in 83% yield. Phytosphingosine was then obtained after two straight-forward operations (unmasking of terminal carbinol and secondary amine).

Example 9

Application to Stereoselective Synthesis of KRN7000

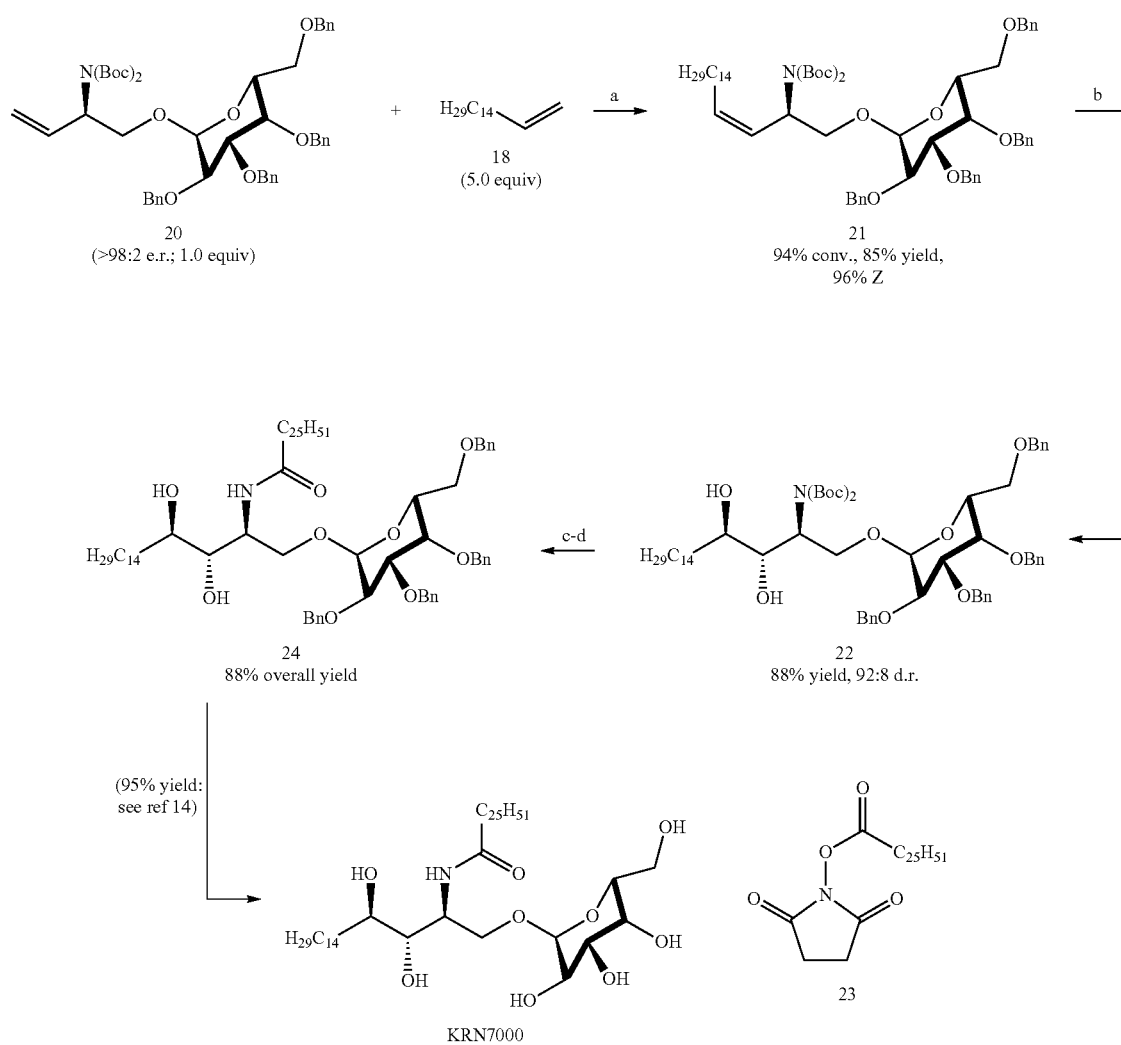

Scheme 24.

Conditions: (a) 8.0 mol % 2 (in situ-generated), $C_6H_6$, 22° C., 5.0 h, 1.0 torr. (b) 5 mol % $OsO_4$, 2.5 equiv N-Me-morpholine oxide, $CH_2Cl_2$, 22° C., 24 h. (c) 10% trifluoroacetic acid, $CH_2Cl_2$, 22° C., 30 min. (d) 1.2 equiv 23, $Et_3N$, THF, 50° C., 12 h.

Stereoselective synthesis of KRN7000 underlines the utility of methods of the present invention (Scheme 24). Catalytic cross metathesis of carbohydrate-containing allylic amide 20, prepared in four steps from commercially available agents, afforded 21 in 87% yield and >98% Z selectivity. Diastereoselective dihydroxylation (92:8 diastereomeric ratio) of the Z alkene delivered the desired product 22. Dihydroxylamide 24 was secured in two steps and the desired target was obtained after carbohydrate deprotection. It should be noted that Z-selective cross metathesis provides access to a route that is significantly more concise than the 14-step sequence (vs steps) reported thus far as the shortest synthesis of KRN7000.

Allylic phthalimide G. Allylic phthalimide G was prepared by a modified literature procedure. An oven-dried 100-mL round-bottom flask equipped with a stir bar was charged with D-2,3,4,6-tetra-O-benzylgalactose (979 mg, 1.79 mmol), triphenylphosphine (1.39 g, 5.30 mmol), carbon tetrabromide (1.91 g, 5.76 mmol), and anhydrous DMF (20 mL). The resulting red-orange mixture was allowed to stir for 5 h at 22° C. (R)—N-Phthaloyl-2-aminobut-3-en-1-ol (1.19 g, 5.48 mmol) was added, and the resulting mixture was allowed to stir for 12 h at 22° C. The mixture was then diluted by addition of ethyl acetate (20 mL) and a saturated aqueous solution of sodium bicarbonate (40 mL). The organic layer was separated and the aqueous layer washed with ethyl acetate (5×20 mL). The combined organic layers were washed with water (3×10 mL), brine (1×20 mL), dried over MgSO$_4$, filtered, and concentrated in vacuo to deliver an amber oil. $^1$H NMR (400 MHz) analysis of the unpurified product revealed a mixture of α:β anomers (approx. 3:1 α:β). The desired α-anomer was separated by silica gel chromatography (85:15 hexanes:EtOAc) to afford allylic phthalimide G (1.00 g, 1.36 mmol, 76.0% yield) as a pale yellow viscous oil (>98:2 α:β). IR (neat): 3063 (w), 3029 (w), 2916 (w), 2872 (w), 1774 (w), 1708 (s), 1610 (w), 1496 (w), 1467 (w), 1453 (w), 1384 (m), 1357 (w), 1207 (w), 1154 (w), 1133 (w), 1093 (m), 1044 (m), 1027 (w), 991(w), 883 (w), 869 (w), 719 (s), 695 (s), 666 (w), 609 (w), 530 (w), 461 (w); $^1$H NMR (400 MHz, CDCl$_3$): δ 7.74 (2H, dd, J=5.4, 3.0 Hz), 7.61 (2H, dd, J=5.4, 3.0 Hz), 7.35-7.27 (15H, m), 7.21-7.19 (3H, m), 7.12-7.09 (2H, m), 6.18 (1H, ddd, J=17.4, 10.4,6.0 Hz),5.33 (1H, dt, J=17.2, 1.2 Hz),5.27 (1H,dd,J=10.4, 1.0 Hz), 5.12-5.06 (1H, m), 4.90 (1H, d, J=11.6 Hz), 4.83 (1H, d, J=3.2 Hz), 4.64 (1H, d, J=12.0 Hz), 4.58 (1H, d, J=11.6 Hz), 4.54 (1H, d, J=11.6 Hz), 4.52 (1H, d, J=12.0 Hz), 4.43 (1H, d, J=12.0 Hz), 4.42 (1H, d, J=12.4 Hz), 4.36 (1H, d, J=12.0 Hz), 4.12 (1H, t, J=9.8 Hz), 4.02-3.98 (2H, m), 3.93-3.90 (2H, m), 3.82 (1H, dd, J=10.4, 2.8 Hz), 3.54 (2H, dd, J=6.4, 1.6 Hz); $^{13}$C NMR (100 MHz, CDCl$_3$):δ 168.4, 138.9, 138.8, 138.7, 138.2, 133.8, 132.2, 132.1, 128.5, 128.4, 128.3, 128.3, 128.2, 127.9, 127.8, 127.6, 127.6, 127.5, 127.5, 127.3, 123.0, 119.2, 98.4, 78.8, 76.2, 75.3, 74.8, 73.5, 73.3, 72.4, 70.0, 69.1, 67.4, 53.6; HRMS (ESI$^+$) [M+Na]$^+$ calcd for C$_{46}$H$_{45}$NO$_8$Na: 762.3043, found: 762.3047; [α]$^{20}_D$+21.1 (c 2.72, CDCl$_3$) for a sample of 98:2 e.r (e.r. measured for (R)—N-phthaloyl-2-aminobut-3-en-1-ol).

Allylic amine H. Amine H was prepared by a modified literature procedure. A 100-mL roundbottom flask equipped with a stir bar and condenser was charged with glycoside G (646 mg, 0.873 mmol), ethylenediamine (175 μL, 2.62 mmol), and anhydrous ethanol (17 mL). The resulting colorless solution was allowed to stir at reflux for 12 h; during the course of the reaction white solids precipitated. The white suspension was concentrated under reduced pressure to yield an opaque white residue. The resulting white residue was purified by silica gel chromatography (wet-loaded in methanol/CH2Cl$_2$ (1:1), and eluted with 90:10 methanol:EtOAc), to afford amine H (521 mg, 0.855 mmol, 98.0% yield) as a pale, yellow oil. IR (neat): 3063 (w), 3030 (w), 2914 (w), 2866 (w), 1586 (w), 1496 (w), 1454 (m), 1347 (w), 1266 (w), 1207 (w), 1156 (w), 1132 (w), 1094 (s), 1041 (s), 1028 (w), 993 (w), 917 (w), 842 (w), 732 (s), 695 (s), 601 (w), 550 (w), 460 (w); $^1$H NMR (400 MHz, CDCl$_3$): δ 7.38-7.27 (13H, m), 7.25-7.22 (7H, m), 5.77 (1H, ddd, J=17.4, 10.6, 4.4 Hz), 5.21 (1H, ddd, J=17.2, 1.2, 1.2 Hz), 5.08 (1H, ddd, J=10.4, 1.4, 1.4 Hz), 4.93 (1H, d, J=11.6 Hz), 4.89 (1H, d, J=4.0 Hz), 4.82 (1H, d, J=11.6 Hz), 4.78 (1H, d, J=12.0 Hz), 4.73 (1H, d, J=11.2 Hz), 4.66 (1H, d, J=11.6 Hz), 4.56 (1H, d, J=11.6 Hz), 4.46 (1H, d, J=11.6 Hz), 4.38 (1H, d, J=11.6 Hz), 4.04 (1H, dd, 10.0, 3.6 Hz), 3.96-3.91 (3H, m), 3.67 (1H, dd, J=9.6, 4.0 Hz), 3.62-3.57 (1H, m), 3.52 (2H, dd, J=6.6, 1.4 Hz), 3.21 (1H, dd, J=9.6, 8.4 Hz), 1.50 (2H, br s); $^{13}$C NMR (100 MHz, CDCl$_3$): δ 138.9, 138.8, 138.7, 138.1, 128.5, 128.5, 128.5, 128.4, 128.0, 127.9, 127.8, 127.7,127.7, 127.6, 115.6, 98.9, 79.2, 75.1, 74.9, 73.9, 73.6, 73.4, 73.2, 69.7, 69.2, 54.1; HRMS (ESI$^+$) [M+Na]$^+$ calcd for C$_{38}$H$_{43}$NO$_6$Na: 632.2988, found: 632.2987; [α]$^{20}_D$+33.2 (c 2.47, CDCl$_3$) for a sample of 98:2 e.r. (e.r. measured for (R)—N-phthaloyl-2-aminobut-3-en-1-ol).

Allylic Boc-amide I. An oven-dried 12-mL vial equipped with a stir bar was charged with amine H (203 mg, 0.333 mmol), Boc$_2$O (441 mg, 2.02 mmol), and CH$_2$Cl$_2$ (5 mL). Triethylamine (1.3 mL) was added and the reaction mixture was allowed to stir for 12 h at 22° C. The resulting solution was concentrated in vacuo, and the resulting pale yellow oil was purified by silica gel chromatography (80:20 hexanes: EtOAc), to a deliver amide I (201 mg, 0.283 mmol, 85.0% yield) as a colorless oil. IR (Neat): 3353 (w), 3064 (w), 3031 (w), 2924 (w), 2868 (w), 1711 (s), 1645 (w), 1605 (w), 1496 (m), 1454 (m), 1391 (w), 1365 (m), 1345 (w), 1245 (w), 1208 (w), 1159 (s), 1135 (w), 1095 (s), 1042 (s), 1028 (w), 990 (w), 910 (s), 849 (w), 818 (w), 731 (s), 696 (s), 647 (w), 602 (w), 548 (w), 461 (m); $^1$H NMR (400 MHz, CDCl$_3$): δ 7.39 7.27 (13H, m), 7.25-7.23 (7H, m), 5.85 (1H, ddd, J=17.2, 10.6, 5.2 Hz), 5.27 (1H, br s), 5.20 (1H, ddd, J=17.2, 1.2, 1.2 Hz), 5.12 (1H, ddd, J=10.4, 1.4, 1.4 Hz), 4.92 (1H, d, J=11.6 Hz), 4.82 (1H, d, J=11.6 Hz), 4.80 (1H, d, J=3.6 Hz), 4.79 (1H, d, J=12.0 Hz), 4.72 (1H, d, J=11.6 Hz), 4.64 (1H, d, J=11.6 Hz), 4.55 (1H, d, J=11.6 Hz), 4.49 (1H, d, J=12.0 Hz), 4.38 (1H, d, J=12.0 Hz), 4.28 (1H, br s), 4.03 (1H, dd, J=10.0, 3.6 Hz), 3.94-3.92 (2H, m), 3.89 (1H, dd, J=10.0, 2.8 Hz), 3.66-3.62 (2H, m), 3.52-3.44 (2H, m), 1.42 (9H, s); $^{13}$C NMR (100 MHz, CDCl$_3$): δ 155.6, 138.8, 138.7, 138.6, 138.0, 136.4, 128.5, 128.5, 128.4, 128.3, 128.0, 127.9, 127.8, 127.8, 127.7, 127.6, 127.6, 115.9, 99.2, 85.3, 78.9, 76.8, 75.0, 74.9, 73.6, 73.5, 73.2, 69.9, 69.1, 28.5; HRMS (ESI$^+$) [M+Na]$^+$ calcd for C$_{43}$H$_{51}$NO$_8$Na: 732.3512, found: 732.3539; [α]$^{20}_D$+30.7 (c 2.05, CDCl$_3$) for a sample of 98:2 e.r. (e.r. measured for (R)—N-phthaloyl-2-aminobut-3-en-1-ol).

Bis(Boc)amide 20. An oven-dried 12-mL vial equipped with a stir bar was charged with amide I (201 mg, 0.283 mmol), Boc$_2$O (840 mg, 3.85 mmol), DMAP (93.0 mg, 0.764 mmol), and anhydrous MeCN (10 mL). The reaction mixture was allowed to stir for 12 h at 22° C. The resulting red solution was concentrated in vacuo, and the red oil filtered through a short plug of silica gel (eluted with 90:10 hexanes:EtOAc). The resulting yellow oil was purified on silica gel (92.5:7.5 hexanes:EtOAc) to provide a light yellow oil that was dissolved in benzene, and filtered through a plug of basic alumina, to afford bis(Boc)amide 20 (98.0 mg, 0.121 mmol, 43.0% yield) as a colorless oil. IR (neat): 3089 (w), 3064 (w), 3032 (w), 2978 (w), 2925 (w), 1741 (m), 1701 (m), 1496 (w), 1478 (w), 1454 (w), 1390 (w), 1367 (m), 1349 (m), 1306 (w), 1233 (m), 1098 (s), 1042 (s), 1028 (w), 995 (w), 847 (w), 808 (w), 734 (s), 696 (s), 677 (s), 610 (w), 550 (w), 463 (w); $^1$HNMR (400 MHz, CDCl$_3$): δ 7.35-7.27 (13H, m), 7.25-7.22 (7H, m), 5.96 (1H, ddd, J=17.2, 10.4, 4.4 Hz), 5.24 (1H, dt, J=17.6, 1.2 Hz), 5.16 (1H, dt, J=10.8, 1.6 Hz), 4.98 (1H, dd, J=13.2, 6.8 Hz), 4.92 (1H, d, J=11.6 Hz), 4.87 (1H, d, J=4.0 Hz), 4.80 (1H, d, J=11.2 Hz), 4.74 (1H, d, J=12.0 Hz), 4.69 (1H, d, J=13.2 Hz), 4.66 (1H, d, J=12.0 Hz), 4.55 (1H, d, J=11.6 Hz), 4.47 (1H, d, J=12.0 Hz), 4.39 (1H, d, J=12.0 Hz), 4.02 (1H, dd, J=10.0, 3.6 Hz), 3.98-3.95 (2H, m), 3.91 (1H, dd, J=10.0, 2.8 Hz), 3.83 (2H, dd, J=10.0, 7.2 Hz), 3.53-3.51 (2H, m), 1.46 (18H, s); $^{13}$C NMR (100 MHz, CDCl$_3$): δ 153.0, 139.0, 138.9, 138.8, 138.1, 134.9, 128.5, 128.4, 128.4, 128.3, 128.3, 127.9, 127.9, 127.8, 127.6, 127.5, 117.6, 97.8, 82.5, 79.0, 76.6, 75.2, 74.9, 73.5, 73.3, 72.8, 69.5, 69.2, 69.0, 58.0, 28.2; HRMS (ESI$^+$) [M+Na]$^+$ calcd for C$_{48}$H$_{59}$NO$_{10}$Na: 832.4037, found: 832.4028; [α]$^{20}_D$+19.3 (c 1.65, CDCl$_3$) for a sample of 98:2 e.r. (e.r. measured for (R)—N-phthaloyl-2-aminobut-3-en-1-ol).

Z-allylic bis(Boc)amide 21. Following the allylic amide cross metathesis general procedure, substrate 20 (33.4 mg, 0.0412 mmol) was treated with 1-hexadecene (56.0 μL, 0.196 mmol), 8.0 mol % of in situ-generated complex 2 (165.0 μL, 0.02 M, 3.30 μmol; final substrate concentration=0.3 M) and allowed to stir under vacuum for 5 h. The unpurified product is 97% Z (as determined by 400 MHz $^1$H NMR analysis). The resulting brown oil was purified by silica gel chromatography (90:10 hexanes:EtOAc) to afford 21 (36.0 mg, 0.0358 mmol, 87.0% yield, >98% Z isomer) as a clear, colorless oil. IR (neat): 3064 (w), 3030 (w), 2923 (m), 2853 (w), 1741 (m), 1699 (m), 1605 (w), 1497 (w), 1454 (m), 1390 (m), 1366 (m), 1349 (w), 1304 (w), 1233 (m), 1154 (w), 1131 (w), 1100 (s), 1044 (s), 1028 (w), 999 (w), 908 (w), 850 (w), 809 (w), 733 (s), 696 (s), 611 (w), 462 (w), 419 (w); $^1$H NMR (400 MHz, CDCl$_3$): δ 7.36-7.27 (14H, m), 7.25-7.22 (6H, m), [diagnostic E isomer signal: 5.73-5.66 (2H, m)], 5.61-5.51 (2H, m), 5.26 (1H, dd, J=14.0, 7.2 Hz), 4.92 (1H, d, J=11.6 Hz), 4.85 (1H, d, J=3.6 Hz), 4.80 (1H, d, J=11.6 Hz), 4.73 (1H, d, J=12.0 Hz), 4.69 (1H, d, J=11.6 Hz), 4.66 (1H, d, J=12.0 Hz), 4.55 (1H, d, J=11.6 Hz), 4.48 (1H, d, J=11.6 Hz), 4.39 (1H, d, J=12.0 Hz), 4.02 (1H, dd, J=10.0, 3.6 Hz), 3.99-3.96 (2H, m), 3.92 (1H, dd, J=10.0, 2.8 Hz), 3.84-3.78 (2H, m), 3.56-3.48 (2H, m), 2.13-2.06 (2H, m), 1.46 (18H, s), 1.34-1.24 (24H, m), 0.88 (3H, t, J=7.0 Hz); $^{13}$C NMR (100 MHz, CDCl$_3$): δ 152.9, 139.1 139.1, 138.9, 138.2, 135.8, 128.5, 128.4, 128.4, 128.3, 127.9, 127.7, 127.6, 127.5, 125.7, 97.8, 82.2, 79.1, 76.6, 75.3, 74.9, 73.5, 73.4, 72.6, 69.7, 69.4, 69.0, 52.8, 32.1, 29.9, 29.8, 29.8, 29.7, 29.6, 29.5, 28.2, 22.8, 14.3; HRMS (ESI$^+$) [M+Na]$^+$ calcd for C$_{62}$H$_{87}$NO$_{10}$Na: 1028.6228, found: 1028.6196; [α]$^{20}_D$+10.5 (c 1.99, CDCl$_3$) for a sample of 98:2 e.r, >98:2 Z:E (e.r. measured for (R)—N-phthaloyl-2-aminobut-3-en-1-ol).

Dihydroxylamide 22. An 8-mL vial equipped with a stir bar was charged with NMO (15.0 mg, 0.128 mmol), and CH$_2$Cl$_2$ (0.2 mL). The resulting solution was allowed to cool to 0° C. (icebath) and OsO$_4$ (17.0 μL, 2.60 μmol, 4% wt/v aqueous solution) was added. The mixture was allowed to stir for 15 min at 0° C., then Z olefin 21 (51.2 mg, 0.0510 mmol) was introduced via syringe as a solution in CH$_2$Cl$_2$ (0.4 mL). The resulting solution was allowed to warm to 22° C. and stirred for 24 h. After 24 h, the mixture had formed a cloudy brown solution. The reaction was quenched by addition of a saturated aqueous solution of sodium thiosulfate (4 mL), and allowed to stir for 20 min. The biphasic mixture was transferred to a separatory funnel containing a saturated aqueous solution of sodium thiosulfate (20 mL). The organic layer was separated, and the aqueous layer was washed with CH$_2$Cl$_2$ (5×20 mL). The combined organic layers were washed with brine (1×20 mL), dried over MgSO$_4$, filtered, and concentrated in vacuo. The resulting brown oil was purified by silica gel chromatography (80:10:10 hexanes:EtOAc:CH$_2$Cl$_2$) to afford diol 22 (53.0 mg, 0.0510 mmol, >98% yield) as a colorless oil, and as a mixture of diastereomers (89:11 anti:syn). IR (neat): 3467 (w), 3066 (w), 3031 (w), 2955 (m), 2924 (w), 2854 (w), 1736 (m), 1687 (m), 1497 (w), 1455 (m), 1392 (w), 1367 (m), 1352 (w), 1235 (w), 1154 (w), 1124 (w), 1097 (s), 1056 (m), 1028 (w), 908 (m), 852 (w), 806 (w), 731 (s), 696 (s), 648 (w), 608 (w), 462 (w); $^1$HNMR (400 MHz, CDCl$_3$): δ 7.38-7.27 (14H, m), 7.26-7.25 (6H, m), 4.90 (1H, d, J=11.6 Hz), 4.83 (1H, d, J=3.2 Hz), 4.82 (1H, d, J=12.4 Hz), 4.78 (1H, d, J=13.6 Hz), 4.75 (1H, d, J=12.4 Hz), 4.70 (1H, d, J=12.0 Hz), 4.54 (1H, d, J=11.6 Hz), 4.49 (1H, d, J=12.0 Hz), 4.40 (2H, d, J=12.0 Hz), 4.21 (1H, dd, J=11.4, 7.0 Hz), 4.03-4.00 (2H, m), 3.92-3.89 (2H, m), 3.78 (1H, dd, J=6.4, 3.2 Hz), 3.67 (1H, dd, J=11.2, 5.6 Hz), 3.57 (1H, br s), 3.54-3.45 (3H, m), 3.20 (1H, d, J=4.8 Hz), 1.48 (18H, s), 1.30-1.24 (24H, m), 0.88 (3H, t, J=7.0 Hz); $^{13}$C NMR (100 MHz, CDCl$_3$): δ 154.1, 138.8, 138.7, 138.3, 138.0, 128.5, 128.5, 128.3, 128.3, 128.0, 127.8, 127.7, 127.6, 127.5, 98.3, 83.4, 79.3, 75.9, 75.2, 74.8, 73.5, 73.3, 72.4, 69.8, 69.3, 65.8, 57.6, 33.2, 32.1, 29.9, 29.9, 29.9, 29.8, 29.5, 28.1, 26.2, 22.8, 14.3; HRMS (ESI$^+$) [M+Na]$^+$ calcd for C$_{62}$H$_{89}$NO$_{12}$Na: 1062.6282, found: 1062.6313; [α]$^{20}_D$+16.9 (c 1.26, CDCl$_3$) for a sample of 98:2 e.r. and 89:11 anti:syn (e.r. measured for (R)—N-phthaloyl-2-aminobut-3-en-1-ol).

2',3',4',6'-tetra-O-benzyl KRN7000 (24). An 8-mL vial equipped with a stir bar was charged with diol 22 (12.4 mg, 12.0 μmol). Trifluoroacetic acid (1.0 mL, 10% v/v in CH$_2$Cl$_2$) was added, and the mixture was allowed to stir for 30 min at 22° C. The reaction was quenched by addition of sodium bicarbonate (100 mg), and allowed to stir for 5 min. The mixture was diluted with CH$_2$Cl$_2$ (4 mL), passed through a plug of cotton, and the resulting solution concentrated in vacuo to afford a colorless oil. A separate vial was charged with succinimide ester 23 (7.1 mg, 14.4 μmol) and triethylamine (50 μL, 0.346 mmol), and 0.5 mL CH$_2$Cl$_2$ was added.

The resulting solution was transferred to the vial containing the free-base amine, and the resulting solution was allowed to stir for 12 h in an oil bath (50° C.). The mixture was cooled, concentrated in vacuo, and the resulting white solid was purified by silica gel chromatography (3:1 hexanes:EtOAc), affording ceramide 24 (13.0 mg, 10.7 μmol, 89.0% yield) as a white crystalline solid, and as a single diastereomer [>98:2 d.r. (anti:syn)]. M.P. 59-61° C. (Lit. m.p. 71° C.); IR (neat): 3317 (br w), 2918 (s), 2850 (m), 1741 (w), 1639 (w), 1543 (w), 1496 (w), 1466 (m), 1454 (w), 1377 (w), 1351 (w), 1260 (m), 1209 (w), 1094 (m), 1041 (s), 1027 (s), 909 (w), 867 (s), 798 (w), 731 (s), 608 (w), 462 (w); $^1$H NMR (400 MHz, CDCl$_3$): δ 7.36-7.27 (20H, m), 6.37 (1H, d, J=8.5 Hz), 4.92 (1H, d, J=11.0 Hz), 4.88 (1H, d, J=11.5 Hz), 4.84 (1H, d, J=3.0 Hz), 4.78 (2H, d, J=4.0 Hz), 4.67 (1H, d, J=11.5 Hz), 4.56 (1H, d, J=11.5 Hz), 4.47 (1H, d, J=11.5 Hz), 4.39 (1H, d, J=11.5 Hz), 4.21-4.20 (1H, m), 4.04 (1H, dd, J=10.0, 3.5 Hz), 3.97 (1H, br s), 3.92-3.85 (4H, m), 3.80 (1H, d, J=9.0 Hz), 3.51-3.47 (4H, m), 2.11 (2H, t, J=7.3 Hz), 1.58-1.43 (6H, m), 1.25 (66H, m), 0.88 (6H, t, J=6.6 Hz); $^{13}$C NMR (100 MHz, CDCl$_3$): δ 173.3, 138.6, 138.5, 138.0, 137.7, 128.6, 128.4, 128.3, 128.3, 128.1, 128.1, 127.9, 127.8, 127.6, 99.4, 79.5, 76.4, 76.2, 74.9, 74.6, 74.4, 73.8, 73.5, 72.9, 70.2, 70.1, 69.1, 49.7, 36.9, 33.4, 32.1, 29.9, 29.7, 29.5, 26.1, 25.9, 22.8, 14.3; HRMS (ESI$^+$) [M+Na]$^+$ calcd for C$_{78}$H$_{123}$NO$_9$Na: 1240.9096, found: 1240.9098; [α]$^{20}_D$+9.71 (c 0.387, CDC$^{13}$) for a sample of 98:2 e.r. and >98:2 d.r. [([α]$^{20}_D$+27.6 (c 2.10, CHCl$_3$) for a sample of >98:2 e.r.].

Example 10

Exemplary Catalysts for Use in the Present Invention

The following Mo-based alkylidene complexes are useful in the above-described methods of the present invention.

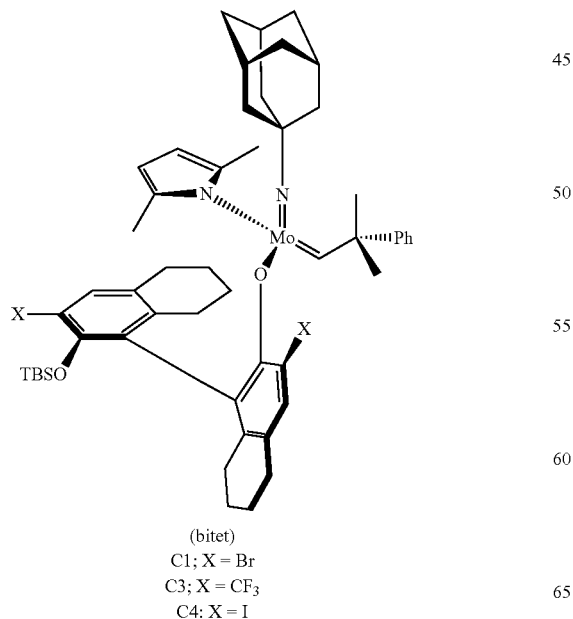

(bitet)
C1; X = Br
C3; X = CF$_3$
C4; X = I

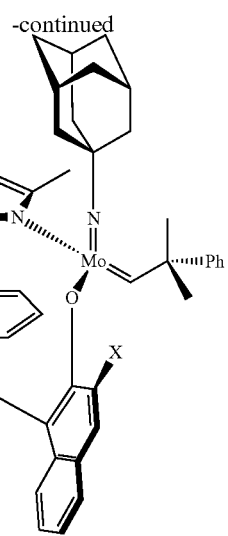

(binol)
C5; X = Br
C6; X = CF$_3$
C7; X = I

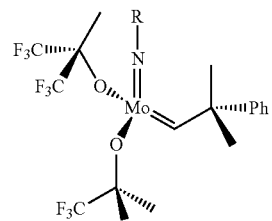

C8; R = 2,6-i-Pr$_2$—C$_6$H$_3$
C9; R = Ad

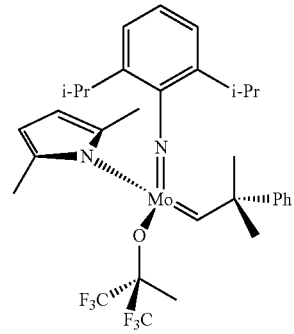

C10

TABLE 9

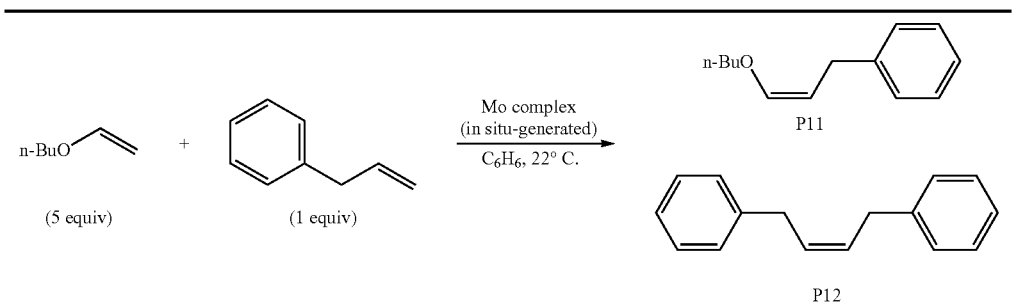

| entry | mol %; Mo Complex | Concentration | Time | % conv Z-P11; % conv E-P11[a] | % conv Z-P12; % conv E-P12[b] |
|---|---|---|---|---|---|
| 1 | 2.5 mol %; C8 | 0.1M | 10 min | 35; 25 | 9; 30 |
| 2 | 2.5 mol %; C8 | 4.0M | 10 min | 33; 29 | 5; 18 |
| 3 | 2.5 mol %; C9 | 0.1M | 10 min | 31; 7 | <2; <2 |
| 4 | 2.5 mol %; C9 | 4.0M | 10 min | 17; 4 | <2; <2 |
| 5 | 1.5 mol %; C1 | 4.0M | 2 h | 46; 2 | 8; 3 |
| 6 | 1.2 mol %; C5 | 4.0M | 2 h | 52; 3.5 | 4; 2 |
| 7 | 1.2 mol %; C5 | 4.0M | 10 min | 61; 3 (61%)[c,d] | 5; 2 |
| 8 | 2.5 mol %; C3 | 0.8M | 2 h | 50; 2 | 11; 5 |
| 9 | 2.5 mol %; C6 | 0.8M | 1 h | 39; 2 | 2; <2 |
| 10 | 2.5 mol %; C4 | 0.1M | 2 h | 12; <2 | 2.5; <2 |
| 11 | 1.2 mol %; C7 | 0.8M | 1 h | 78; 4 | 6; <2 |

[a]Reactions were performed under $N_2$ atmosphere in $C_6H_6$ at 22° C.
[b]Conversions were determined by analysis of 400 MHz $^1$H NMR spectra of unpurified mixtures prior to purification.
[c]Yield of isolated products after purification.
[d]Combined yields of the product E/Z mixture.

Example 11

Exemplary Catalysts for Use in the Present Invention

TABLE 10

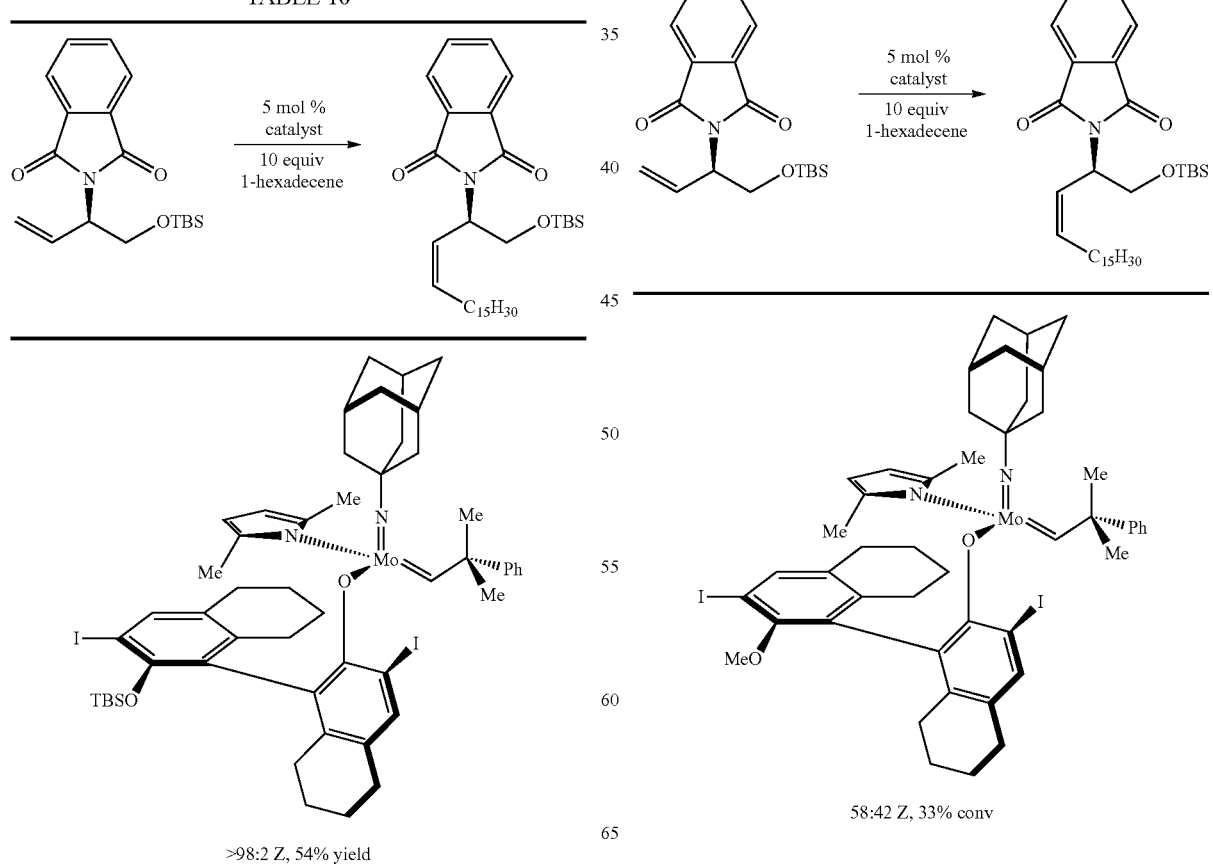

TABLE 10-continued

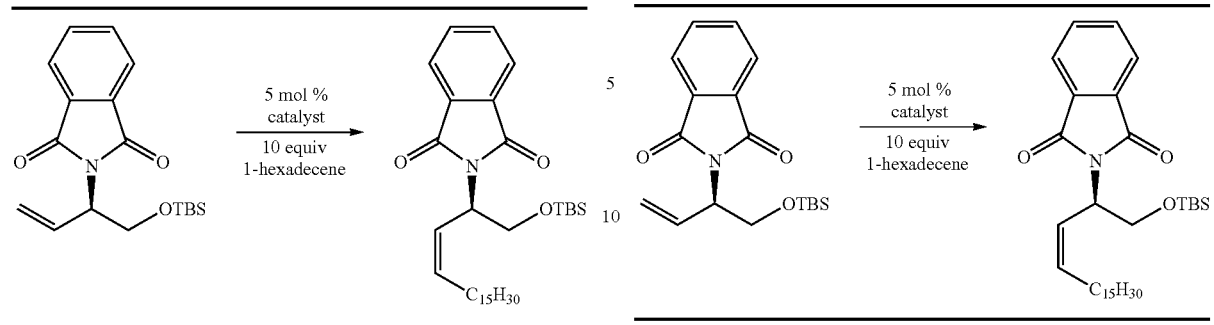

97
TABLE 10-continued
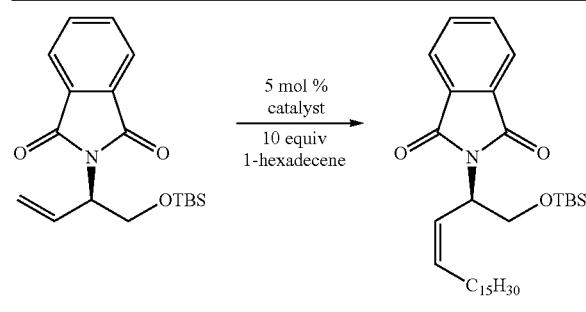
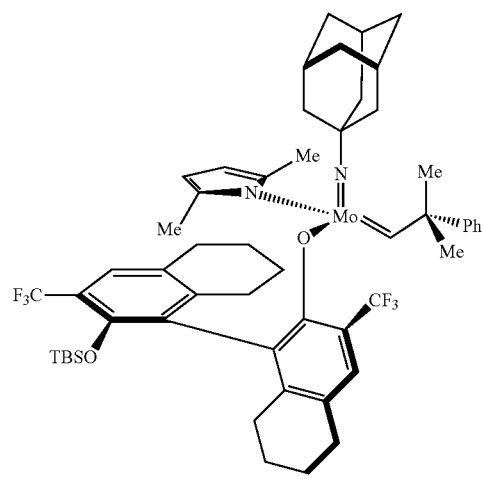
>98:2 Z, 51% conv
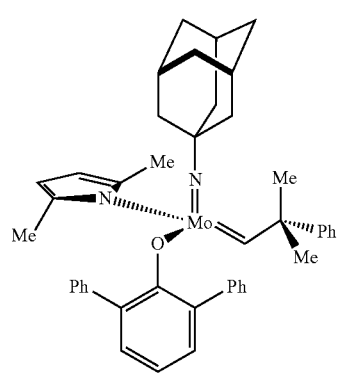
43:57 Z, 51% conv
98
TABLE 10-continued
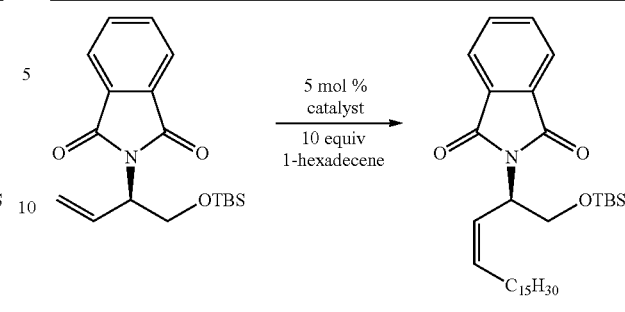
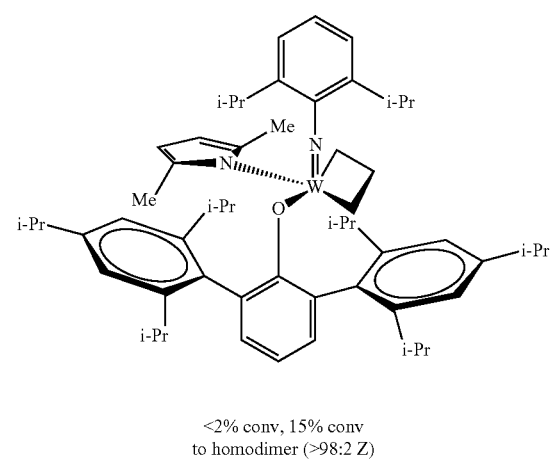
<2% conv, 15% conv
to homodimer (>98:2 Z)
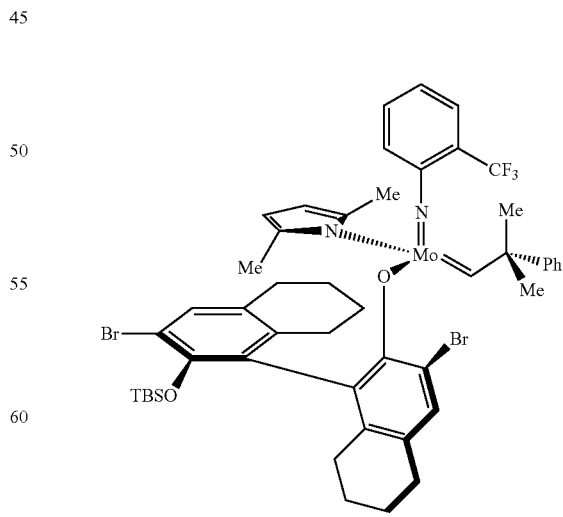
66:34 Z, 69% conv

TABLE 10-continued
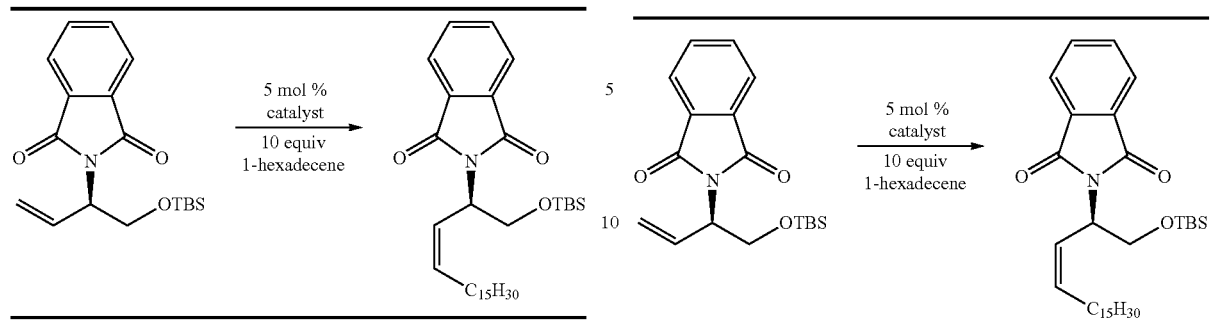
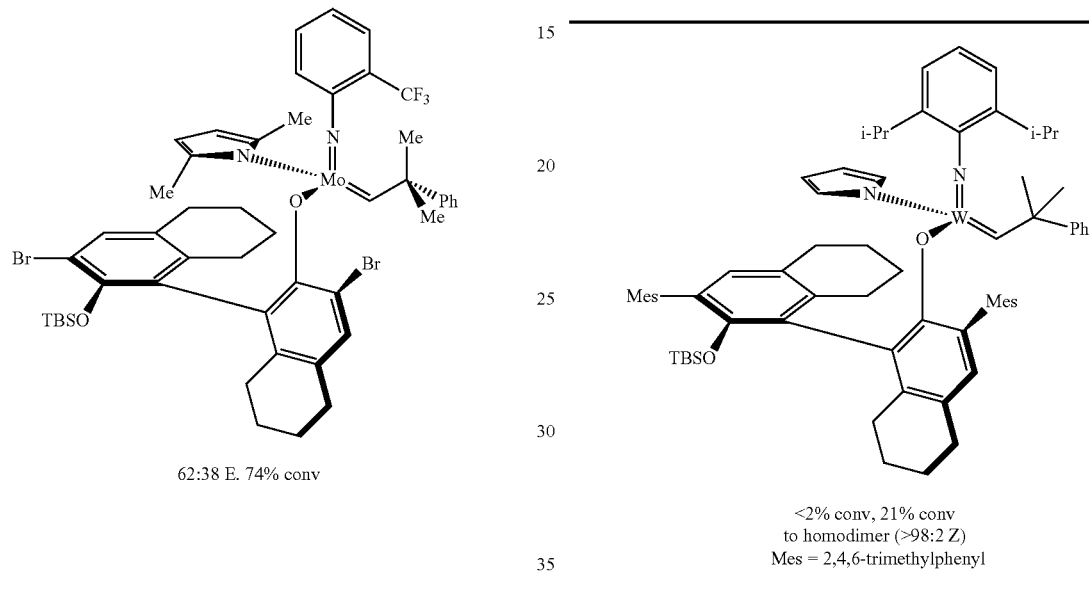
The homodimer described above refers to the homodimer of the allylic amide.
Example 12
Exemplary Catalysts for Use in the Present Invention
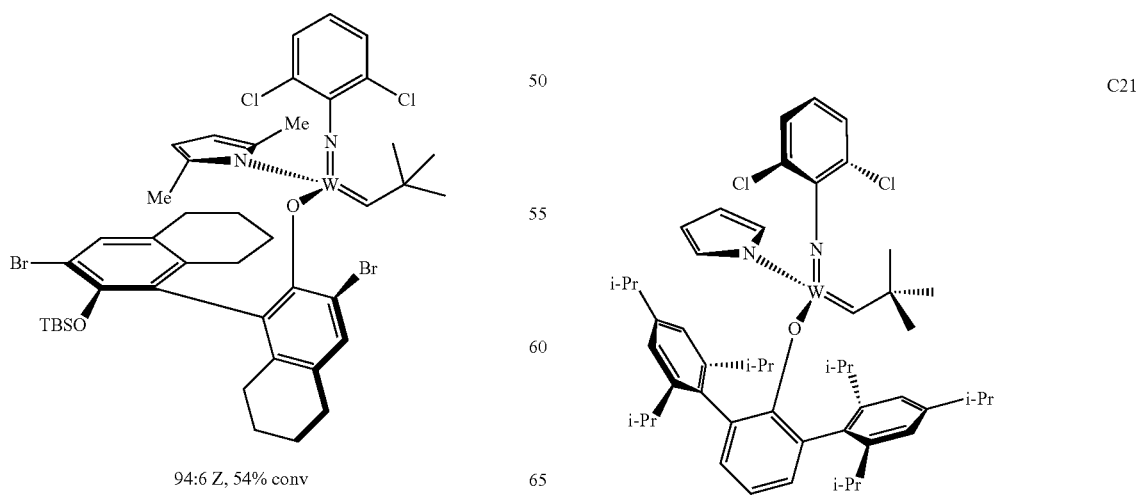

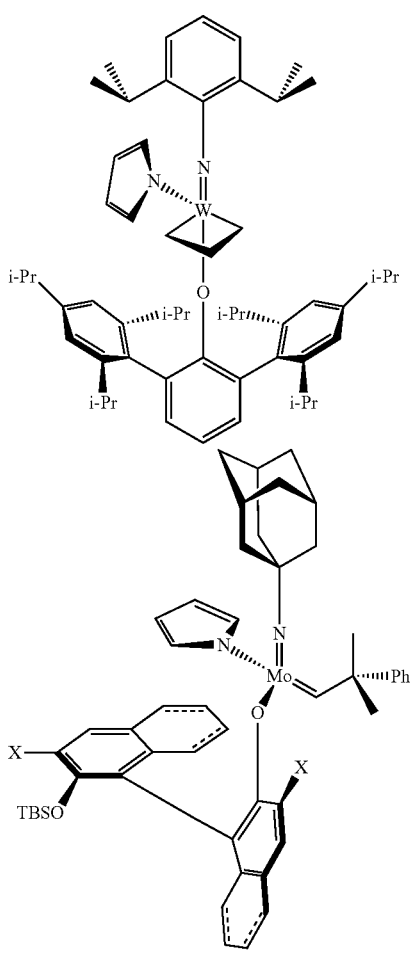

C23; bitet, X = Br
C24; binol, X = Br
C25; bitet, X = I

Example 13

Mechanistic Basis

Figure 2:
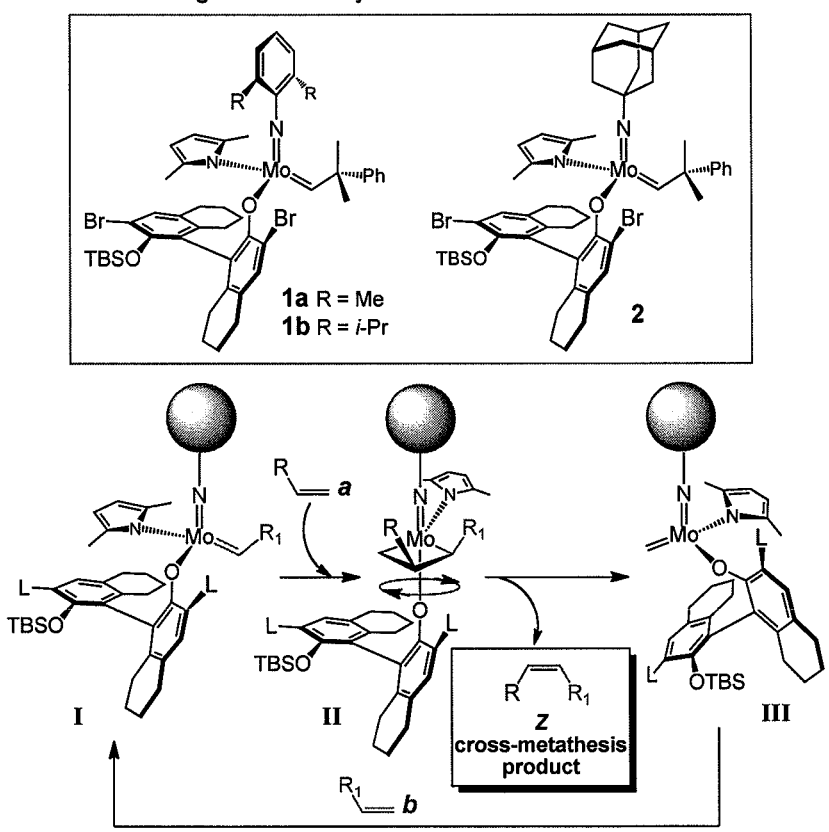
FIG. 2 shows examples of metal catalysts that may be used in metathesis reactions.

As shown in FIG. 2, reaction of alkylidene I, derived from reaction of one of the cross partners (a) with initial chiral complex, with the other alkene (b) would be expected to result in the formation of all-syn metallacyclobutane II. The lack of preference for generation of the thermodynamically preferred anti metallacycle may be due to the presence of the freely rotating and sizeable aryloxide ligand, which can render positioning of a substituent syn to it energetically disfavored. The relative size as well as electronic attributes of the imido unit can be used to fine-tune the reactivity and/or selectivity levels (e.g., Ia-b and 2, Example 1). Subsequent collapse of the metallacyclobutane II would furnish the Z alkene product, while generating III, which would react with alkene (a) to regenerate I.

Other reactivity and selectivity factors may also facilitate an efficient cross metathesis process. For example, it may be advantageous for the initiating neophylidenes (e.g., 1a-b or 2) or the corresponding Mo methylidenes (e.g., III) to be sufficiently active to react with an electron-rich enol ether as well as a relatively electron deficient and sterically demanding allylic amine. Efficient catalytic olefin metathesis reactions involving enol ethers are relatively scarce. Moreover, it may be desirable for the resulting intermediate alkylidene (e.g., I, FIG. 2) to show *sufficient activity to generate the sterically more demanding productive metallacyclobutane II.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of"or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. A method, comprising:

reacting terminal alkene of formula:

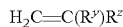

wherein:

R$^y$ is a hydrogen or an optionally substituted group selected from aliphatic, heteroaliphatic, aryl, heteroaryl, or heterocyclyl; and R$^z$ is an optionally substituted group selected from aliphatic, heteroaliphatic, aryl, heteroaryl, or heterocyclyl, with an allylic amine of formula:

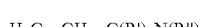

wherein:

each R' is independently hydrogen, —C(O)R$^a$, or an optionally substituted group selected from aliphatic, heteroaliphatic, aryl, heteroaryl, or heterocyclyl;

each R$^a$ is independently hydrogen or optionally substituted group selected from aliphatic, heteroaliphatic, aryl, heteroaryl, or heterocyclyl; and each R" is independently —C(O)R$^a$, an amino protecting group, or an optionally substituted group selected from aliphatic, heteroaliphatic, aryl, heteroaryl, or heterocyclyl, to form a cross-metathesis product with a Z:E ratio greater than 1:1.

2. The method according to claim 1, wherein the reacting step is performed in the presence of a chiral metal complex of formula I:

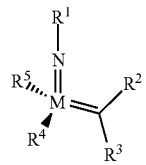

wherein:

M is Mo or W;

R$^1$ is an optionally substituted group selected from aryl, heteroaryl, aliphatic, or heteroaliphatic;

each of R$^2$ and R$^3$ is independently hydrogen, or an optionally substituted group selected from aliphatic, heteroaliphatic, aryl, or heteroaryl;

R$^4$ is an optionally substituted group selected from —O-alkyl, —O-heteroalkyl, —O-aryl, —O-heteroaryl, —N(R")-alkyl, —N(R")-heteroalkyl, —N(R")-aryl, or —N(R")-heteroaryl;

each R" is independently hydrogen, an amino protecting group, or an optionally substituted aliphatic; and R$^5$ is halogen or an optionally substituted group selected from aryl, heteroaryl, aliphatic, heteroaliphatic, —O-alkyl, —O-heteroalkyl, —O-aryl, or —O-heteroaryl.

3. The method according to claim 2, wherein R$^4$ is an optionally substituted asymmetric —O-aryl group and R$^5$ is an optionally substituted heteroaryl group.

4. The method according to claim 3, wherein R$^1$ is an optionally substituted group selected from aryl or aliphatic.

5. The method according to claim 4, wherein R$^1$ is

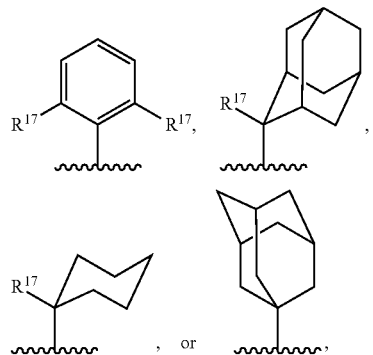

wherein each R$^{17}$ is independently hydrogen or a monovalent substituent.

6. The method according to claim 5, wherein R$^5$ is an optionally substituted group selected from

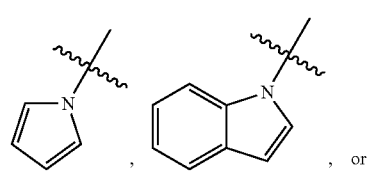

-continued
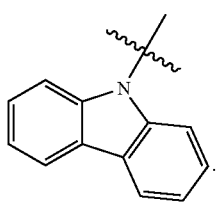
7. The method according to claim 6, wherein $R^4$ is an optionally substituted group selected from:
-continued
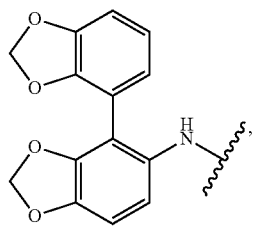
, and
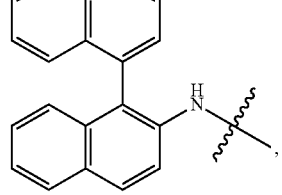
8. The method according to claim 2, wherein the metal complex comprises any one of the catalysts depicted below:
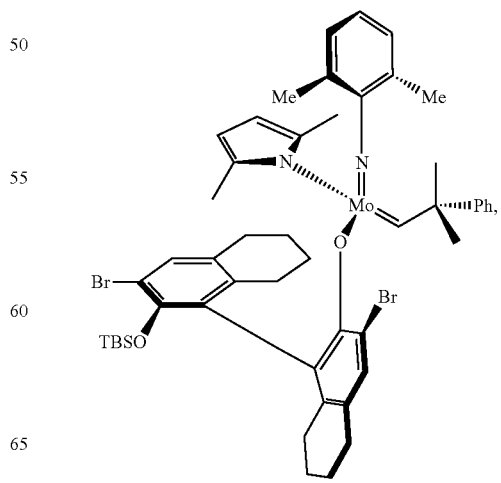

107
-continued
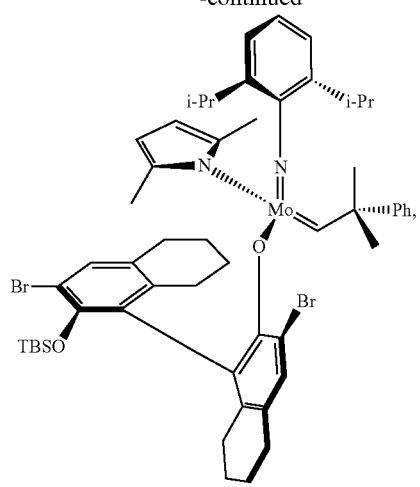
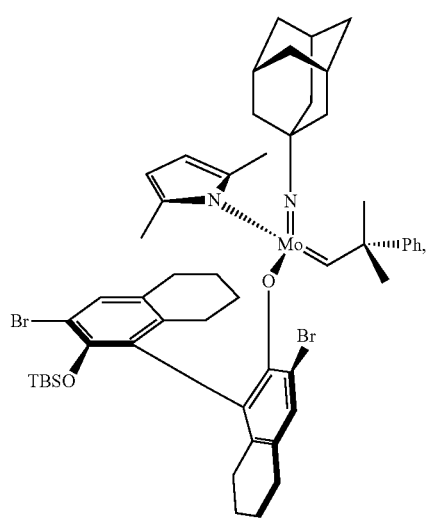
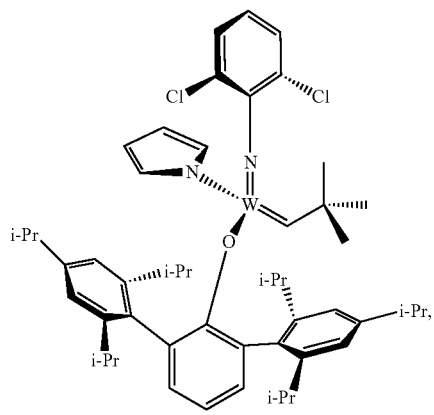
108
-continued
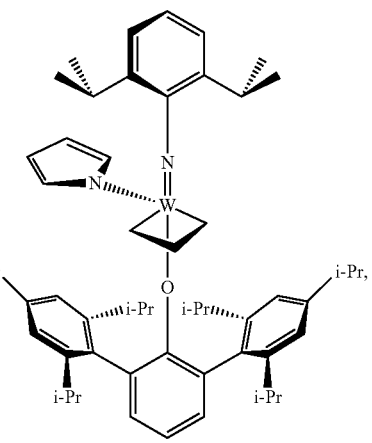
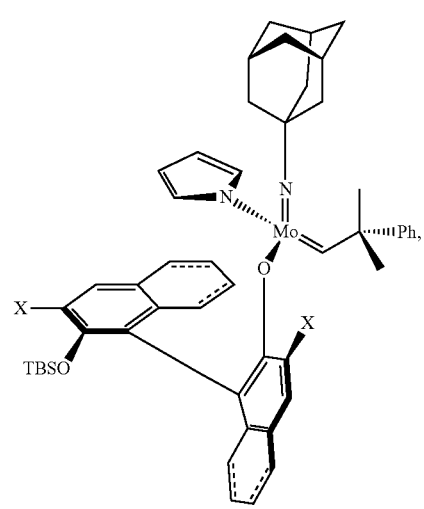
wherein each X is bromo or iodo,
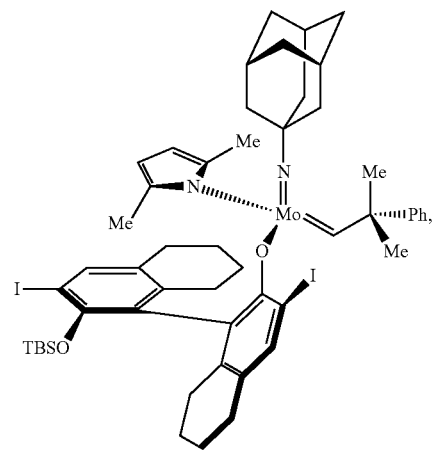

109
-continued
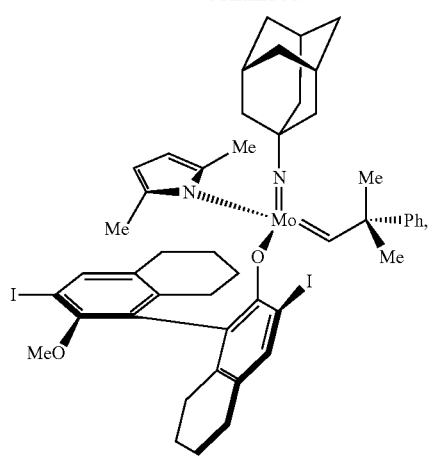
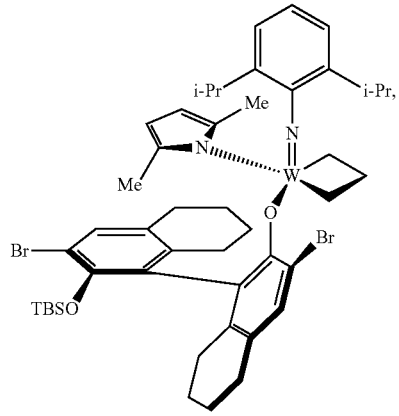
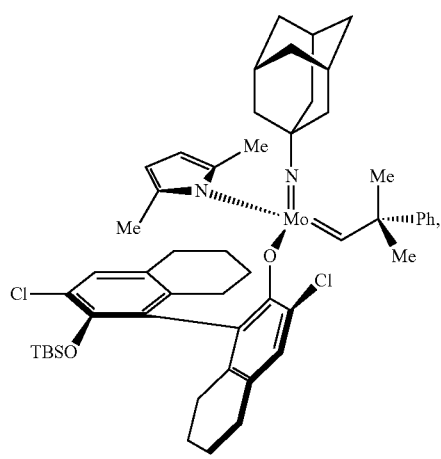
110
-continued
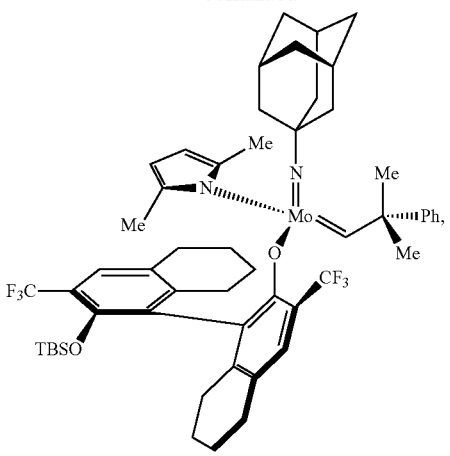
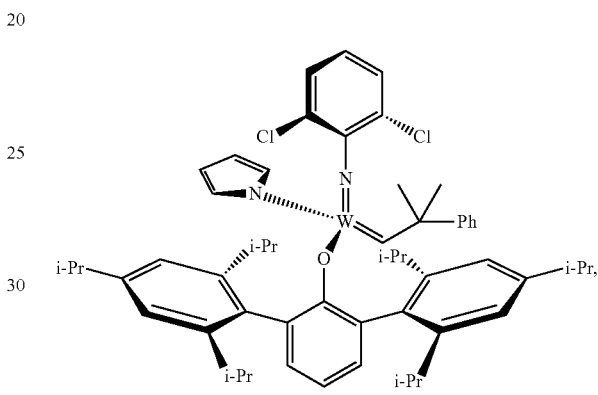
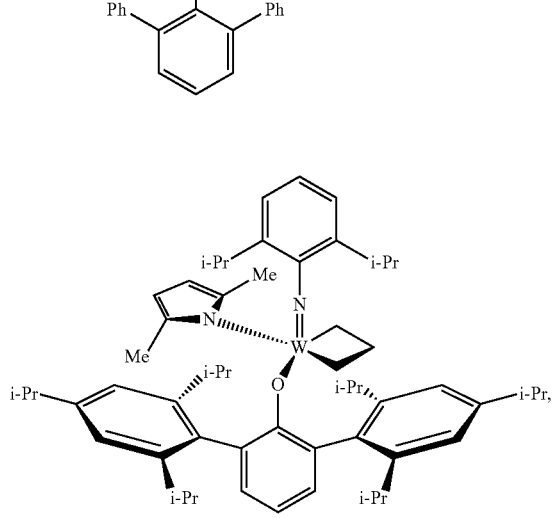

111
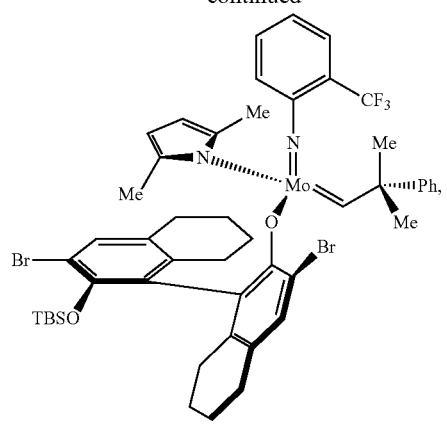
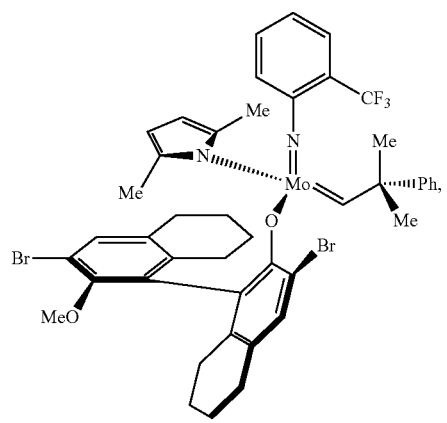
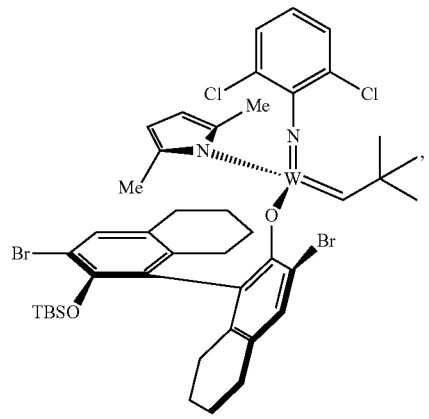
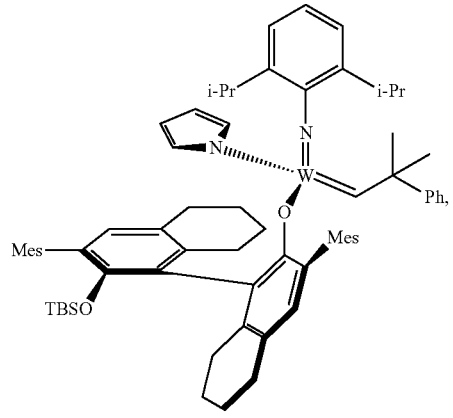
wherein Mes is 2,4,6-trimethylphenyl;
112
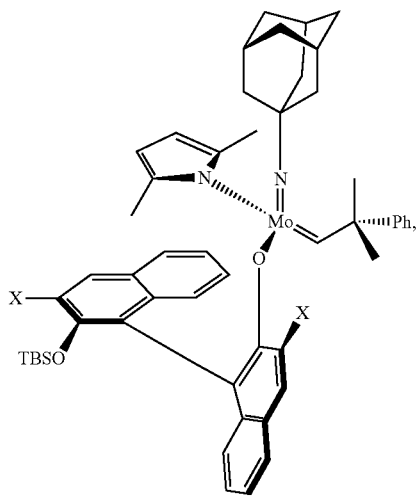
wherein each X is bromo, iodo, or —CF$_3$,
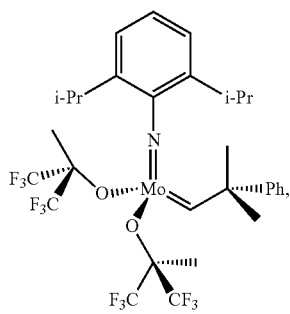
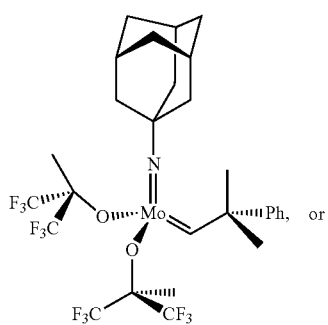
or
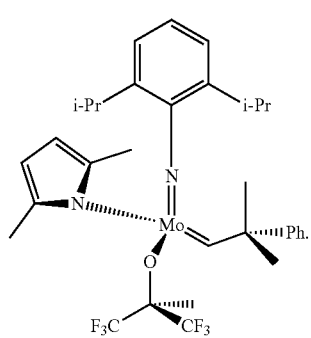

9. A method, comprising:

reacting terminal alkene of formula:

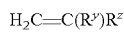

wherein:

R$^y$ is a hydrogen or an optionally substituted group selected from aliphatic, heteroaliphatic, aryl, heteroaryl, or heterocyclyl; and R$^z$ is an optionally substituted group selected from aliphatic, heteroaliphatic, aryl, heteroaryl, or heterocyclyl, with an enol ether of formula:

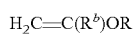

wherein:

R is —C(O)R$^a$, a hydroxyl protecting group, or an optionally substituted group selected from aliphatic, heteroaliphatic, aryl, heteroaryl, or heterocyclyl;

R$^a$ is hydrogen or optionally substituted group selected from aliphatic, heteroaliphatic, aryl, heteroaryl, or heterocyclyl; and R$^b$ is hydrogen or optionally substituted aliphatic, to form a cross-metathesis product with a Z:E ratio greater than 1:1.

10. The method according to claim 9, wherein the reacting step is performed in the presence of a chiral metal complex of formula I:

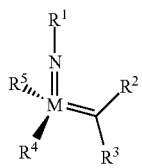

wherein:

M is Mo or W;

R$^1$ is an optionally substituted group selected from aryl, heteroaryl, aliphatic, or heteroaliphatic;

each of R$^2$ and R$^3$ is independently hydrogen, or an optionally substituted group selected from aliphatic, heteroaliphatic, aryl, or heteroaryl;

R$^4$ is an optionally substituted group selected from —O-alkyl, —O-heteroalkyl, —O-aryl, —O-heteroaryl, —N(R″)-alkyl, —N(R″)-heteroalkyl, —N(R″)-aryl, or —N(R″)-heteroaryl;

each R″ is independently hydrogen, an amino protecting group, or an optionally substituted aliphatic; and R$^5$ is halogen or an optionally substituted group selected from aryl, heteroaryl, aliphatic, heteroaliphatic, —O-alkyl, —O-heteroalkyl, —O-aryl, or —O-heteroaryl.

11. The method according to claim 10, wherein R$^4$ is an optionally substituted asymmetric —O-aryl group and R$^5$ is an optionally substituted heteroaryl group.

12. The method according to claim 11, wherein R$^1$ is an optionally substituted group selected from aryl or aliphatic.

13. The method according to claim 12, wherein R$^1$ is

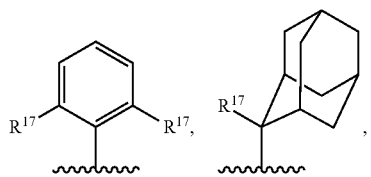

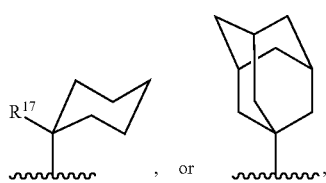

wherein each R$^{17}$ is independently hydrogen or a monovalent substituent.

14. The method according to claim 13, wherein R$^5$ is an optionally substituted group selected from

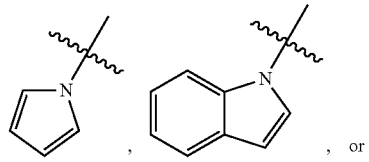

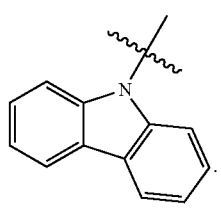

15. The method according to claim 14, wherein R$^4$ is an optionally substituted group selected from:

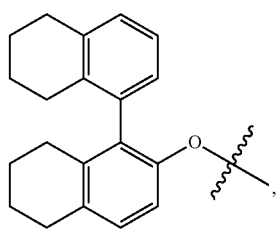

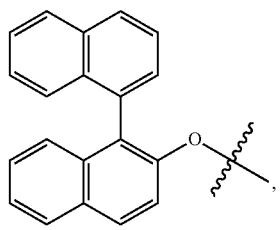

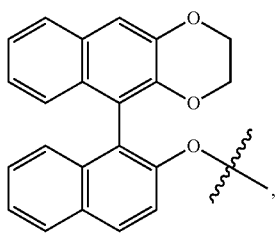
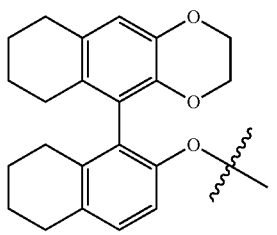
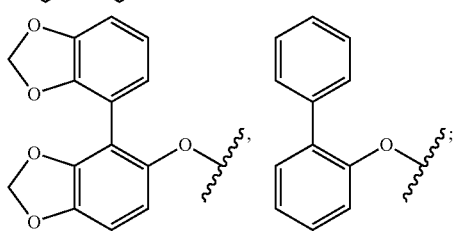
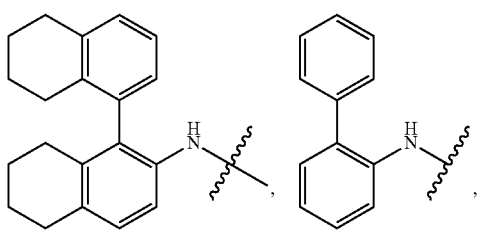
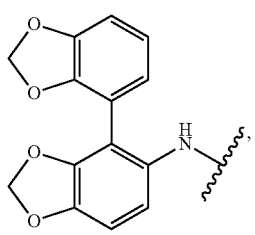
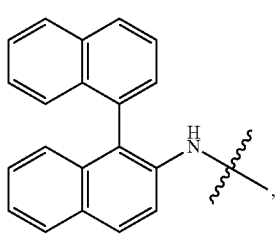
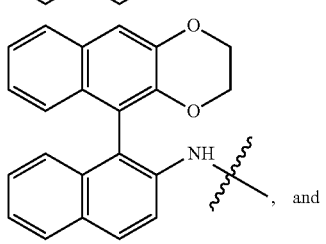, and
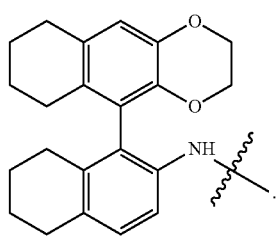
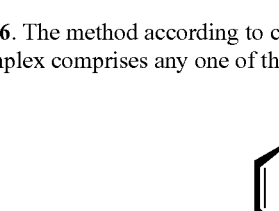.
16. The method according to claim 10, wherein the metal complex comprises any one of the catalysts depicted below:
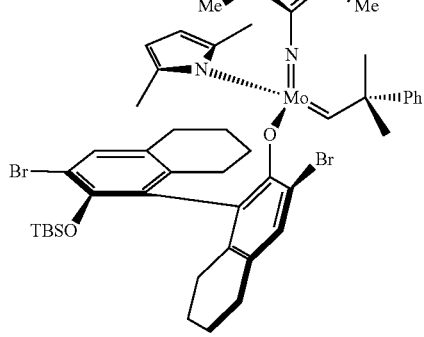
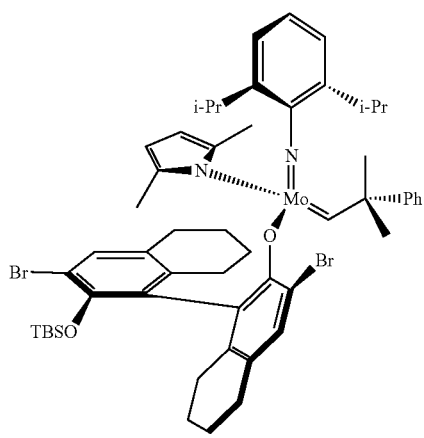
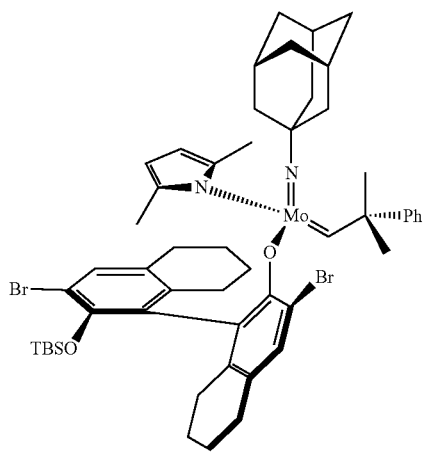

117
-continued
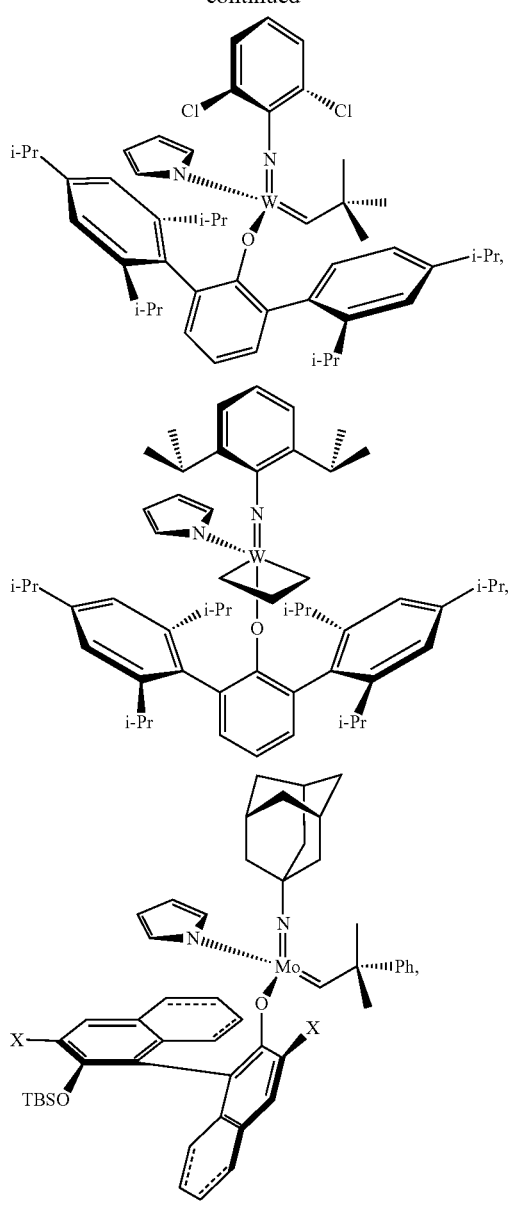
wherein each X is bromo or iodo,
118
-continued
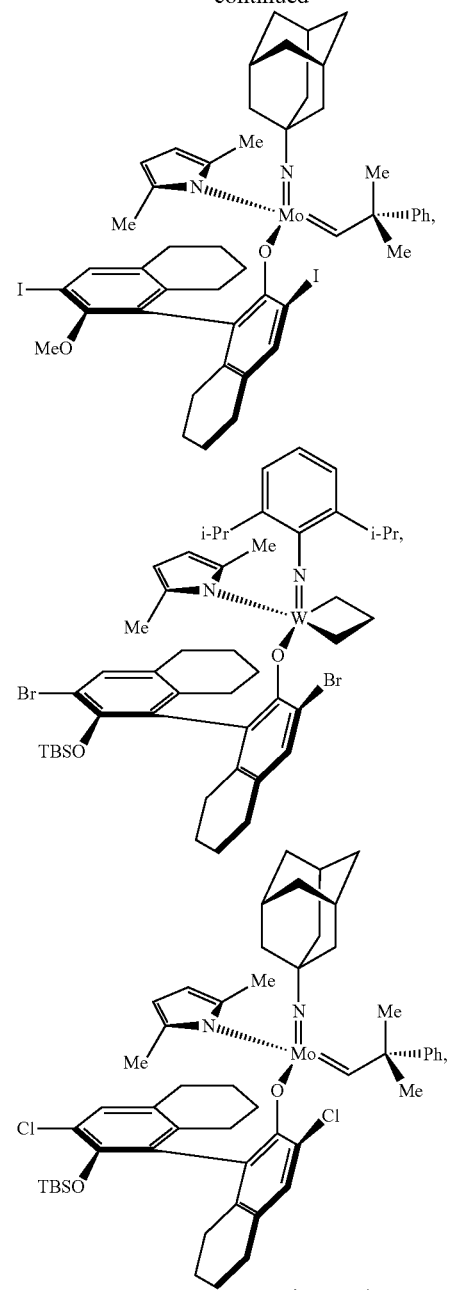

119
-continued
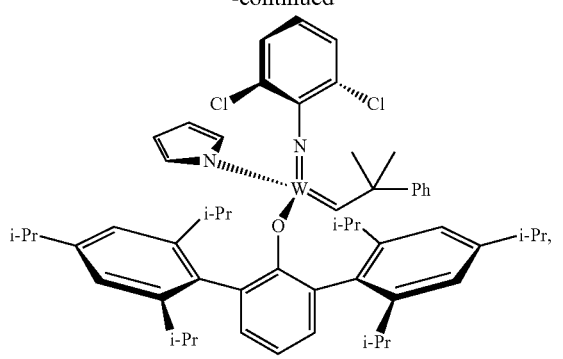
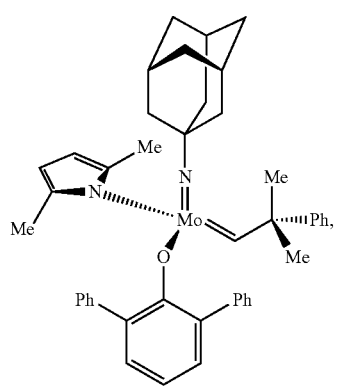
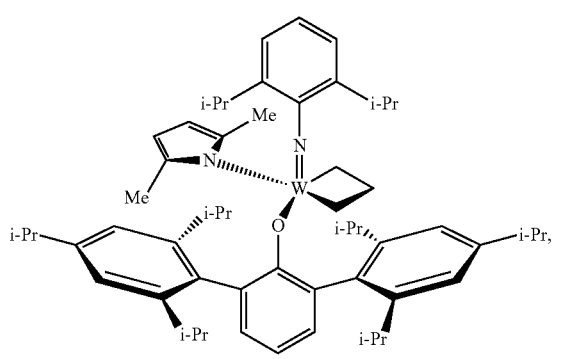
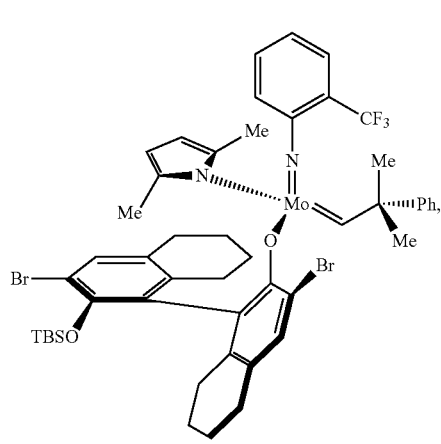
120
-continued
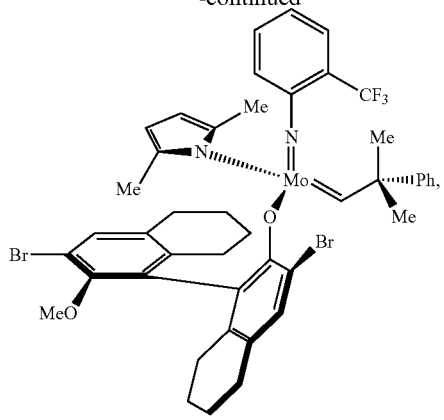
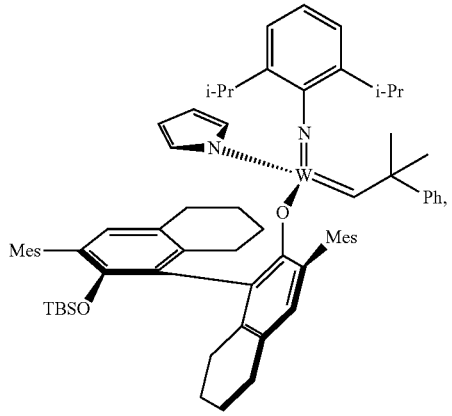
wherein Mes is 2,4,6-trimethylphenyl;

121
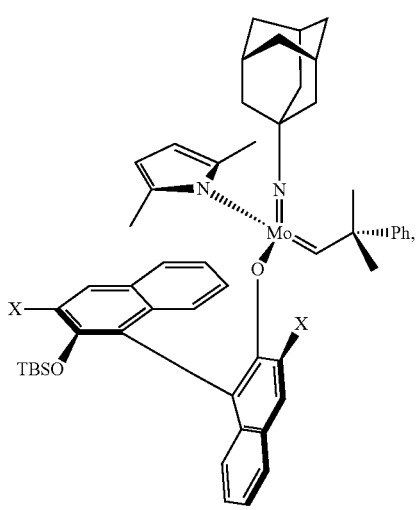
wherein each X is bromo, iodo, or —CF₃,
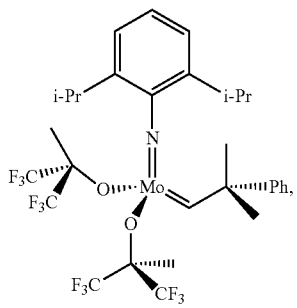
122
-continued
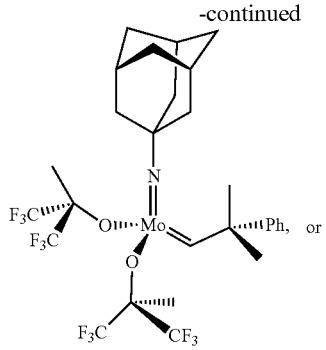
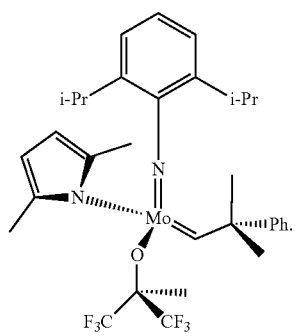
17. The method according to claim 3, wherein $R^4$ is a silyl-protected BINOL derivative.
18. The method according to claim 11, wherein $R^4$ is a silyl-protected BINOL derivative.
* * * * *